(12) United States Patent
Barlaam et al.

(10) Patent No.: US 9,657,008 B2
(45) Date of Patent: *May 23, 2017

(54) CHEMICAL COMPOUNDS

(71) Applicant: AstraZeneca AB, Sodertalje (SE)

(72) Inventors: Bernard Christophe Barlaam, Macclesfield (GB); Benedicte Delouvrie, Macclesfield (GB); Craig Steven Harris, Macclesfield (GB); Christine Marie Paul Lambert-Van der Brempt, Macclesfield (GB); Gilles Ouvry, Macclesfield (GB); Gary Patrick Reid, Macclesfield (GB); David Berry, Macclesfield (GB); Gary Peter Tomkinson, Macclesfield (GB)

(73) Assignee: AstraZeneca AB (SE)

(*) Notice: Subject to any disclaimer, the term of this patent is extended or adjusted under 35 U.S.C. 154(b) by 0 days.

This patent is subject to a terminal disclaimer.

(21) Appl. No.: 14/840,209

(22) Filed: Aug. 31, 2015

(65) Prior Publication Data

US 2016/0137634 A1 May 19, 2016

Related U.S. Application Data

(63) Continuation of application No. 14/160,650, filed on Jan. 22, 2014, now Pat. No. 9,156,831.

(30) Foreign Application Priority Data

Jan. 23, 2013 (EP) .................................... 13305078

(51) Int. Cl.
 *A61K 31/497* (2006.01)
 *C07D 413/14* (2006.01)
 *A61K 45/06* (2006.01)
 *C12Q 1/68* (2006.01)

(52) U.S. Cl.
 CPC .......... *C07D 413/14* (2013.01); *A61K 31/497* (2013.01); *A61K 45/06* (2013.01); *C12Q 1/6886* (2013.01); *C12Q 2600/106* (2013.01); *C12Q 2600/156* (2013.01)

(58) Field of Classification Search
 CPC ........................... A61K 31/497; C07D 413/14
 See application file for complete search history.

(56) References Cited

U.S. PATENT DOCUMENTS

| | | | |
|---|---|---|---|
| 4,011,218 A | 3/1977 | Baldwin et al. | |
| 4,256,887 A | 3/1981 | Novello et al. | |
| 5,656,416 A | 8/1997 | O'Toole | |
| 8,119,671 B2 | 2/2012 | Mita et al. | |
| 8,263,636 B2 | 9/2012 | Ansorge et al. | |
| 8,268,754 B2 | 9/2012 | Mita et al. | |
| 2003/0195195 A1 | 10/2003 | Haviv et al. | |
| 2005/0239800 A1 | 10/2005 | Wang et al. | |
| 2007/0259860 A1 | 11/2007 | Wallberg et al. | |

FOREIGN PATENT DOCUMENTS

| | | |
|---|---|---|
| CN | 101676271 A | 3/2010 |
| JP | 1994279418 A | 10/1994 |
| JP | 2006028056 A | 2/2006 |
| JP | 2010063863 A | 4/2010 |
| JP | 2011178673 A | 9/2011 |
| WO | WO 96/23783 A1 | 8/1996 |
| WO | WO 97/08167 A1 | 3/1997 |
| WO | WO 97/23458 A1 | 7/1997 |
| WO | WO 98/04560 A1 | 2/1998 |
| WO | WO 98/55480 A1 | 12/1998 |
| WO | WO 02/06271 A1 | 1/2002 |
| WO | WO 03/045924 A1 | 6/2003 |
| WO | WO 03/053933 A1 | 7/2003 |
| WO | WO 03/062224 A1 | 7/2003 |
| WO | WO 03/093297 A2 | 11/2003 |
| WO | WO 2004/084325 A1 | 9/2004 |
| WO | WO 2004/084813 A2 | 10/2004 |
| WO | WO 2005/034940 B2 | 4/2005 |

(Continued)

OTHER PUBLICATIONS

Barlaam, B., et al. "Discovery of 1-(4-(5-(5-amino-6-(5-tert-butyl-1,3,4-oxadiazol-2-yl)pyrazine-2-yl)-1-ethyl-1,2,4-triazol-3-yl)piperidin-1-yl)-3-hydroxypropan-1-one (AZD8835): A potent and selective inhibitor of PI3Kα and PI3Kδ for the treatment of cancers." Bioorganic & Medicinal Chemistry Letters. (2015), vol. 25, pp. 5155-5162.*
Mayo Clinic. "Cancer." © 2016. Available from: < http://www.mayoclinic.org/diseases-conditions/cancer/basics/prevention/CON-20032378?p=1 >.*
Fruman, D.A., et al. "PI3K and cancer: lessons, challenges and opportunities." Nature.com. (Feb. 2014), vol. 13, pp. 140-156.*
Wang et al., 'Crystal Structure and Characterization of Two Cadmium(II) Coordination Polymers with a Multidentate N-donor Tecton 3-(pyridine-4-yl)-5-(pyrazin-2-yl)-1H-1,2,4-triazole', Journal of Coordination Chemistry (2013); vol. 66; No. 3; 501-508.
Wilks, 'Protein Tyrosine Kinase Growth Factor Receptors and Their Ligands in Development, Differentiation, and Cancer', Advances in Cancer Research (1993); vol. 60; 43-73.
Wymann et al., 'Phosphoinositide 3-kinase Signalling—Which Way to Target?', Trends in Pharmacological Science (2003); vol. 24; No. 7; 366-376.
Zhao and Vogt, 'Class I PI3K in Oncogenic Cellular Transformation', Oncogene (2008); vol. 27; 5486-5496.
Abid et al., 'Vascular Endothelial Growth Factor Activates PI3K/Akt/Forkhead Signaling in Endothelial Cells', Arterioscler Thromb Vasc Biol (2004); vol. 24; 294-300.

(Continued)

*Primary Examiner* — Noble Jarrell
*Assistant Examiner* — John S Kenyon
(74) *Attorney, Agent, or Firm* — Meaghan L. Richmond

(57) ABSTRACT

The invention concerns compounds of Formula (I)

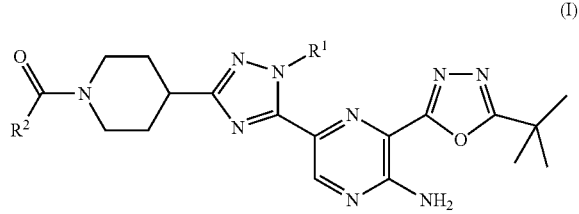

(I)

or pharmaceutically-acceptable salts thereof, wherein $R^1$ and $R^2$ have any of the meanings defined hereinbefore in the description; processes for their preparation, pharmaceutical compositions containing them and their use in the treatment of cell proliferative disorders.

12 Claims, 13 Drawing Sheets

(56) References Cited

FOREIGN PATENT DOCUMENTS

| WO | WO 2005/066156 A1 | 7/2005 |
|---|---|---|
| WO | WO 2005/121126 A1 | 12/2005 |
| WO | WO 2006/019833 A1 | 2/2006 |
| WO | WO 2006/034279 A1 | 3/2006 |
| WO | WO 2006/034315 A2 | 3/2006 |
| WO | WO 2006/034440 A2 | 3/2006 |
| WO | WO 2006/065601 A2 | 6/2006 |
| WO | WO 2006/084030 A2 | 8/2006 |
| WO | WO 2006/135627 A2 | 12/2006 |
| WO | WO 2007/096764 A2 | 8/2007 |
| WO | WO 2007/111904 A2 | 10/2007 |
| WO | WO 2007/147874 A1 | 12/2007 |
| WO | WO 2008/005937 A2 | 1/2008 |
| WO | WO 2008/011611 A2 | 1/2008 |
| WO | WO 2008/108448 B2 | 9/2008 |
| WO | WO 2009/021992 A2 | 2/2009 |
| WO | WO 2009/024825 A1 | 2/2009 |
| WO | WO 2009/053737 A2 | 4/2009 |
| WO | WO 2009/072621 B2 | 6/2009 |
| WO | WO 2009/079008 A1 | 6/2009 |
| WO | WO 2009/080705 A2 | 7/2009 |
| WO | WO 2009/157880 A1 | 12/2009 |
| WO | WO 2010/026121 A1 | 3/2010 |
| WO | WO 2010/029082 A1 | 3/2010 |
| WO | WO 2010/054398 A1 | 5/2010 |
| WO | WO 2010/071837 A1 | 6/2010 |
| WO | WO 2010/075376 A2 | 7/2010 |
| WO | WO 2010/086613 A1 | 8/2010 |
| WO | WO 2010/091808 A1 | 8/2010 |
| WO | WO 2010/091824 A1 | 8/2010 |
| WO | WO 2010/106457 A2 | 9/2010 |
| WO | WO 2010/139982 A1 | 12/2010 |
| WO | WO 2011/000905 A1 | 1/2011 |
| WO | WO 2011/025690 A1 | 3/2011 |
| WO | WO 2011/048082 A1 | 4/2011 |
| WO | WO 2011/076419 A1 | 6/2011 |
| WO | WO 2011/089400 A1 | 7/2011 |
| WO | WO 2011/095196 A1 | 8/2011 |
| WO | WO 2011/126903 A2 | 10/2011 |
| WO | WO 2011/133920 A1 | 10/2011 |
| WO | WO 2011/143426 A1 | 11/2011 |
| WO | WO 2012/003784 A1 | 1/2012 |
| WO | WO 2012/037226 A1 | 3/2012 |
| WO | WO 2012/068589 A2 | 5/2012 |
| WO | WO 2012/162635 A1 | 11/2012 |
| WO | WO 2013/049591 A2 | 4/2013 |
| WO | WO 2013/152298 A1 | 10/2013 |

OTHER PUBLICATIONS

Baade, 'One in four cancers preventable—but first we need the willpower', © Mar. 2012. Available from: <http:l/theconversation.com/one-in-four-cancers-preventable-but-first-we-need-the-will-power-5850 >.
Baldwin et al., '4-Trifluoromethylimidazoles and 5-(4-Pyridyl)-1,2,4-triazoles, New Classes of Xanthine Oxidase Inhibitors', J. Med. Chem. (1975); vol. 18; No. 9; 895-900.
Bi et al., 'Diaquabis[5-(pyrazin-2-yl-κ$N^1$)-3-(pyridin-4-yl)-1$H$-1,2,4-triazol-1-ido-κ$N^1$]cobalt(II) Methanol Disolvate', Acta Crystallographica, Section E: Structure Reports Online (2012); vol. 68; No. 5; m600.
Blume-Jensen and Hunter, 'Oncogenic Kinase Signalling', Nature (2001); vol. 411, 355-365.
Bock et al., 'Managing drug resistance in cancer: lessons from HIV therapy', Nature.com (Jul. 2012), vol. 12, 494-501.
Bradshaw, 'Cell Transformation: The Role of Oncogenes and Growth Factors', Mutagenesis (1986); vol. 1; No. 2; 91-97.
Browne et al., 'Ground- and Excited-State Electronic Structure of an Emissive Pyrazine-bridged Ruthenium(II) Dinuclear Complex', J. Amer. Chem. Soc. (2005); vol. 127; No. 4; 1229-1241.
Castillo et al., 'CAL-101: A Phosphatidylinositol-3-kinase p110-delta Inhibitor For The Treatment of Lymphoid Malignancies', Expert Opinion on Investigational Drugs (2012); vol. 21; No. 1; 15-22.

Courtney et al., 'The PI3K Pathway As Drug Target in Human Cancer', J Clin Oncol (2010); vol. 28; No. 6; 1075-1083.
Coussens and Werb, 'Inflammation And Cancer', Nature (2002); vol. 420; 860-867.
Dong et al., 'Unique 3D Co$^{II}$/Zn$^{II}$-coordination Polymers with (3,4,5)-connected Self-penetrating Topology: Synthesis, Topological Structures, Luminescent and Magnetic Properties', RSC Advances (2012); vol. 2; No. 30; 11219-11222.
Engelman et al., 'Effective Use of PI3K and MEK Inhibitors to Treat Mutant Kras G12D and PIK3CA H1047R Murine Lung Cancers', Nature Medicine (2008); vol. 14; 1351-1356.
Foster et al., 'The Phospoinositide (PI) 3-kinase Family', J Cell Science (2003); vol. 116; 3037-3040.
Garcia-Martinez et al., 'Effect of PI3K- and mTOR-specific Inhibitors on Spontaneous B-cell Follicular Lymphomas in PTEN/LKB1-deficient Mice', Br. J Cancer (2011); vol. 104; 1116-1125.
Harari et al., 'Molecular Mechanisms Underlying ErbB2/HER2 Action in Breast Cancer', Oncogene (2000); vol. 19; 6102-6114.
Hennessey et al., 'Exploiting The Pi3k/Akt Pathway For Cancer Drug Discovery', Nature Reviews Drug Discovery (2005); vol. 4; 988-1004.
Herman et al., 'Phosphatidylinositol 3-kinase-d Inhibitor CAL-101 Shows Promising Preclinical Activity In Chronic Lymphocytic Leukemia by Antagonizing Intrinsic and Extrinsic Cellular Survival Signals', Blood (2010); vol. 116; No. 12; 2078-2088.
Ihle et al., 'Mutations in the Phosphatidylinositol-3-Kinase Pathway Predict for Antitumor Activity of the Inhibitor PX-866 whereas Oncogenic Ras is a Dominant Predictor for Resistance', Cancer Research (2009); vol. 69; No. 1; 143-150.
Ikeda et al., 'PI3K/p110d Is A Novel Therapeutic Target in Multiple Myeloma', Blood (2010); vol. 116; No. 9; 1460-1468.
Janku et al., 'PIK3CA Mutations in Patients with Advanced Cancers Treated with PI3K/SKT/MTOR Axis Inhibitors', Molecular Cancer Therapeutics (2011); vol. 10; No. 3; 558-565.
Jiang et al., 'Synthesis and Cytotoxicity Evaluation of Novel Indolylpyrimidines and Indolylpyrazines and Potential Antitumor Agents', Bioorgan. & Med. Chem. (2001); vol. 9; 1149-1154.
Katso et al., 'Cellular Function Phosphoinositide 3-Kinases: Implications for Development, Immunity, Homeostasis, and Cancer', Annual Rev Cell Dev Biol (2001); vol. 17; 615-675.
Kauffmann-Zeh et al., 'Suppression of c-Myc-induced Apoptosis by Ras Signalling Through PI(3)K and PKB', Nature (1997); vol. 385; 544-548.
Koyasu, 'The Role of PI3K in Immune Cells', Nature Immunology (2003); vol. 4; 313-319.
Kuzmierkiewicz et al., 3,5-Disubstituted Derivatives of 1,2,4-Triazole Synthesis and Hypotensive Activity, Scientia Pharmaceutica (1985); vol. 53; No. 3; 133-138.
Li et al., 'Novel EGFR Inhibitors Prepared by Combination of Dithiocarbamic Acid Esters and 4-anilinoquinazolines', Bioorgan. & Med. Chem. Letters (2011); vol. 21; 3637-3640.
Ma et al., PIK3CA as an Oncogene in Cervical Cancer; Oncogene (2000); vol. 19; 2739-2744.
National Cancer Institute, 'Drugs Approved for Different Kinds of Cancer', © 2014. Available from: <http://www.cancer.gov/cancertopics/druginfo/drug-page-index/prin >.
National Cancer Institute, 'A to Z List of Cancer Drugs', © 2014. Available from: <http://www.cancer.gov/cancertopics/druginfo/alphalist/print >.
Nicholson and Anderson, 'The Protein Kinase B/Akt Signalling Pathway in Human Malignancy', Cellular Signalling (2002); vol. 14; 381-395.
Niraimathi et al., 'Synthesis, Characterisation and Evaluation of Biological Activity of Some 3, 5 Disubstituted 1h 1, 2, 4 Triazoles', Acta Ciencia Indica (2009); vol. 35; No. 1; 43-49.
Philp et al., 'The Phosphatidylinositol 3'-kinase p85α Gene Is an Oncogene in Human Ovarian and Colon Tumors', Cancer Research (2001); vol. 61; 7426-7429.
Prasad et al., 'Role of Phosphoinositide 3-Kinase in Cardiac Function and Heart Failure', TCM (2003); vol. 13; No. 5; 206-212.
Ranft et al., '$N^1$-Hetarylcarbonylsubstituierte Amidrazone und 3,5-disubstituierte 1,2,4-Triazole als Potentielle Antimycobakterielle Wirkstoffe', Pharmazie (2001); vol. 56; No. 3; 266.

(56) References Cited

OTHER PUBLICATIONS

Renne et al., 'High Expression of Several Tyrosine Kinases and Activation of The PI3K/AKT Pathway in Mediastinal Large B Cell Lymphoma Reveals Further Similarities to Hodgkin Lymphoma', Leukemia (2007); vol. 21; 780-787.

Rudelius et al., 'Constitutive Activation of Akt Contributes To The Pathogenesis and Survival of Mantle Cell Lymphoma', Blood (2006); vol. 108; No. 5; 1668-1676.

Samuels et al., 'Mutant PIK3CA Promotes Cell Growth and Invasion of Human Cancer Cells', Cancer Cell (2005); vol. 7; 561-573.

Samuels et al., 'High Frequency of Mutations of the PIK3CA Gene in Human Cancers', Scinece (2004); vol. 304; 554.

Sawyer, 'Cancer Metastasis Therapeutic Targets and Drug Discovery: Emerging Small-molecule Protein Kinase Inhibitors', Expert Opinion Investig Drugs (2004); vol. 13; No. 1; 1-19.

Shayesteh et al., 'PIK3CA is Implicated as an Oncogene in Ovarian Cancer', Nature Genetics (1999); vol. 21; 99-102.

Siu et al., 'The Design and Synthesis of Potent and Cell-active Allosteric Dual Akt 1 and 2 Inhibitors Devoid of hERG Activity', Bioorgan. & Med. Chem. Letters (2008); vol. 18; No. 4; 4191-4194.

Simpson and Parsons, 'PTEN: Life as a Tumor Suppressor', Experimental Cell Res. (2001); vol. 264; 29-41.

Uddin et al., 'Role of Phosphatidylinositol 3'-kinase/AKT Pathway in Diffuse Large B-cell Lymphoma Survival', Blood (2006); vol. 108; No. 13; 4178-4186.

Vanhaesebroeck et al., 'Phosphoinosltide 3-kinases: A Conserved Family of Signal Transducers', Trends in Biol Sci. (1997); vol. 22; 267-272.

Vara et al., 'PI3K/Akt Signalling Pathway and Cancer', Cancer Treatment Reviews (2004); vol. 30; 193-204.

Vivanco and Sawyers, 'The Phosphatidylinositol 3-Kinase-Akt Pathway In Human Cancer', Nature Reviews (2002); vol. 2; 469-501.

\* cited by examiner

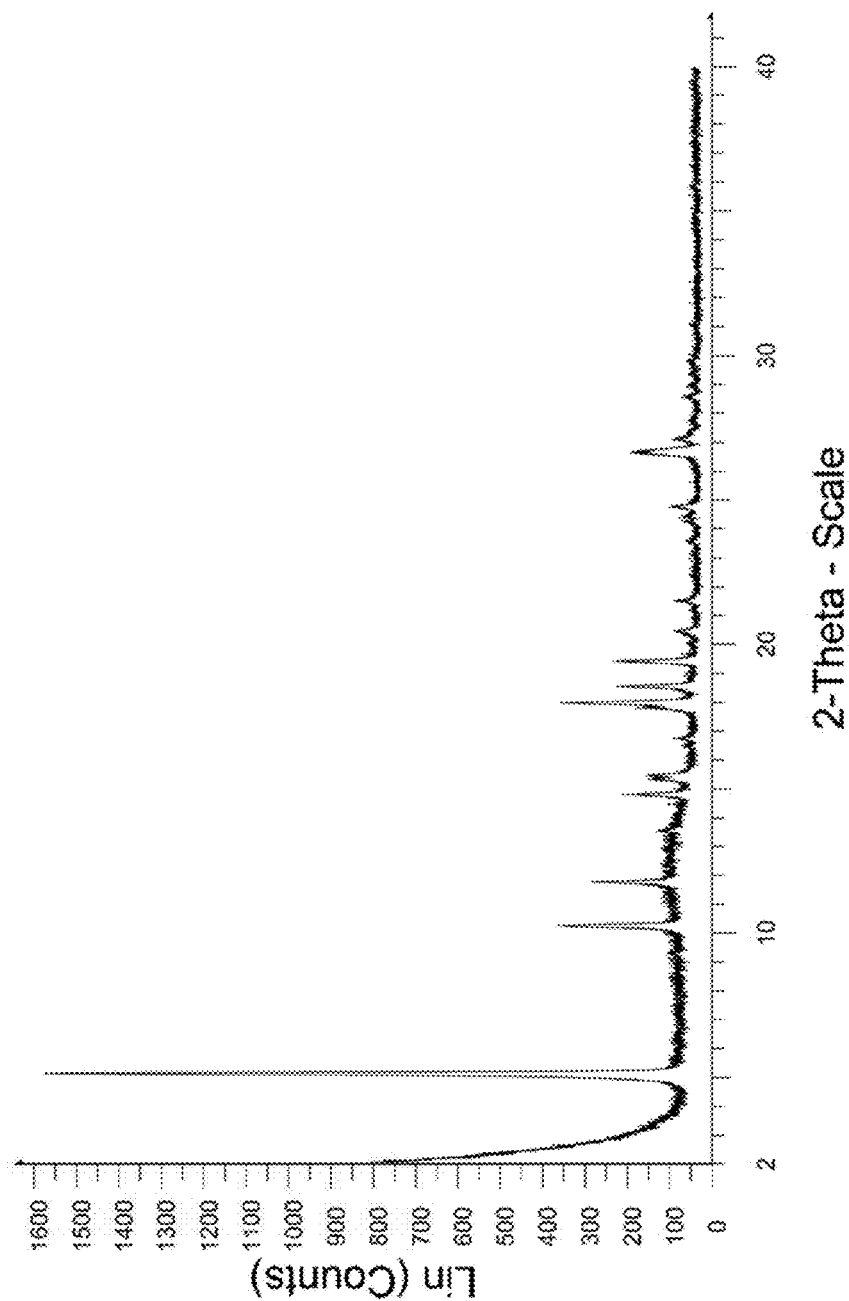
Figure 1: X-Ray Powder Diffraction Pattern Example 1 Form A

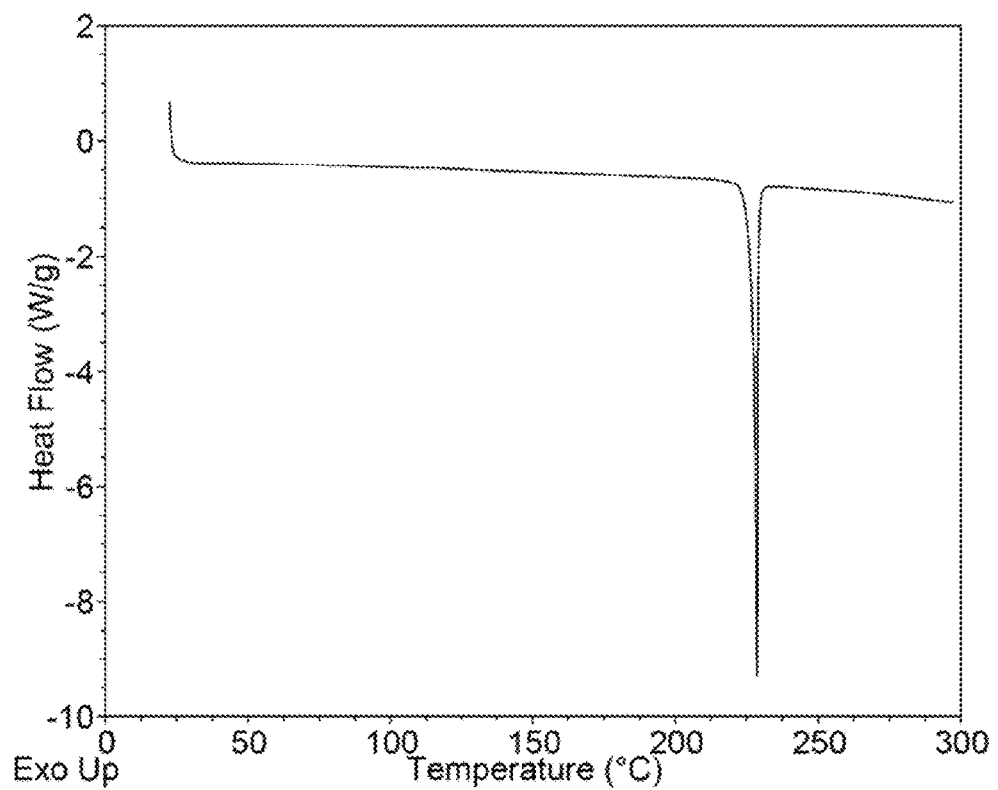
Figure 2: DSC Thermogram Example 1 Form A

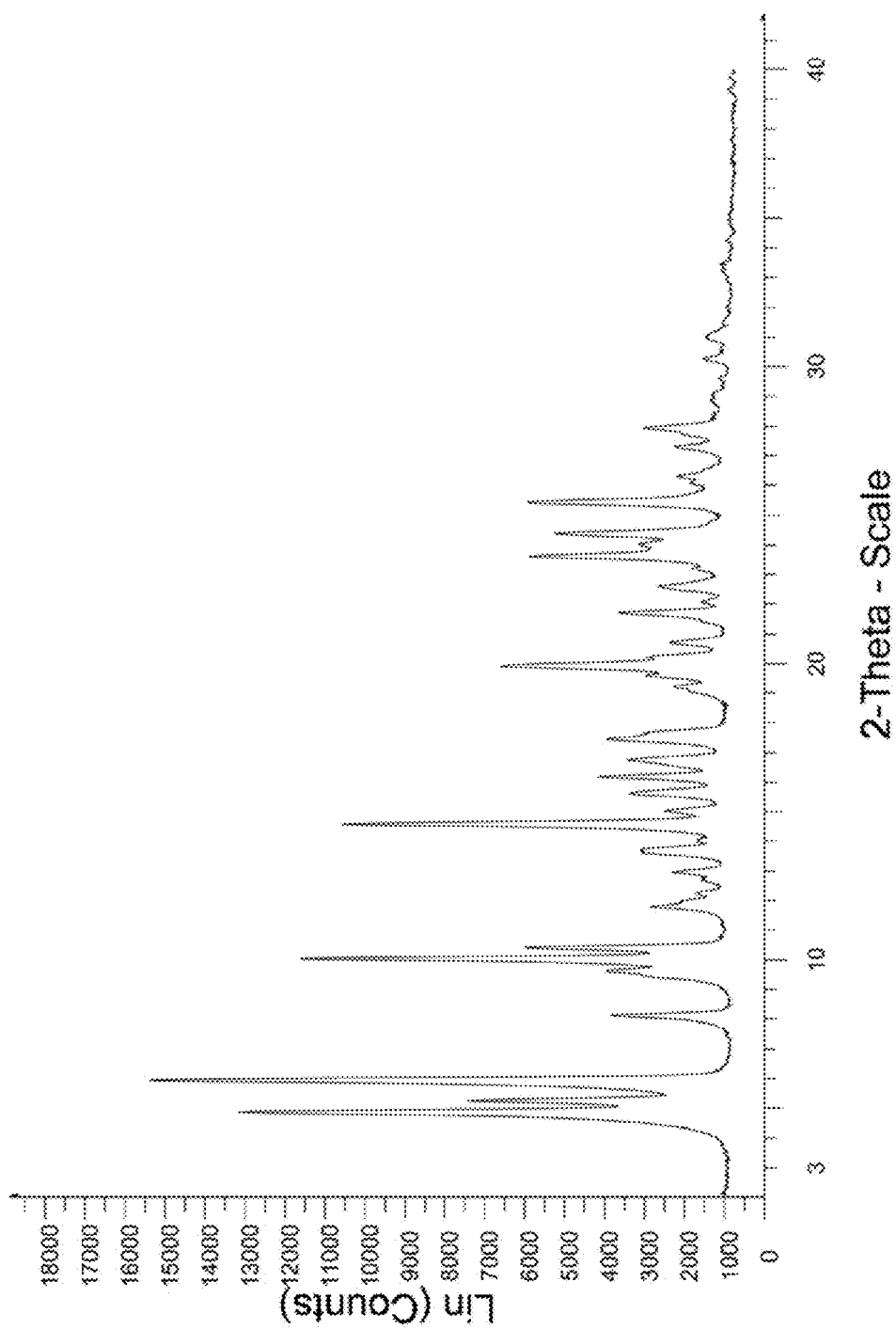
Figure 3: X-Ray Powder Diffraction Pattern Example 3 Form A

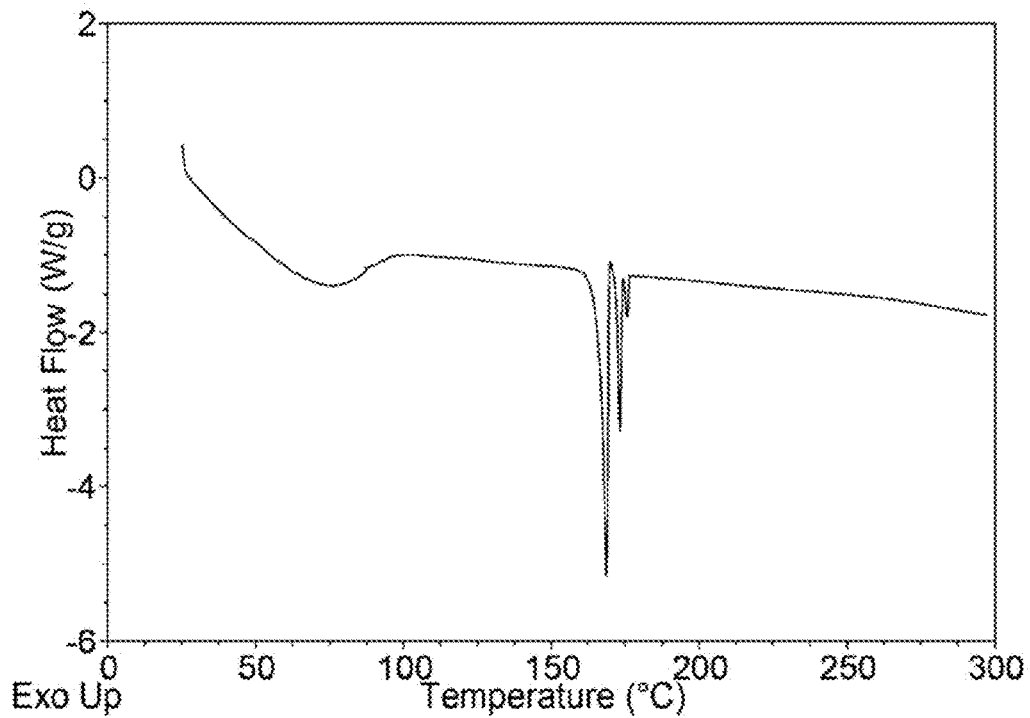
Figure 4: DSC Thermogram Example 3 Form A

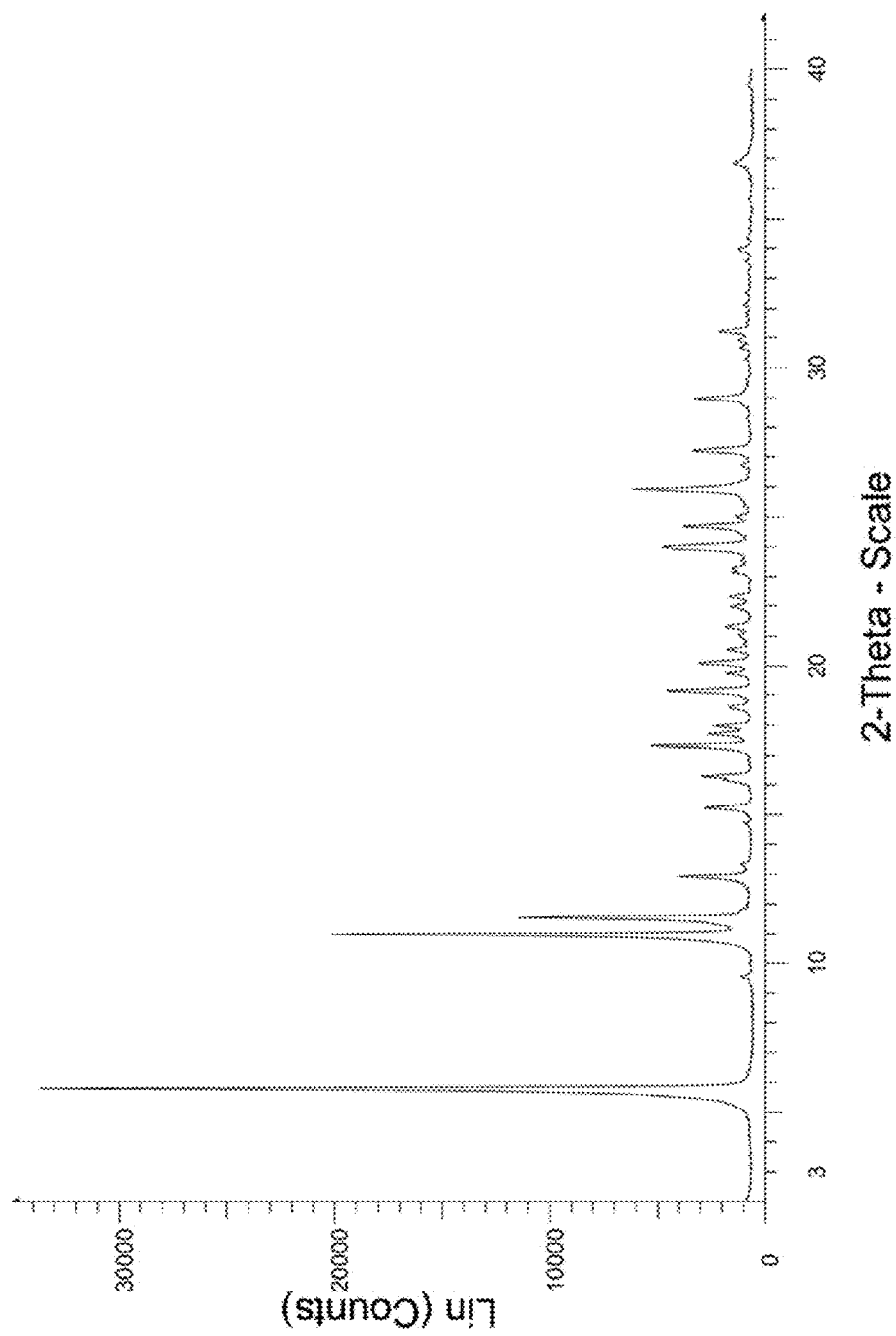
Figure 5: X-Ray Powder Diffraction Pattern Example 3 Form B

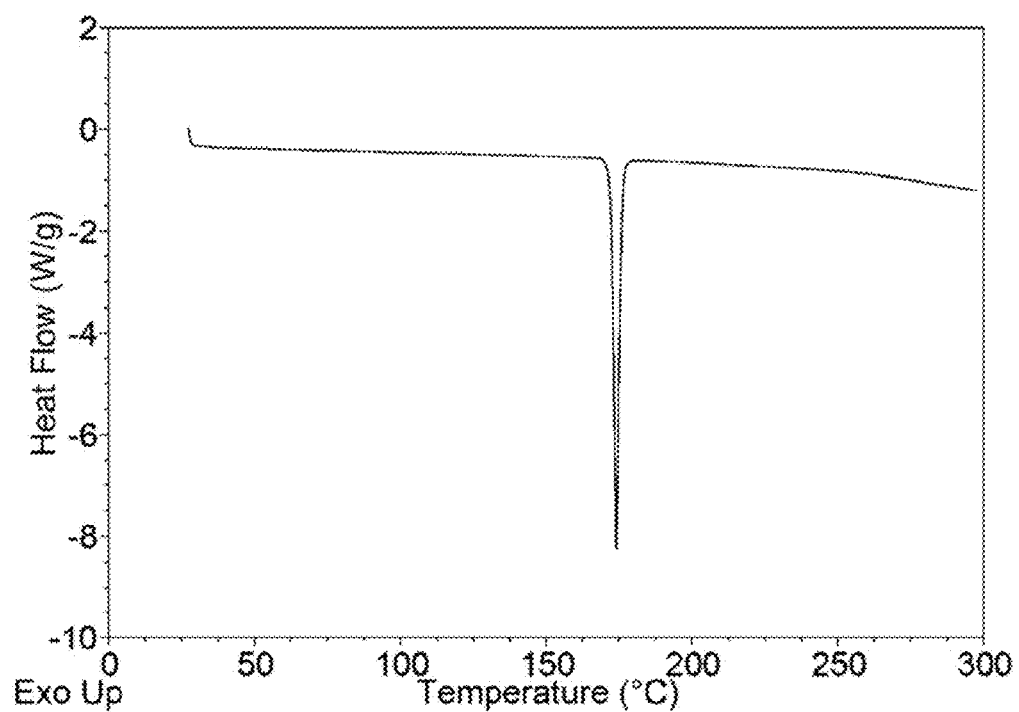
Figure 6: DSC Thermogram Example 3 Form B

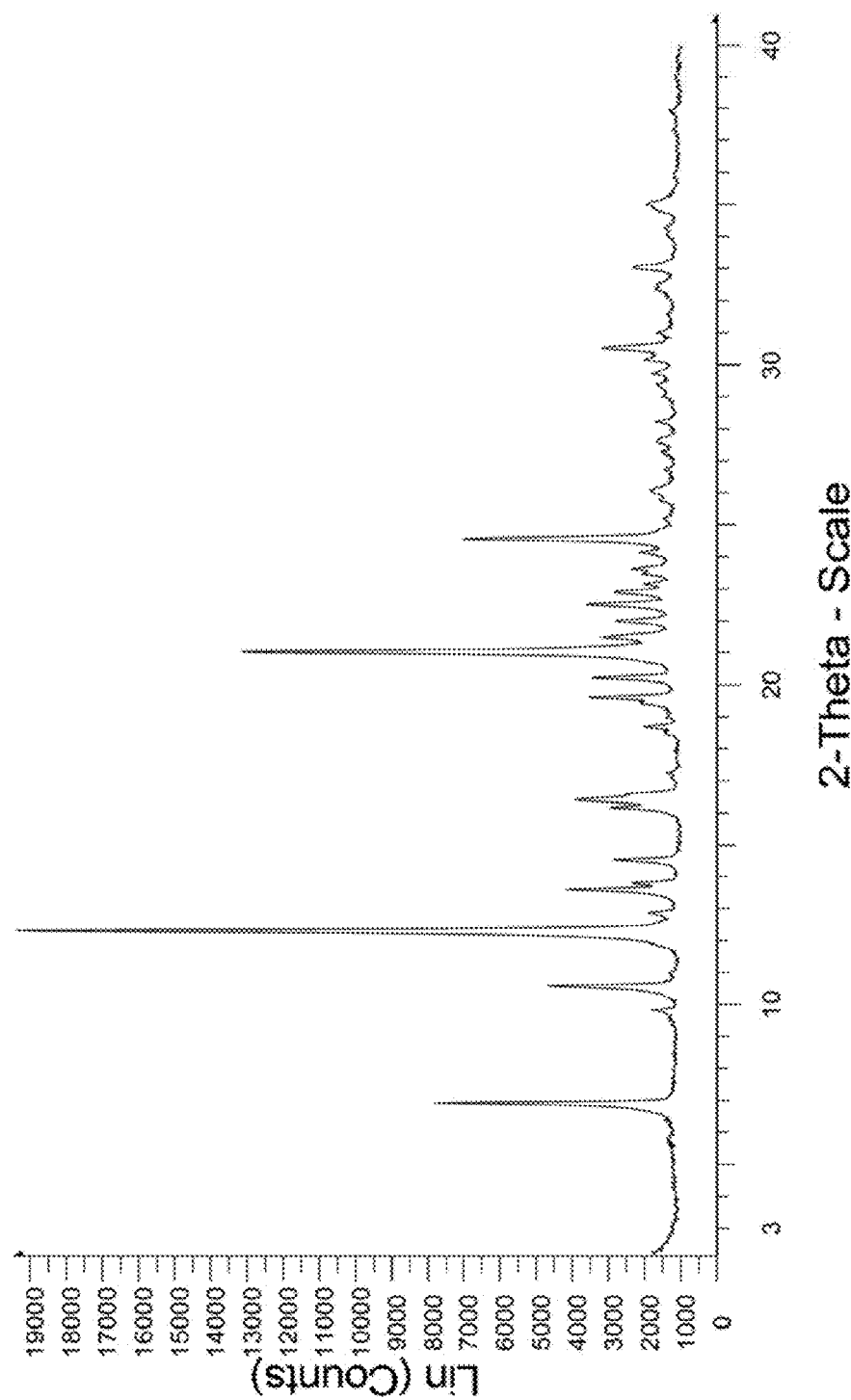
Figure 7. X-Ray Powder Diffraction Pattern Example 3 Form C

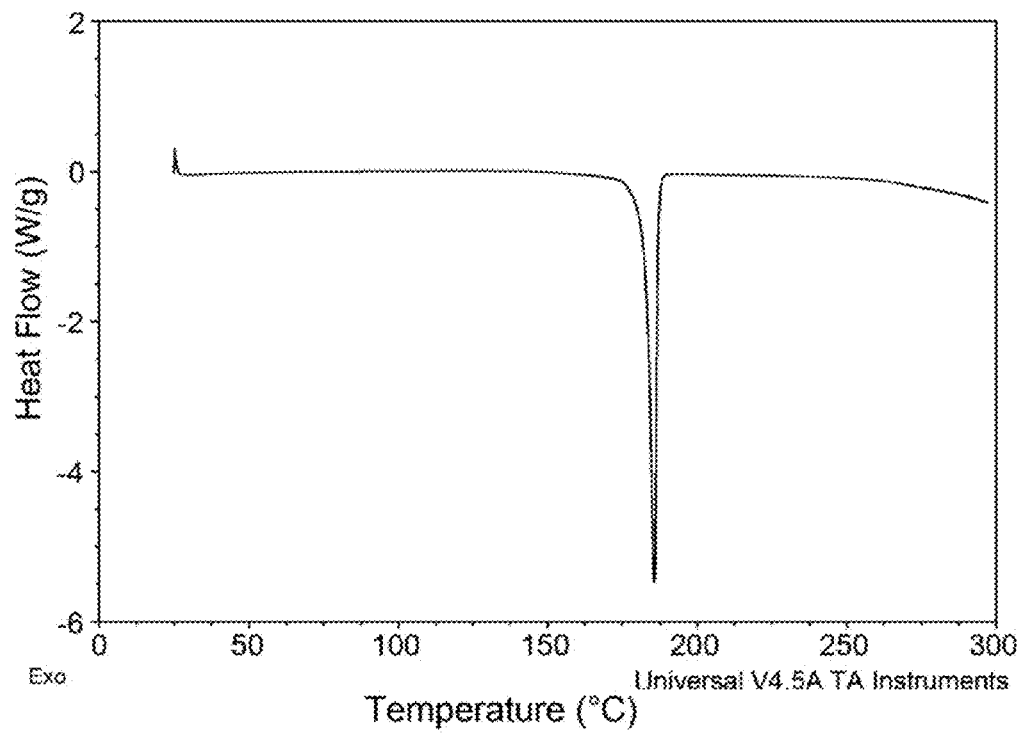
Figure 8: DSC Thermogram Example 3 Form C

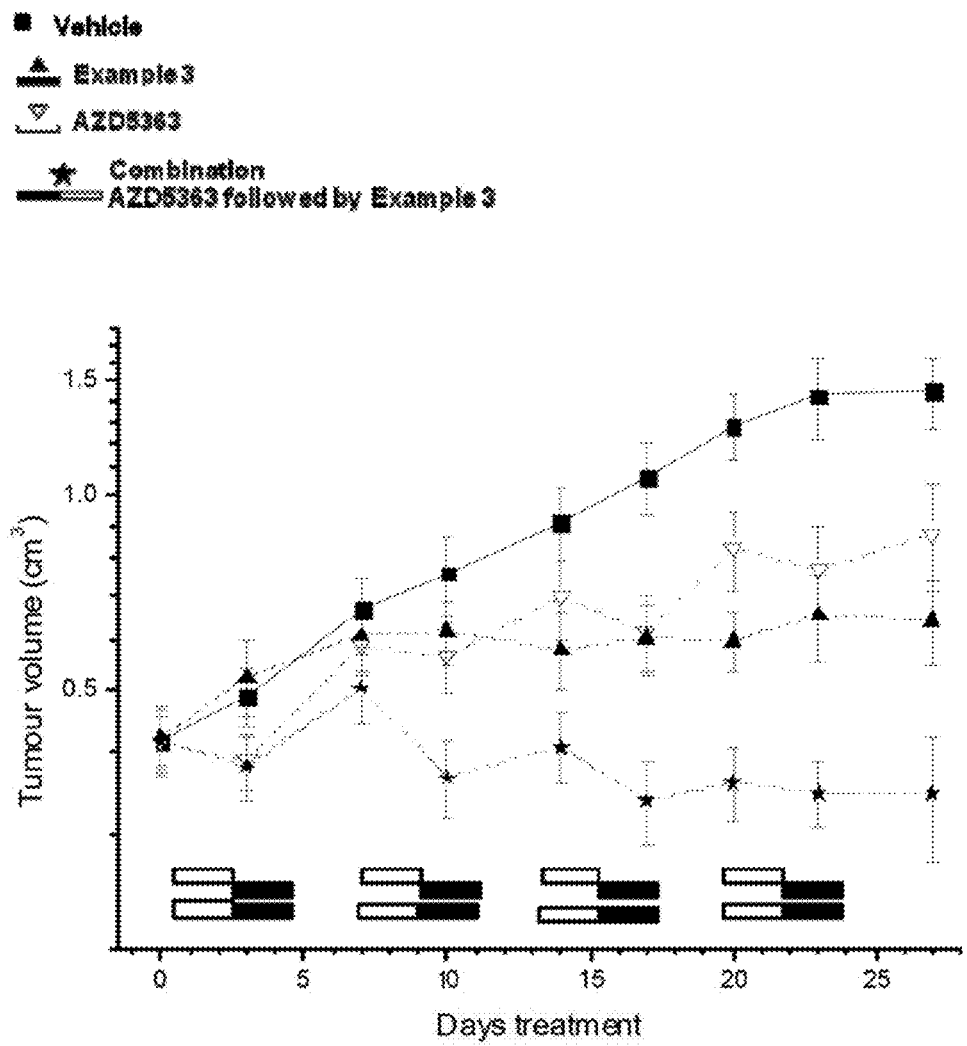
Figure 9: Tumour Growth Inhibition by Example 3 in Combination with AKT inhibitor (AZD5363) – sequential administration

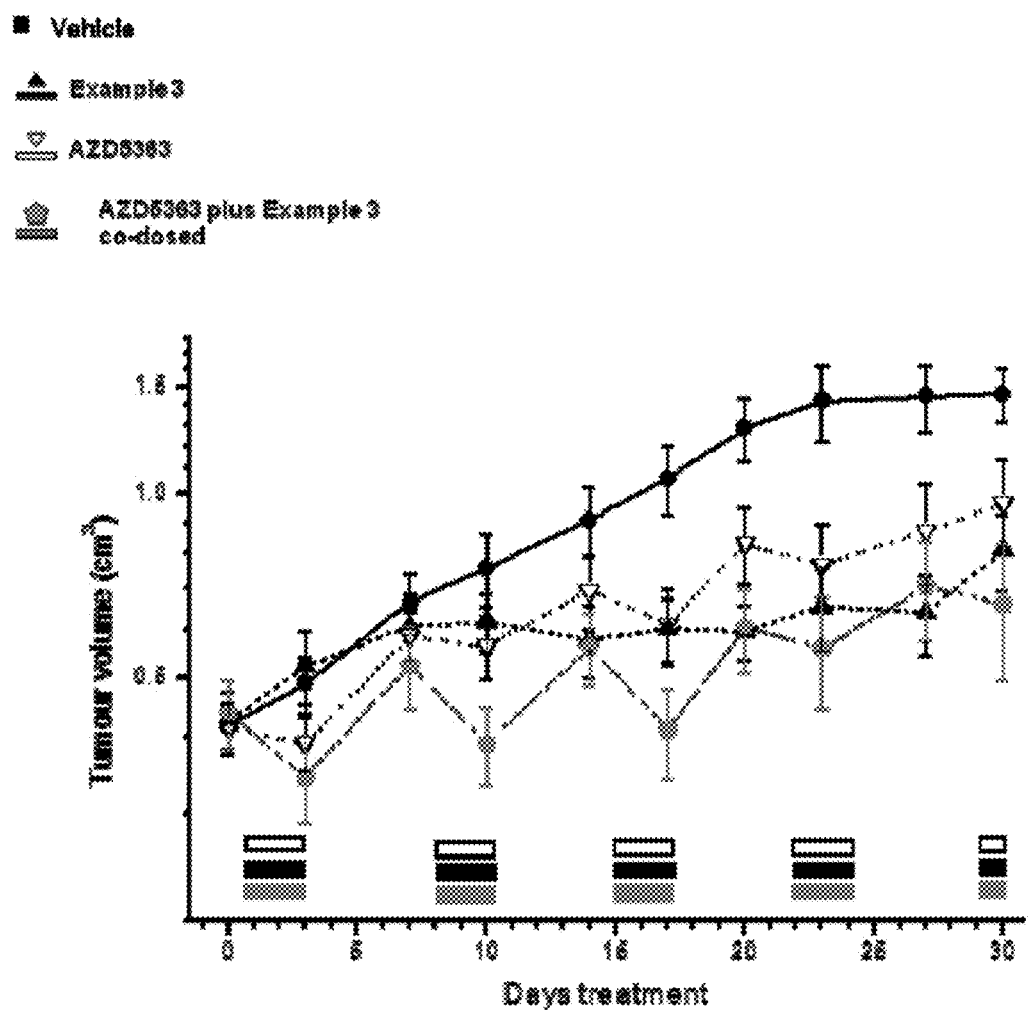
Figure 10; Tumour Growth Inhibition by Example 3 in Combination with AKT inhibitor (AZD5363), co-administration

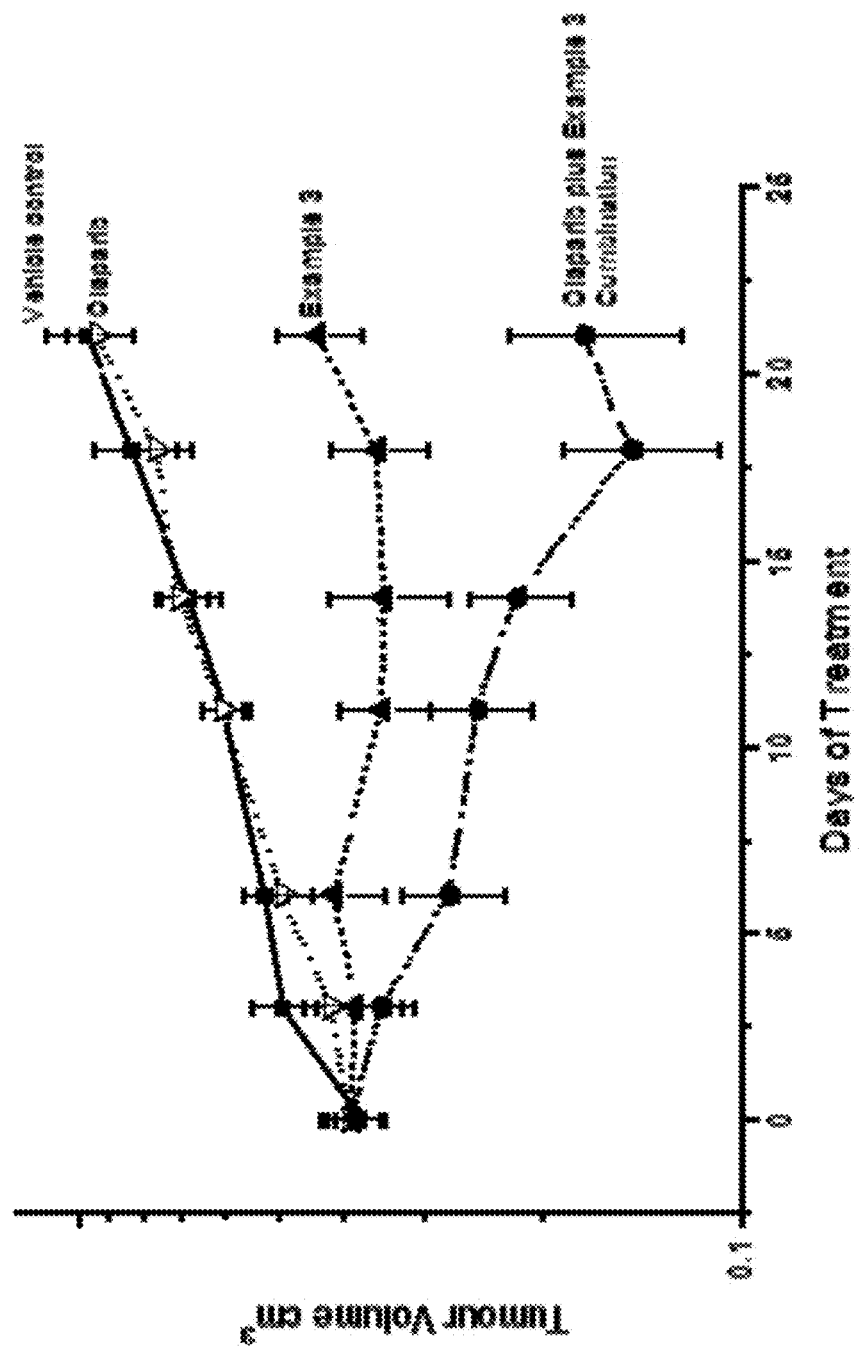
Figure 11: Tumour Growth Inhibition by Example 3 in Combination with PARP inhibitor (Olaparib) in BT474 xenograft model

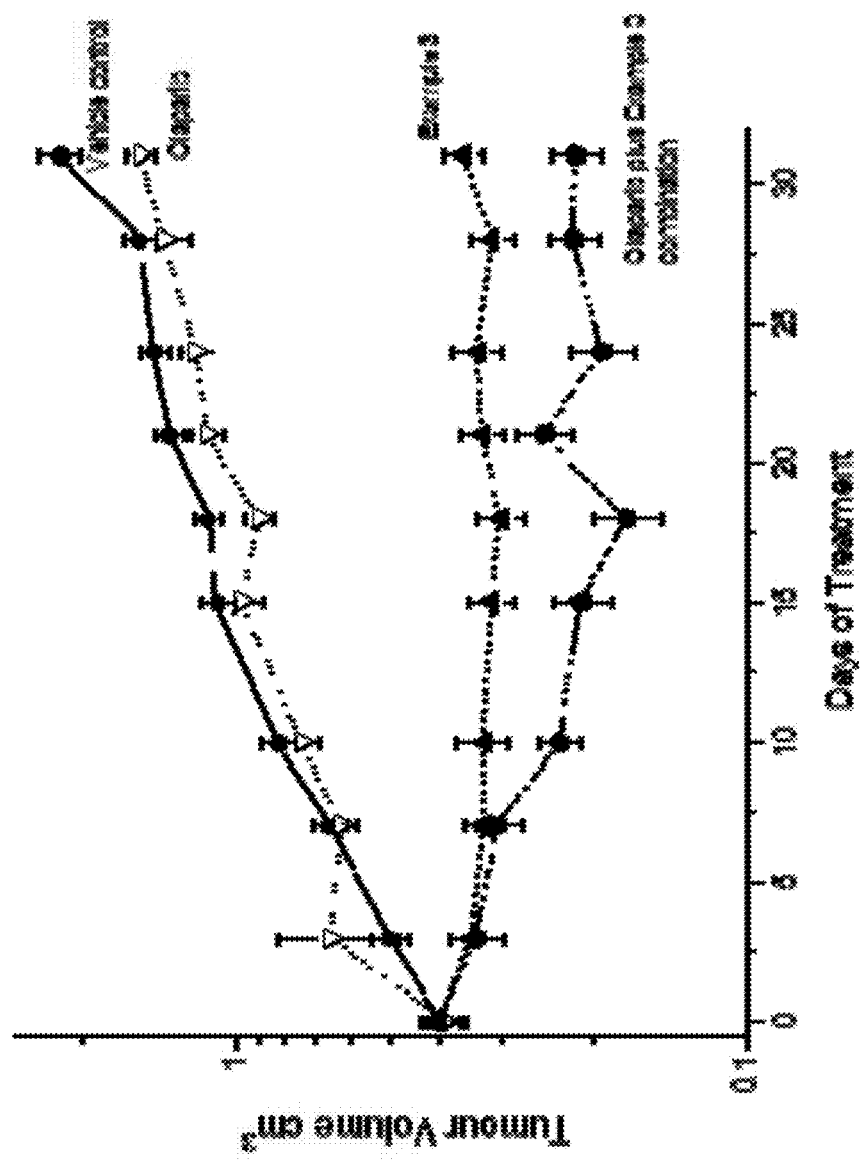
Figure 12: Tumour Growth Inhibition by Example 3 in Combination with PARP inhibitor (Olaparib) MCF7 xenograft model

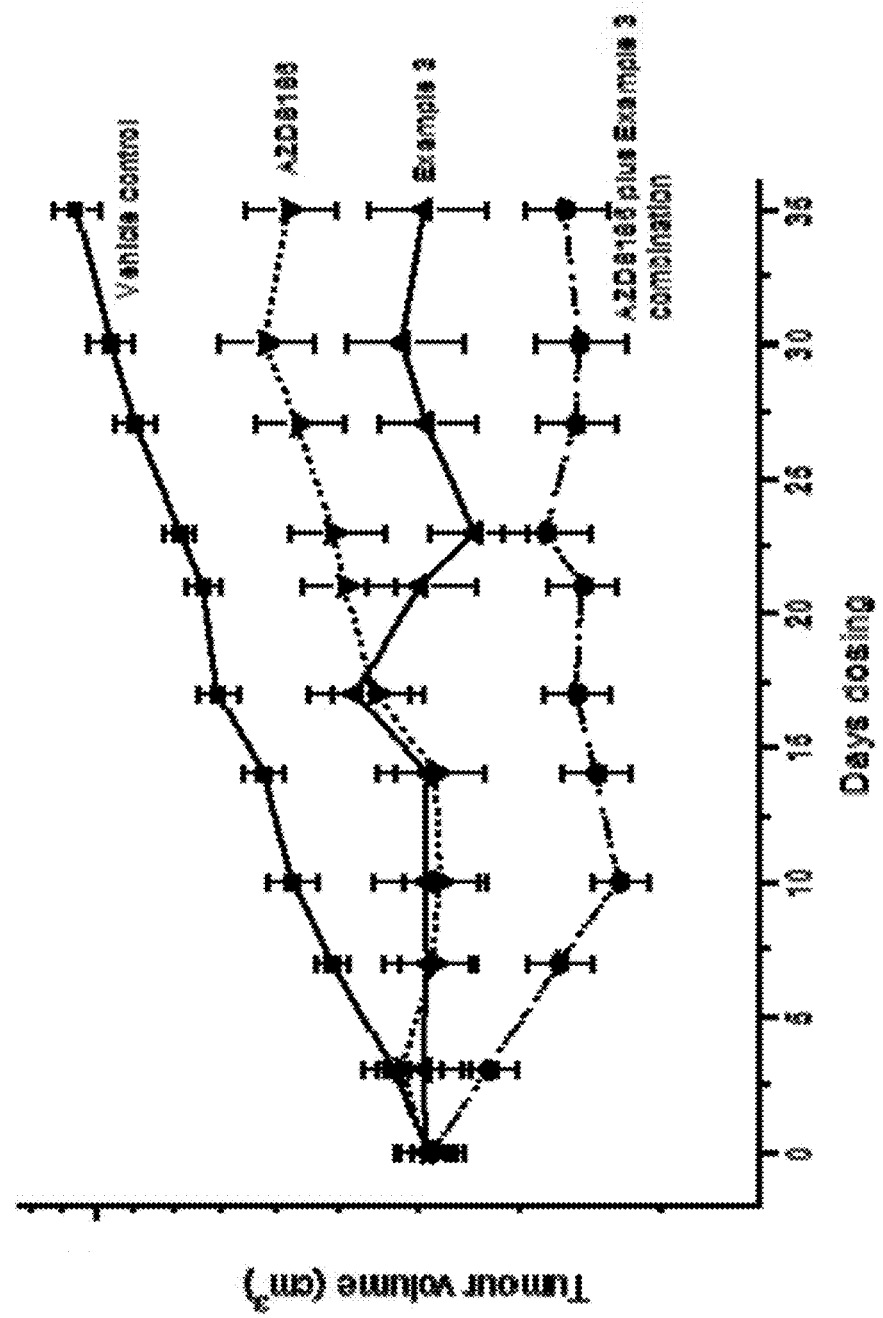
Figure 13: Tumour Growth Inhibition by Example 3 in Combination with AZD8186

CHEMICAL COMPOUNDS

This application is a continuation of U.S. patent application Ser. No. 14/160,650, filed Jan. 22, 2014, issuing, which claims the benefit under 35 U.S.C. §119(a)-(d) of Patent Application No. 13305078.1 (EP), filed Jan. 23, 2013.

The invention concerns certain novel aminopyrazine derivatives, or pharmaceutically-acceptable salts thereof, which possess anti-cancer activity and are accordingly useful in methods of treatment of the human or animal body. The invention also concerns processes for the manufacture of said aminopyrazine derivatives, pharmaceutical compositions containing them and their use in therapeutic methods, for example in the manufacture of medicaments for use in the prevention or treatment of cancers in a warm-blooded animal such as man, including use in the prevention or treatment of cancer.

The present invention also relates to aminopyrazine derivatives that are selective inhibitors of the PI3-kinase family of enzymes (which is alternatively known as the phosphatidylinositol-3-kinase family or PI3K family), particularly of PI3K-α and PI3K-δ isoforms, and are, for example, useful for anti-tumour therapy.

In the area of cancer it has in recent years been discovered that a cell may become cancerous by virtue of the transformation of a portion of its DNA into an oncogene, that is a gene which, on activation, leads to the formation of malignant tumour cells (Bradshaw, *Mutagenesis*, 1986, 1, 91). Several such oncogenes give rise to the production of peptides, which are Kinases, a class of enzymes that are capable of phosphorylating their protein or lipid substrates. There are several classes of kinases.

Firstly, tyrosine kinases, which may be receptor tyrosine kinases or non receptor tyrosine kinases. Various classes of receptor tyrosine kinases are known (Wilks, *Advances in Cancer Research*, 1993, 60, 43-73) based on families of growth factors, that can bind to the extracellular surface of different receptor tyrosine kinases; as an example the classification includes Class I receptor tyrosine kinases comprising the EGF family of receptor tyrosine kinases. Non-receptor tyrosine kinases are located intracellularly; various classes of non-receptor tyrosine kinases are known including the Src family such as the Src, Lyn, Fyn and Yes tyrosine kinases.

Secondly, certain kinases belong to the class of serine/threonine kinases which are also located intracellularly. Serine/threonine kinase signalling pathways include the Raf-MEK-ERK cascade and those downstream of PI3-kinase such as PDK-1, AKT and mTOR (Blume-Jensen and Hunter, *Nature*, 2001, 411, 355).

It is also known that certain other kinases belong to the class of lipid kinases, which are located intracellularly and are, as for the above mentioned kinases, involved in the transmission of biochemical signals such as those that influence tumour cell growth and invasiveness. Various classes of lipid kinases are known including the aforementioned PI3-kinase family.

It is now well understood that deregulation of oncogenes and tumour-suppressor genes contributes to the formation of malignant tumours, for example by way of increased cell proliferation or increased cell survival. It is also now known that signalling pathways mediated by the PI3-kinase family have a central role in a number of cell processes including proliferation and survival, and deregulation of these pathways is a causative factor across a wide spectrum of human cancers and other diseases (Katso et al., *Annual Rev. Cell Dev. Biol.*, 2001, 17: 615-617 and Foster et al., *J. Cell Science*, 2003, 116: 3037-3040).

The PI3-kinase family of lipid kinases is a group of enzymes that phosphorylate the 3-position of the inositol ring of phosphatidylinositol (PI). Three major groups of PI3-kinase enzymes are known which are classified according to their physiological substrate specificity (Vanhaesebroeck et al., *Trends in Biol. Sci.*, 1997, 22, 267; Engleman et al., *Nature Review Genetics*, 2006, 7, 607). Class III PI3-kinase enzymes phosphorylate PI alone. In contrast, Class II PI3-kinase enzymes phosphorylate both PI and PI4-phosphate [abbreviated hereinafter to PI(4)P]. Class I PI3-kinase enzymes phosphorylate PI, PI(4)P and PI4,5-bisphosphate [abbreviated hereinafter to PI(4,5)P2], although only PI(4,5)P2 is believed to be the physiological cellular substrate. Phosphorylation of PI(4,5)P2 produces the lipid second messenger PI3,4,5-triphosphate [abbreviated hereinafter to PI(3,4,5)P3]. More distantly related members of this superfamily are Class IV kinases such as mTOR and DNA-dependent protein kinase that phosphorylate serine/threonine residues within protein substrates. The most studied and understood of these lipid kinases are the Class I PI3-kinase enzymes.

Class I PI3-kinases are heterodimers consisting of a p110 catalytic subunit and a regulatory subunit, and the family is further divided into Class Ia and Class Ib enzymes on the basis of regulatory partners and mechanism of regulation (Engleman et al., *Nature Review Genetics*, 2006, 7, 607). Class Ia enzymes consist of three distinct catalytic subunits (p110α, p110β and p110δ, by nomenclature define the PI3-Kinase isoform as α, β or δ respectively) that dimerise with five distinct regulatory subunits (p85α, p55α, p50α, p85β and p55γ), with all catalytic subunits being able to interact with all regulatory subunits to form a variety of heterodimers. Class Ia PI3-kinase enzymes are generally activated in response to growth factor-stimulation of receptor tyrosine kinases, via interaction of the regulatory subunit SH2 domains with specific phospho-tyrosine residues of the activated receptor or adaptor proteins such as IRS-1. Both p110α and p110β are widely expressed across cell types and tissues, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems as well as by the mechanisms described above.

There is now considerable evidence indicating that Class Ia PI3-kinase enzymes, contribute to tumourigenesis in a wide variety of human cancers, either directly or indirectly (Vivanco and Sawyers, *Nature Reviews Cancer*, 2002, 2, 489-501). In particular, the PIK3CA gene which encodes the p110α catalytic subunit of PI3-kinase is widely implicated in tumourigenesis. Activating point mutations, most frequently found in the helical or catalytic domains of p110α, increase the PI3-kinase activity of the holoenzyme and can transform cells. They have been reported, particularly, as somatically occurring mutations at significant frequencies across a wide range of tumour types (Samuels et al., *Science*, 2004, 304, 554; Samuels et al., *Cancer Cell*, 2005, 7, 561; Engleman et al., *Nature Review Genetics*, 2006, 7, 607; Zhao L and Vogt P K, *Oncogene* 2008, 27 5486). Tumour-related mutations in p85α have also been identified in cancers such as those of the ovary and colon (Philp et al., *Cancer Research*, 2001, 61, 7426-7429). Furthermore, the p110α subunit is amplified in some tumours such as those of the ovary (Shayesteh et al., *Nature Genetics*, 1999, 21, 99-102) and cervix (Ma et al., *Oncogene*, 2000, 19, 2739-2744).

In addition to direct effects, it is believed that activation of Class Ia PI-3 kinase contributes to tumourigenic events that occur upstream in signalling pathways, for example by way of ligand-dependent or ligand-independent activation of receptor tyrosine kinases, GPCR systems or integrins (Vara et al., *Cancer Treatment Reviews*, 2004, 30, 193-204). Examples of such upstream signalling pathways include over-expression of the receptor tyrosine kinase Erb2 in a variety of tumours leading to activation of PI 3-kinase-mediated pathways (Harari et al., *Oncogene*, 2000, 19, 6102-6114) and over-expression of the oncogene Ras (Kauffmann-Zeh et al., *Nature*, 1997, 385, 544-548). In addition, Class Ia PI3-kinases may contribute to tumourigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI3-kinase-mediated production of PI(3,4,5)P3 (Simpson and Parsons, *Exp. Cell Res.*, 2001, 264, 29-41). Furthermore, augmentation of the effects of other PI3-kinase-mediated signalling events is believed to contribute to a variety of cancers, for example by activation of Akt (Nicholson and Anderson, *Cellular Signalling*, 2002, 14, 381-395).

Hence the common deregulation of PI3-kinase together with those of upstream and downstream signalling pathways collectively make it one of the most commonly deregulated pathways in human cancer (Hennessey et al., *Nature Reviews Drug Discovery*, 2005, 4, 988).

In addition to a role in mediating proliferative and survival signalling in tumour cells, there is also good evidence that Class Ia PI3-kinase enzymes will also contribute to tumourigenesis via its function in tumour-associated stromal cells. For example, PI3-kinase signalling is known to play an important role in mediating angiogenic events in endothelial cells in response to pro-angiogenic factors such as VEGF (Abid et al., *Arterioscler. Thromb. Vasc. Biol.*, 2004, 24, 294-300). As Class I PI3-kinase enzymes are also involved in motility and migration (Sawyer, *Expert Opinion Investig. Drugs*, 2004, 13, 1-19), PI3-kinase inhibitors should provide therapeutic benefit via inhibition of tumour cell invasion and metastasis.

In addition, Class I PI3-kinase enzymes play an important role in the regulation of immune cells with PI3-kinase activity contributing to pro-tumourigenic effects of inflammatory cells (Coussens and Werb, *Nature*, 2002, 420, 860-867). Indeed, the Class Ia PI3-kinase enzyme, PI3-kinase δ, is particularly implicated in tumourigenesis in haematological malignancies, such as Chronic Lymphoctyic Leukaemia (CLL), Acute Lymphoblastic Leukaemia (ALL) and Mantle Cell Lymphoma (MCL). Elevated-signalling of PI3K (mainly p110δ) is reported in a wide range of malignant lymphoid cells (Herman et al., *Blood* 2010, 116. 2078; Ikeda et al., *Blood*, 2010, 116, 1460; Uddin et al., *Blood*, 2006, 108, 4178; Rudelius et al., *Blood* 2006, 108, 1668; Garcia-Martinez., *Br J Cancer*, 2011, 104, 1116; Renne et al., *Leukemia*, 2007, 2, 780). This has led to the development of agents targeting PI3-kinase δ, with promising initial clinical results in haematological malignancies. (Castillo et al., *Expert Opinion on Investigational Drugs*, 2012, 21, 15).

These findings suggest that pharmacological inhibitors of Class I PI3-kinase enzymes should be of therapeutic value for treatment of the various forms of the disease of cancer comprising solid tumours such as carcinomas and sarcomas and the leukaemias and lymphoid malignancies.

Early studies, both pre-clinical and clinical, exploring the physiological and pathological roles of the PI3-kinase enzyme, have largely used agents with limited kinase inhibition selectivity, either stretching across the wider kinase families, across the PI3-kinase family, or across the PI3-kinase Class 1 family. Hence, there is a need for more selective pharmaceutical PI3-kinase Class 1 inhibitors to provide useful therapeutic agents with potential to deliver an improved therapeutic margin over the initial agents that entered the clinic.

Generally, the compounds of the present invention possess potent inhibitory activity against a subset of Class I PI3-kinase enzymes, particularly against Class Ia PI3-kinase-α and -δ isoforms, with relative sparing of the -γ and particularly the -β isoform. The compounds are also selective against wider PI3-kinase family and the wider kinome. Such compounds possess sufficient potency against Class I PI3-kinase enzymes that they may be used in an amount sufficient to inhibit a subset of Class IPI 3-kinase isoforms, particularly to inhibit Class Ia PI3-kinase enzymes-α and -δ, whilst demonstrating little activity against other kinases.

The understanding of the deregulation of PI3-kinase signalling in human cancer and other diseases offers the prospect of targeting a subset of patients most likely to benefit from treatment of the agents described in this patent, through a process known as Personalised Healthcare (PHC) or Personalised Medicine. For these agents, patients whose disease depends on elevated or otherwise altered PI3K-α signalling and/or PI3K-δ signalling may particularly benefit from treatment. It is well known in the art that diagnostics can be used to provide a response-prediction biomarker readout. Such diagnostics could measure one or more readouts of pathway deregulation such as, but not restricted to, mutation in the PIK3CA, PTEN or p85 (PIK3R) genes, amplification or increased copy number of the PIK3CA gene, overexpression or elevated activity of the PI3K-α and/or -δ isoform, or use of a phosphobiomarker readout within the pathway such as phospho-RTK or phospho-AKT. In addition, the measurement of mutation status or activation status of additional genes, such as Kras, a potential marker of resistance in tumours with aberrant or deregulated PIK3CA or PI3K-α (Engelman et al., *Nature Medicine*, 2008 14, p1351-1355; Ihle et al., *Cancer Research*, 2009, 69, p143-160; Janku et al., *Molecular Cancer Therapeutics*, 2011, 10, p558-564), could help increase the predictivity of a Personalised Medicine approach. Alternatively, in another targeted but less specific approach, the treatment could be focused in disease subsets where the deregulation of the relevant PI3K isoforms is known to be most prevalent.

The compounds described could be used to target disease, either alone or in combination with another pharmaceutical agent or agents. Combining PI3-kinase inhibitors with other therapies may improve efficacy by overcoming resistance mechanisms, either innate, or induced in response to the PI3-kinase agent. There is substantial pre-clinical data to support such an approach (Courtney et al, *J Clin Oncol*, 2010, 28, 1075; Engleman et al., *Nature Review Genetics*, 2006, 7, 607). One approach is 'intra-pathway' combinations with agents modulating other axes in the PI3-kinase signalling pathways (e.g. mTOR, AKT, RTK, other PI3-kinase agent). A second approach is 'inter-pathway' combinations where inhibition of more than one signalling pathway may be beneficial over inhibition of a single pathway (e.g. combined with MEK inhibitors, Raf inhibitors, Bcl family modulators, RTK inhibitors or DNA damage signalling modulators such as PARP inhibitors). Other approaches include where the PI3-kinase inhibitor is combined with agents or regimens that are already established in clinical practice, so called Standard of Care (SoC) approaches, or combinations with agents targeting non tumour cell mechanisms such as tumour stromal cell or via the immune system.

In addition to tumourigenesis, there is evidence that Class I PI3-kinase enzymes play a role in other diseases (Wymann et al., *Trends in Pharmacological Science*, 2003, 24, 366-376). Both Class Ia PI3-kinase enzymes, particularly PI3K-δ, and the single Class Ib enzyme (PI3K-γ) have important roles in cells of the immune system (Koyasu, *Nature Immunology*, 2003, 4, 313-319) and thus they are therapeutic targets for inflammatory and allergic indications. Inhibition of PI3-kinase is also, as described earlier, useful to treat cardiovascular disease via anti-inflammatory effects or directly by affecting cardiac myocytes (Prasad et al., *Trends in Cardiovascular Medicine*, 2003, 13, 206-212). Thus inhibitors of Class I PI3-kinase enzymes may be of value in the prevention and treatment of a wide variety of diseases in addition to cancer.

The compounds, i.e. the aminopyrazine derivatives, of the invention have been found to possess potent anti-tumour activity, being useful in inhibiting the uncontrolled cellular proliferation which arises from malignant disease. Without wishing to imply that the compounds disclosed in the present invention possess pharmacological activity only by virtue of an effect on a single biological process, it is believed that the compounds provide an anti-tumour effect by way of inhibition of Class I PI3-kinase enzymes, particularly by way of inhibition of a subset of the Class Ia PI3-kinase enzymes, more particularly by way of inhibition of the PI3K-α and -δ isoforms.

The compounds of the present invention may also be useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, benign prostatic hypertrophy (BPH), hypersensitivity reactions of the skin, blood vessel diseases (for example atherosclerosis and restenosis), allergic asthma, insulin-dependent diabetes, diabetic retinopathy and diabetic nephropathy.

Proline amides have been disclosed as selective PI3K-α selective agents by Novartis in International Patent Applications WO2009/080705, WO2010/029082 and WO2011/000905. Aminopyrazine containing ATR kinase inhibitors have been disclosed in WO2011/143426 and WO2010/071837 (Vertex).

According to one aspect of the invention there is provided a compound of the Formula (I)

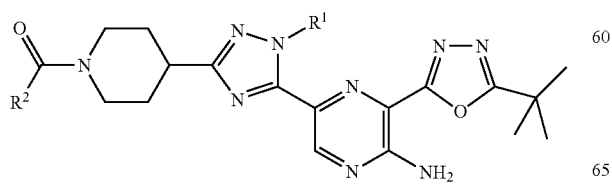

(I)

wherein:
$R^1$ is methyl or ethyl; and
$R^2$ is (C2-3)alkyl substituted by hydroxyl;
or a pharmaceutically-acceptable salt thereof.

In another aspect of the invention, there is provided a compound of Formula (I) as defined above.

It will be understood that the term "(C2-3)alkyl substituted by hydroxy" includes both straight chain and branched alkyl groups, for example those illustrated as groups (i) to (xi) below:

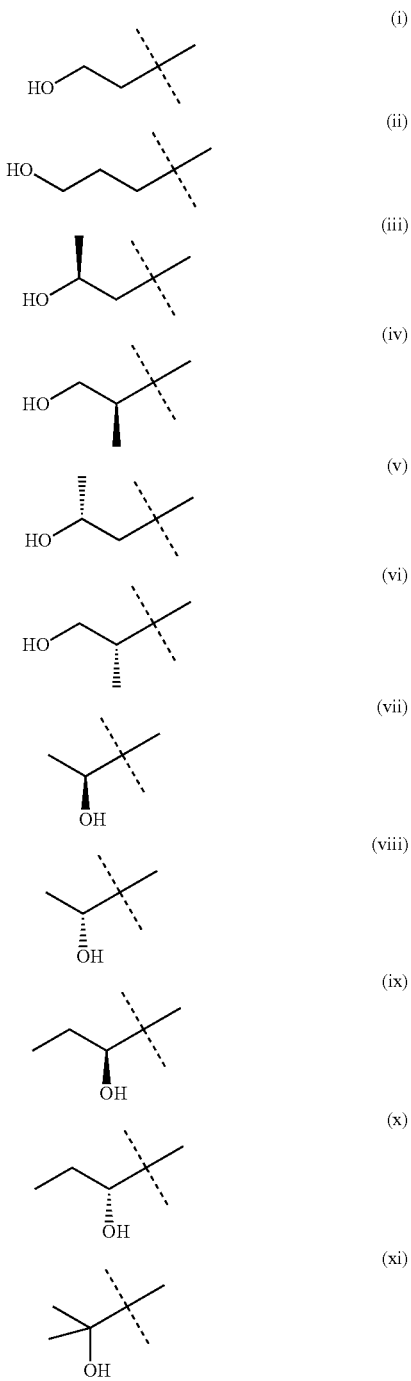

It is to be understood that, insofar as certain of the compounds of Formula (I) defined above may exist in optically active or racemic forms by virtue of one or more asymmetric carbon atoms, the invention includes in its definition any such optically active or racemic form which possesses PI3K-α and -δ inhibitory activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques.

A particular enantiomer of a compound described herein may be more active that other enantiomers of the same compound.

According to a further aspect of the invention there is provided a compound of the Formula (I), or a pharmaceutically-acceptable salt thereof, which is a single enantiomer being in an enantiomeric excess (% ee) of ≥95, ≥98% or ≥99%. Conveniently, the single enantiomer is present in an enantiomeric excess (% ee) of ≥99%.

According to a further aspect of the invention there is provided a pharmaceutical composition, which comprises a compound of the Formula (I), which is a single enantiomer being in an enantiomeric excess (% ee) of ≥95, ≥98% or ≥99% or a pharmaceutically-acceptable salt thereof, in association with a pharmaceutically-acceptable diluent or carrier. Conveniently, the single enantiomer is present in an enantiomeric excess (% ee) of ≥99%.

Some compounds of Formula (I) may be crystalline and may have more than one crystalline form. It is to be understood that the present invention encompasses any crystalline or amorphous form, or mixtures thereof, which form possesses properties useful in the inhibition of PI3K-α and -δ activity, it being well known in the art how to determine efficacy of a crystalline or amorphous form for the inhibition of PI3K-α and/or -δ activity by the standard tests described hereinafter.

It is generally known that crystalline materials may be analysed using conventional techniques such as X-Ray Powder Diffraction (hereinafter XRPD) analysis, Differential Scanning Calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

As an example, the compound of Example 1 exhibits crystallinity and one crystalline form has been identified.

Accordingly, a further aspect of the invention is Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one.

According to a further aspect of the present invention, there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with at least one specific peak at about 2-theta=5.1°.

According to a further aspect of the present invention, there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with at least one specific peak at about 2-theta=18.0°.

According to a further aspect of the present invention, there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with at least two specific peaks at about 2-theta=5.1 and 18.0°.

According to a further aspect of the present invention there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with specific peaks at about 2-theta=5.1, 18.0, 10.2, 11.7, 19.4, 18.5, 14.8, 26.7, 26.6, 17.8°.

According to the present invention there is provided crystalline form, Form A which has an X-ray powder diffraction pattern substantially the same as the X-ray powder diffraction pattern shown in FIG. 1.

According to a further aspect of the present invention, there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with at least one specific peak at about 2-theta=5.1° plus or minus 0.2° 2-theta.

According to a further aspect of the present invention, there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with at least one specific peak at about 2-theta=18.0° plus or minus 0.2° 2-theta.

According to a further aspect of the present invention, there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with at least two specific peaks at about 2-theta=5.1 and 18.0° plus or minus 0.2° 2-theta.

According to a further aspect of the present invention there is provided a crystalline form, Form A of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one, which has an X-ray powder diffraction pattern with specific peaks at about 2-theta=5.1, 18.0, 10.2, 11.7, 19.4, 18.5, 14.8, 26.7, 26.6, 17.8° plus or minus 0.2° 2-theta.

Example 3 is also crystalline and three forms (A, B and C) are described herein.

According to the present invention there is provided a crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at about 2-theta=4.8°.

According to the present invention there is provided a crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at about 2-theta=10.0°.

According to the present invention there is provided a crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least two specific peaks at about 2-theta=4.8° and 10.0°.

According to the present invention there is provided a crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with specific peaks at about 2-theta=4.8, 10.0, 14.6, 5.2, 19.9, 10.4, 25.4, 23.6, 24.4, 16.2°.

According to the present invention there is provided crystalline form, Form A of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern substantially the same as the X-ray powder diffraction pattern shown in FIG. 3.

According to the present invention there is provided crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at 2-theta=4.8° plus or minus 0.2° 2-theta.

According to the present invention there is provided a crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at 2-theta=10.0° plus or minus 0.2° 2-theta.

According to the present invention there is provided a crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least two specific peaks at 2-theta=4.8° and 10.0° wherein said values may be plus or minus 0.2° 2-theta.

According to the present invention there is provided a crystalline form, Form A, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with specific peaks at 2-theta=4.8, 10.0, 14.6, 5.2, 19.9, 10.4, 25.4, 23.6, 24.4, 16.2° wherein said values may be plus or minus 0.2° 2-theta.

According to the present invention there is provided a crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at about 2-theta=5.8°.

According to the present invention there is provided a crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at about 2-theta=10.9°.

According to the present invention there is provided a crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least two specific peaks at about 2-theta=5.8° and 10.9°.

According to the present invention there is provided a crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with specific peaks at about 2-theta=5.8, 10.9, 11.5, 25.9, 17.3, 24.0, 19.1, 12.9, 24.7, 27.2°.

According to the present invention there is provided crystalline form, Form B of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern substantially the same as the X-ray powder diffraction pattern shown in FIG. 5.

According to the present invention there is provided crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at 2-theta=5.8° plus or minus 0.2° 2-theta.

According to the present invention there is provided a crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at 2-theta=10.9° plus or minus 0.2° 2-theta.

According to the present invention there is provided a crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least two specific peaks at 2-theta=5.8° and 10.9° wherein said values may be plus or minus 0.2° 2-theta.

According to the present invention there is provided a crystalline form, Form B, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with specific peaks at 2-theta=5.8, 10.9, 11.5, 25.9, 17.3, 24.0, 19.1, 12.9, 24.7, 27.2° wherein said values may be plus or minus 0.2° 2-theta.

According to the present invention there is provided a crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at about 2-theta=6.9°.

According to the present invention there is provided a crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at about 2-theta=12.3°.

According to the present invention there is provided a crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least two specific peaks at about 2-theta=6.9° and 12.3°.

According to the present invention there is provided a crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with specific peaks at about 2-theta=6.9, 12.3, 10.5, 21.0, 24.6, 13.6, 16.4, 19.6, 20.2, 22.5°.

According to the present invention there is provided crystalline form, Form C of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern substantially the same as the X-ray powder diffraction pattern shown in FIG. 7.

According to the present invention there is provided crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at 2-theta=6.9° plus or minus 0.2° 2-theta.

According to the present invention there is provided a crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least one specific peak at 2-theta=12.3° plus or minus 0.2° 2-theta.

According to the present invention there is provided a crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with at least two specific peaks at 2-theta=6.9° and 12.3° wherein said values may be plus or minus 0.2° 2-theta.

According to the present invention there is provided a crystalline form, Form C, of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one which has an X-ray powder diffraction pattern with specific peaks at 2-theta=6.9, 12.3, 10.5, 21.0, 24.6, 13.6, 16.4, 19.6, 20.2, 22.5° wherein said values may be plus or minus 0.2° 2-theta.

When it is stated that the present invention relates to a crystalline form of a compound of the invention, such as Example 1 or Example 3, the degree of crystallinity is conveniently greater than about 60%, more conveniently greater than about 80%, preferably greater than about 90% and more preferably greater than about 95%. Most preferably the degree of crystallinity is greater than about 98%.

When it is stated that the present invention relates to a crystalline form of a compound of the invention, such as Example 1 or Example 3, the crystalline form is preferably substantially free of other crystalline forms or amorphous form of the same compound. In this context, "substantially free" conveniently means greater than about 60%, more conveniently greater than about 80%, preferably greater than about 90%, more preferably greater than about 95%, still more preferable greater than about 98% and even more preferably greater than about 99% pure single crystalline form. For example, Example 3 may be in the form of Form A and substantially free of forms B and C; alternatively, Example 3 may be in the form of Form B and substantially free of forms A and C; alternatively Example 3 may be in the form of Form C and substantially free of forms A and B. Similarly, Example 3 may be in the form of Form B and substantially free of alternative crystalline or amorphous forms.

It will be understood that 2-theta values of the X-ray powder diffraction patterns may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the crystalline Forms of the present invention described above, unless otherwise stated, are not limited to the crystals that provide X-ray powder diffraction patterns identical to the X-ray powder diffraction pattern shown in FIGS. 1, 3, 5 and any crystals providing X-ray powder diffraction patterns substantially the same as those shown in these Figures fall within the scope of the present invention. A person skilled in the art of X-ray powder diffraction is able to judge the substantial identity of X-ray powder diffraction patterns.

Persons skilled in the art of X-ray powder diffraction will also realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction data. Furthermore, it should be understood that intensities might fluctuate depending on experimental conditions and sample preparation (preferred orientation).

Particular compounds of the invention are each of the Examples, each of which provides a further independent aspect of the invention. Further particular compounds of the invention are pharmaceutically-acceptable salt(s) of each of the Examples, each of which provides a further independent aspect of the invention.

According to a further aspect of the invention there is provided a compound of the Formula (I), which is obtainable by following any of the Examples as disclosed herein.

A further feature is any of the scopes defined herein with the proviso that specific Examples, such as Example 1, 3, 4 etc. are individually disclaimed.

It will be appreciated by those skilled in the art that certain compounds of Formula (I) contain asymmetrically substituted carbon atoms, and accordingly may exist in, and be isolated in, optically-active and racemic forms. Some compounds of Formula (I) may exhibit polymorphism. It is to be understood that the present invention encompasses any racemic, optically-active, polymorphic or stereoisomeric form, or mixtures thereof, which form possesses properties useful in the inhibition of PI3K-α and -δ activity, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of PI3K-α and -δ activity by the standard tests described hereinafter.

It is to be understood that certain compounds of Formula (I) defined above may exhibit the phenomenon of tautomerism. It is to be understood that the present invention includes in its definition any such tautomeric form, or a mixture thereof, which possesses PI3K inhibitory activity and is not to be limited merely to any one tautomeric form utilised within the formulae drawings or named in the Examples. In general, just one of any such tautomeric forms is named in the Examples that follow hereinafter or is presented in any relevant formulae drawings that follow hereinafter.

The present invention is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$.

A suitable pharmaceutically-acceptable salt of a compound of the Formula (I) is, for example, an acid-addition salt of a compound of the Formula (I), for example an acid-addition salt with a strong inorganic or organic acid such as hydrochloric, hydrobromic, sulphuric or trifluoroacetic acid. A further suitable pharmaceutically-acceptable salt of a compound of the Formula (I) is, for example, a salt formed within the human or animal body after administration of a compound of the Formula (I).

It is further to be understood that a suitable pharmaceutically-acceptable solvate of a compound of the Formula (I) also forms an aspect of the present invention. A suitable pharmaceutically-acceptable solvate is, for example, a hydrate such as a hemi-hydrate, a mono-hydrate, a di-hydrate or a tri-hydrate or an alternative quantity thereof.

It is further to be understood that a suitable pharmaceutically-acceptable pro-drug of a compound of the Formula (I) also forms an aspect of the present invention. Accordingly, the compounds of the invention may be administered in the form of a pro-drug, which is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in-vivo cleavable ester derivatives that may be formed at a hydroxy group in a compound of the Formula (I), and in-vivo cleavable amide derivatives that may be formed at an amino group in a compound of Formula (I).

Accordingly, the present invention includes those compounds of the Formula (I) as defined hereinbefore when made available by organic synthesis and when made available within the human or animal body by way of cleavage of a pro-drug thereof. Accordingly, the present invention includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A suitable pharmaceutically-acceptable pro-drug of a compound of the Formula (I) is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula (I) that possesses a hydroxy group is, for example, an in vivo cleavable ester or ether thereof. An in vivo cleavable ester or ether of a compound of the Formula (I) containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C) alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula (I) that possesses an amino group is, for example, an in vivo cleavable amide derivative thereof. Suitable pharmaceutically-acceptable amides from an amino group include, for example an amide formed with (1-10C)alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula (I) may be exerted in part by one or more metabolites that are formed within the human or animal body after administration of a compound of the Formula (I). As stated hereinbefore, the in vivo effects of a compound of the Formula (I) may also be exerted by way of metabolism of a precursor compound (a pro-drug).

Compounds of Formula (I) contain a piperidine sub-unit substituted by —C(O)R$^2$, wherein R$^2$ is (C2-3)alkyl substituted by hydroxyl. One potential route of metabolism of these compounds is by oxidation of the hydroxyl substituent on this group. These oxidised compounds generally retain some PI3K-α and -δ inhibitory activity.

Therefore, according to a further aspect of the invention there is provided a compound of the formula (A):

(A)

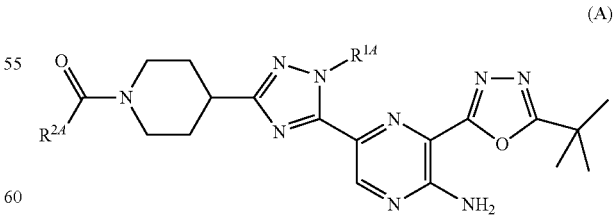

wherein:
R$^{1A}$ is methyl or ethyl; and
R$^{2A}$ is (C1-2)alkyl substituted by carboxy;
or a pharmaceutically-acceptable salt thereof.

Examples of compounds of Formula (A) include Example 8, which is an identified metabolite of Example 1.

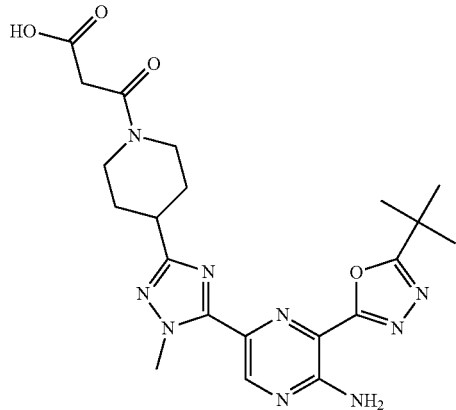

Example 8 and Example 9 which is an identified metabolite of Example 3:

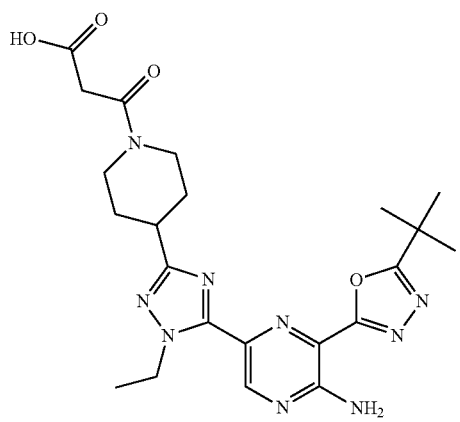

Example 9

Further potential metabolites of Example 3 are two alternative oxidation products, shown below and further described in Examples 10 and 11:

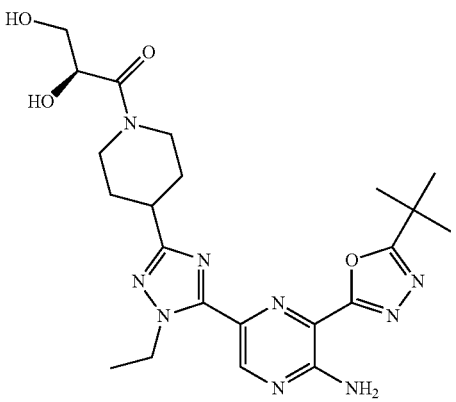

Example 10

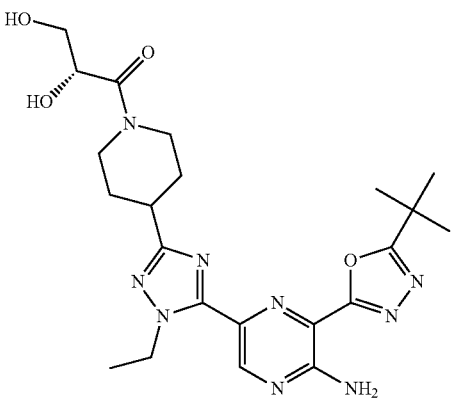

Example 11

Suitable pharmaceutically-acceptable salts of compounds of formula (A) include for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

For the avoidance of doubt it is to be understood that where in this specification a group is qualified by 'hereinbefore defined' or 'defined hereinbefore' the said group encompasses the first occurring and broadest definition as well as each and all of the particular definitions for that group.

Particular novel compounds of the invention include, for example, compounds of the Formula (I), or pharmaceutically-acceptable salts thereof, wherein, unless otherwise stated, each of $R^1$ and $R^2$, has any of the meanings defined hereinbefore or in the following statements:
  $R^1$ is methyl.
  $R^1$ is ethyl.
  $R^2$ is any of groups (i) to (xi) as hereinbefore defined.
  $R^2$ is groups (i) to (vi) as hereinbefore defined.
  $R^2$ is group (i).

A particular group of compounds of the invention are compounds of Formula (I) above wherein:—
  $R^1$ is methyl or ethyl,
  $R^2$ is group (i):

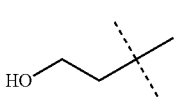

(i)

or a pharmaceutically-acceptable salt thereof.

Particular compounds of the invention are, for example, the compounds of the Formula (I) that are disclosed within the Examples that are set out hereinafter.

For example, a particular compound of the invention is a compound of the Formula (I) selected from any one of the following:—
  1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-propan-1-one (Example 1 and 2);
  1-[4-[5-[5-amino-6-(5-tert-butyl-1,3,4-oxadiazol-2-yl)pyrazin-2-yl]-1-ethyl-1,2,4-triazol-3-yl]-1-piperidyl]-3-hydroxy-propan-1-one (Example 3);

(3R)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-butan-1-one (Example 4);

(3S)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-butan-1-one (Example 5);

(2R)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-2-methyl-propan-1-one (Example 6);

1-[4-[5-[5-amino-6-(5-tert-butyl-1,3,4-oxadiazol-2-yl)pyrazin-2-yl]-1-methyl-1,2,4-triazol-3-yl]-1-piperidyl]-2-hydroxy-2-methyl-propan-1-one (Example 7).

Another aspect of the present invention provides a process for preparing a compound of the Formula (I), or a pharmaceutically-acceptable salt thereof. A suitable process is illustrated by the following representative process variants in which, unless otherwise stated, $R^1$, $R^2$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Suitable process variants include, for example, the following:

(a) The reaction, conveniently in the presence of a suitable activating reagent, of a compound of the Formula II

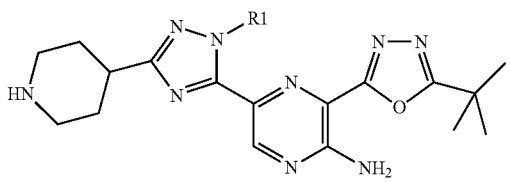

wherein $R^1$ has any of the meanings defined hereinbefore, with the carboxylic acid $R^2$—COOH except that any functional group is protected if necessary, in the presence of a suitable base, whereafter any protecting group that is present is removed. Suitable coupling agents for this reaction include for example, O-(7-azabenzotriazol-1-yl)-N,N,N',N'-tetramethyluronium hexafluorophosphate, TBTU (2-(1H-benzo[d][1,2,3]triazol-1-yl)-1,1,3,3-tetramethylisouronium tetrafluoroborate) or 1-(3-dimethylaminopropyl)-3-ethylcarbodiimide hydrochloride ion the presence of 2-hydroxypyridine N-oxide.

The reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide; preferably N-ethyl-N,N-diisopropylamine.

The reaction is conveniently carried out in the presence of a suitable inert solvent such as for example, acetonitrile, N,N-dimethylformamide, N-methylpyrrolidone, tetrahydrofuran, 1,4-dioxane, 1,2-dimethoxyethane, benzene, toluene, xylene, methanol, ethanol, halogenated solvents such as dichloromethane, chloroform or carbon tetrachloride and at a temperature in the range, for example −50° C. to 100° C., preferably in the range 0° C. to 30° C.

Alternatively, the carboxylic acid $R^2$—COOH may be transformed into an activated species, which can then be reacted with a compound of the Formula II under conditions well known in the art.

A suitable protecting group for the hydroxyl group is the tetrahydropyran protecting group, as described in Example 2 and 3.

Suitable conditions for removing this group include mild acidic conditions in the presence of an alcohol as the solvent at temperature between 20 to 70° C., such as methanol or ethanol. A typical mild acid used is pyridine p-toluenesulfonate.

A compound of Formula II can be obtained from reaction of compound of Formula III:

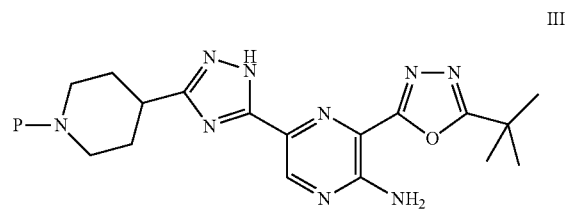

where P is a protecting group, such as tert-butoxycarbonyl, with an compound of Formula $R^1$-L when L is a suitable leaving group such as for example, a halogeno group such as a bromo, iodo group (conveniently iodo), in the presence of a suitable base, whereafter any protecting group that is present is removed.

A suitable base is, for example, an organic amine base, such as 1,8-diazabicyclo[5.4.0]undec-7-ene.

The reaction is conveniently carried out in the presence of a suitable inert solvent such as for example 2-methyltetrahydrofuran, tetrahydrofuran, 1,4-dioxane, 1,2-dimethoxyethane, benzene, toluene, xylene, and at a temperature in the range, for example −50° C. to 60° C., preferably in the range −10° C. to 0° C.

Suitable conditions for deprotection of the tert-butoxycarbonyl include acidic conditions such as trifluoroacetic acid in an inert solvent such as dichloromethane at approximately room temperature (20-25° C.).

Compound III can be obtained from a coupling reaction in the presence of a suitable activating reagent, of compound of Formula IV

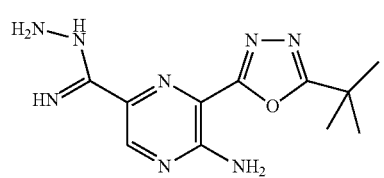

with a compound of Formula V

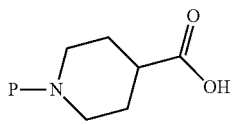

V

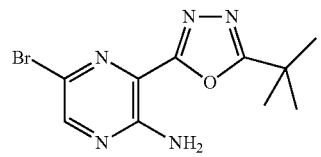

VII preferably in the presence of a suitable base, followed by a cyclisation reaction in the presence of a mild acid.

The coupling reaction can be carried out in the presence of a suitable coupling agent such as, for example, O-(7-azabenzotriazol-1-yl)-N,N,N',N'-tetramethyluronium hexafluorophosphate or TBTU (2-(1H-benzo[d][1,2,3]triazol-1-yl)-1,1,3,3-tetramethylisouronium tetrafluoroborate).

The coupling reaction is conveniently carried out in the presence of a suitable base. A suitable base is, for example, an organic amine base such as, for example, pyridine, 2,6-lutidine, collidine, 4-dimethylaminopyridine, triethylamine, N-methylmorpholine, diazabicyclo[5.4.0]undec-7-ene, diisopropylethyl amine, or, for example, an alkali or alkaline earth metal carbonate or hydroxide, for example sodium carbonate, potassium carbonate, calcium carbonate, sodium hydroxide or potassium hydroxide; preferably N-ethyl-N,N-diisopropylamine.

The coupling reaction is conveniently carried out in the presence of a suitable inert solvent such as for example, N,N-dimethylacetamide, N,N-dimethylformamide, N-methylpyrrolidone, tetrahydrofuran, 1,4-dioxane, 1,2-dimethoxyethane, benzene, toluene, xylene, methanol, ethanol, halogenated solvents such as dichloromethane, chloroform or carbon tetrachloride and at a temperature in the range, for example –50° C. to 100° C., preferably in the range 0° C. to 30° C.

The cyclisation conditions are carried out in the presence of a mild acid, typically acetic acid. The reaction is conveniently carried out in the presence of a suitable inert solvent such as for example, N,N-dimethylacetamide, N,N-dimethylformamide, N-methylpyrrolidone, tetrahydrofuran, 1,4-dioxane, 1,2-dimethoxyethane, benzene, toluene, xylene at a temperature in the range, for example 50° C. to 150° C., preferably in the range 80° C. to 100° C.

Compound IV can be obtained from a reaction of compound of Formula VI with hydrazine.

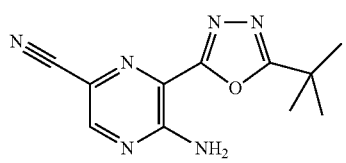

VI

This reaction is conveniently carried out in the presence of a suitable inert solvent such as for example tetrahydrofuran, 1,4-dioxane, 1,2-dimethoxyethane, benzene, toluene, xylene or an alcohol such as ethanol or isopropanol at a temperature in the range, for example 20° C. to 70° C., preferably around 50° C.

Compound VI can be obtained from a metal-catalysed reaction of compound of Formula VII with a source of cyanide such zinc (II) dicyanide.

A suitable catalyst for the reaction includes, for example, a metallic catalyst such as palladium(0), for example tetrakis (triphenylphosphine)palladium(0); or a catalyst formed in-situ from a palladium (II) salt, for example palladium(II) acetate, palladium(II) chloride, palladium(II) bromide, bis (triphenylphosphine)palladium(II) chloride, [1,1'-bis(diphenylphosphino)ferrocene]dichloropalladium(II), or tris (dibenzilideneacetone)dipalladium, and a phosphine ligand, for example, dicyclohexyl(2',4',6'-triisopropylbiphenyl-2-yl)phosphine. The reaction is conveniently carried out in a suitable solvent such as, N,N-dimethylacetamide, N,N-dimethylformamide, tetrahydrofuran, 1,4-dioxane, 1,2-dimethoxyethane, benzene, toluene or xylene and at a temperature in the range, for example 20° C. to 150° C., preferably in the range 60° C. to 120° C. The reaction is also conveniently carried out in the presence of additional metal, such as zinc.

Suitable reactions of this type are described in 'Metal-Catalyzed Cross-Coupling Reactions', Second Edition, Edited by Armin Meijere, Francois Diederich, Wiley-VCH, 2004).

Syntheses of Compound VII have been described in Examples 1 and 2.

Alternatively, a compound of Formula II can be obtained by metal-catalysed reaction of compound VIII, where R is a small alkyl and compound IX, where P is a protecting group, such as tert-butoxycarbonyl,

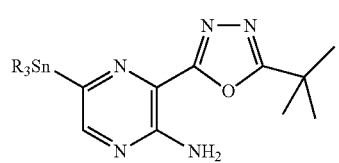

VIII

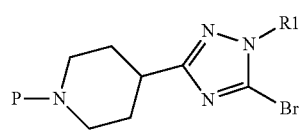

IX

A suitable catalyst for the reaction includes, for example, a metallic catalyst such as palladium(0), for example tetrakis (triphenylphosphine)palladium(0); or a catalyst formed in-situ from a palladium (II) salt, for example palladium(II) acetate, palladium(II) chloride, palladium(II) bromide, bis (triphenylphosphine)palladium(II) chloride, [1,1'-bis(diphenylphosphino)ferrocene]dichloropalladium(II), or tris (dibenzilideneacetone)dipalladium, and a phosphine ligand, for example, dicyclohexyl(2',4',6'-triisopropylbiphenyl-2-yl)phosphine.

The reaction is conveniently carried out in a suitable solvent such as, N,N-dimethylacetamide, N,N-dimethylformamide, tetrahydrofuran, 1,4-dioxane, 1,2-dimethoxyethane, benzene, toluene or xylene or an alcohol such as 4-methyl-2-pentanol at a temperature in the range, for example 50° C. to 180° C., preferably in the range 120° C. to 150° C.

The reaction is also conveniently carried out in the presence of additional salt such as lithium chloride.

Suitable reactions of this type are described in 'Metal-Catalyzed Cross-Coupling Reactions', Second Edition, Edited by Armin Meijere, François Diederich, Wiley-VCH, 2004).

A compound of Formula VIII can be obtained from metal-catalysed reaction of compound VII with a suitable hexa-alkyl distannane. A suitable catalyst for the reaction includes, for example, a metallic catalyst such as palladium (0), for example tetrakis(triphenylphosphine)palladium(0); or a catalyst formed in-situ from a palladium (II) salt, for example palladium(II) acetate, palladium(II) chloride, palladium(II) bromide, bis(triphenylphosphine)palladium(II) chloride, [1,1'-bis(diphenylphosphino)ferrocene]dichloropalladium(II), or tris(dibenzilideneacetone)dipalladium, and a phosphine ligand, for example, dicyclohexyl(2',4',6'-triisopropylbiphenyl-2-yl)phosphine. The reaction is conveniently carried out in a suitable solvent such as, N,N-dimethylacetamide, N,N-dimethylformamide, tetrahydrofuran, 1,4-dioxane, 1,2-dimethoxyethane, benzene, toluene, xylene or an alcohol such as 4-methyl-2-pentanol at a temperature in the range, for example 50° C. to 100° C., preferably in the range 70° C. to 80° C.

Compound of Formula IX can be obtained from commercially available material in a few steps, as illustrated in Example 1 (with $R^1$=Me and P=tert-butoxycarbonyl).

It is to be understood that other permutations of the process steps in the process variants described above are also possible.

It is to be understood that any compound of Formula (I) obtained by any of the processes described hereinbefore can be converted into another compound of the Formula (I) if required.

When a pharmaceutically-acceptable salt of a compound of the Formula (I) is required, for example an acid-addition salt, it may be obtained by, for example, reaction of said compound with a suitable acid.

When a pharmaceutically-acceptable pro-drug of a compound of the Formula (I) is required, it may be obtained using a conventional procedure. For example, an in vivo cleavable ester of compound of the Formula (I) may be obtained by, for example, reaction of a compound of the Formula (I) containing a hydroxy group with a pharmaceutically-acceptable carboxylic acid. Further information on pro-drugs has been provided hereinbefore.

It will also be appreciated that, in some of the reactions mentioned hereinbefore, it may be necessary or desirable to protect any sensitive groups in the compounds. The instances where protection is necessary or desirable, and suitable methods for protection, are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl.

The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates (for example, compounds of the Formulae II, III, IV, VI, VII, VIII) defined herein are novel and these are provided as a further feature of the invention.

BIOLOGICAL ASSAYS

The following assays were used to measure the effects of the compounds of the present invention as a) inhibitors of PI3-kinase enzymes in biochemical assays, b) as inhibitors of other kinases in biochemical assays, c) as inhibitors in vitro of phospho AKT (Thr308) in BT474 cells, d) as inhibitors in vitro of phospho AKT (Ser473) in MDA-MB-468 cells, e) as inhibitors in vitro of phospho AKT (Ser473) in JEKO cells, f) as inhibitors in vitro of phospho Chk1 (Ser345) in HT29 cells, g) as inhibitors of cell proliferation across a panel of tumour cell lines, h & i) as inhibitors in vivo of phospho AKT (Ser473) or inhibitors in vivo of tumour growth respectively, in SCID mice transplanted with the human breast adenocarcinoma cell line, MCF7.

Abbreviations Used in Assay Protocols

PIP2: PI(4,5)P2, phosphatidyl inositol 4,5-bisphosphate
s.c.: sub-cutaneously
ATP: Adenosine triphosphate
DMSO: Dimethyl sulphoxide
TRIS: Tris(Hydroxymethyl)aminomethane
CHAPS: 3-[(3-Cholamidopropyl)dimethylammonio]-1 1-propanesulfonate
DTT: Dithiothreitol
FBS: Foetal bovine serum
DMEM: Dulbecco's Modified Eagle Medium
EDTA: Ethylenediaminetetraacetic acid
EGTA: Ethylene glycol tetraacetic acid
BSA: Bovine Serum albumin
PBS: Phosphate buffered saline
HRP: Horseradish peroxidase
RPMI: Roswell Park Memorial Institute 1640 medium
4NQO: 4-Nitroquinoline N-oxide
EMEM: Eagle's Minimal Essential medium
$CO_2$: Carbon dioxide
PBST: Phosphate buffered saline/Tween
Ab: Antibody
MTS reagent: [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS.

(a) In Vitro Enzyme Inhibition Assay

The inhibition of PI3K-β, PI3K-α, PI3K-γ and PI3K-δ was evaluated in a Kinase Glo based enzyme activity assay using human recombinant enzymes. The assay platform indirectly measured the depletion of ATP after incubation with enzyme, PIP2 substrate, ATP and compound.

After completion of the enzyme reaction the remaining ATP was used in a secondary enzymatic reaction, where Luciferase converted beetle luciferin into oxyluciferin under the emission of light. A direct relationship existed between the luminescence measured and the ATP remaining in a completed kinase reaction. Therefore, the luminescence was inversely related to the kinase activity. Typically, twelve different compound concentrations were tested and raw data from the inhibition of PI3K-β, PI3K-α, PI3K-γ or PI3K-δ were plotted versus inhibitor concentration.

Method Details:

Compounds in 100% DMSO were added to assay plates by acoustic dispensing. PI3K enzyme was added in a Tris buffer (50 mM Tris pH7.4, 0.05% CHAPS, 2.1 mM DTT, and 10 mM magnesium chloride) and allowed to preincubate with compound for 20 minutes prior to addition of substrate solution containing PIP2 and ATP. The enzyme reaction was stopped after 80 minutes by the addition of Kinase Glo detection solution containing Luciferin and Luciferase (from Kinase Glo® Plus Luminescent Kinase Assay kit (Promega #V3772). Plates were left for 30 minutes at room temperature then read on a Pherastar Instrument with a standard Luminescence filter block. The final concentration of DMSO, ATP and PIP2 in the assay were, 1%, 8 µM, and 80 µM respectively.

Data Analysis $IC_{50}$ values were calculated using a log curve fitting to a non-linear regression fit. The $IC_{50}$ value was the concentration of test compound that inhibited 50% of enzyme activity.

(b) Evaluation of Kinase Selectivity, Beyond PI3Kinase Class I Enzymes

Large panels of kinase assays are offered by a range of commercial vendors such as Millipore, Invitrogen and ProQinase. Such panels allow for an assessment of the overall kinase selectivity of a given compound. The precise methods/technologies will vary depending on the vendor.

Selectivity data for some of the compounds described herein was generated using enzyme assays performed at the MRC-Division of Signal Transduction Therapy (DSTT), MRC Protein Phosphorylation Unit, Dundee, UK. Protein kinase assays were carried using a Radiochemical format. Assays were performed in multidrop 384 well plates at room temperature in a total assay volume of 25.5 µl. Compounds were pre-incubated in the presence of the enzyme and peptide/protein substrate for 5 minutes before initiation of the reaction by addition of 10 µl of ATP (final concentration selected for each kinase at 5, 20 or 50 µM). Assays were run at room temperature before termination by the addition of 5 µl orthophosphoric acid. The assay plate contents were then harvested onto Whatman-P81-Unifilter Plates by a Packard Harvester (wash buffer was 50 mM orthophosphoric acid) and dried in air. The dry Unifilter plates were then sealed on the addition of MicroScint O and were counted in Packard Topcount NXT scintillation counters. This protocol captures the generic format suitable for the majority of kinases in the panel, but modifications to the protocols were required for a small number of kinases, as will be familiar to those skilled in the art.

Lipid kinase assays for ~18 lipid kinases were also performed at DSTT. All lipid kinase assays were carried out in 384 well plates at room temperature in a total assay volume of 40 µl. The assay was performed according to the protocols provided with the ADP-GLO assay (Promega, #V9101). This protocol captures the generic format suitable for the majority of kinases in the panel, but modifications to the protocols were required for a small number of kinases, as will be familiar to those skilled in the art.

Kinase selectivity was also evaluated using the KINOMEscan™ screening platform, available via DiscoverX. This employs an active site-directed competition binding assay to quantitatively measure interactions between test compounds and more than 450 human kinases and disease relevant mutant variants. KINOMEscan™ assays do not require ATP and thereby report true thermodynamic interaction affinities, as opposed to IC50 values, which can depend on the ATP concentration. The methodology is based on compounds that bind the kinase active site and directly (sterically) or indirectly (allosterically) preventing kinase binding to the immobilized ligand, thereby reducing the amount of kinase captured onto a solid support. Conversely, test molecules that do not bind the kinase have no effect on the amount of kinase captured on a solid support. Screening "hits" are identified by measuring the amount of kinase captured in test versus control samples by using a quantitative qPCR method that detects the associated DNA label. In a similar manner, dissociation constants (Kds) for test compound-kinase interactions are calculated by measuring the amount of kinase captured on the solid support as a function of the test compound concentration.

(c) Protocol for Assay Measuring Phosphorylated AKT (Tyr308) in BT474 Cells

This assay was used to measure PI3K-α inhibition in cells. BT474 cells (human breast ductal carcinoma, ATCC HTB-20) were seeded into black 384 well plates (Costar, #3712) at a density of 5600 cells/well in DMEM containing 10% FBS and 1% glutamine and allowed to adhere overnight.

The following morning compounds in 100% DMSO were added to assay plates by acoustic dispensing. After a 2 hour incubation at 37° C. and 5% $CO_2$, the medium was aspirated and the cells were lysed with a buffer containing 25 mM Tris, 3 mM EDTA, 3 mM EGTA, 50 mM sodium fluoride, 2 mM Sodium orthovanadate, 0.27M sucrose, 10 mM 3-glycerophosphate, 5 mM sodium pyrophosphate, 0.5% Triton X-100 and complete protease inhibitor cocktail tablets (Roche #04 693 116 001, used 1 tab per 50 ml lysis buffer).

After 20 minutes, the cell lysates were transferred into ELISA plates (Greiner #781077) which had been pre-coated with an anti total-AKT antibody in PBS buffer and non-specific binding was blocked with 1% BSA in PBS containing 0.05% Tween 20. Plates were incubated over night at 4° C. The next day the plates were washed with PBS buffer containing 0.05% Tween 20 and further incubated with a mouse monoclonal anti-phospho AKT T308 for 2 hours. Plates were washed again as above before addition of a horse anti-mouse-HRP conjugated secondary antibody. Following a 2 hour incubation at room temperature, plates were washed and QuantaBlu substrate working solution (Thermo Scientific #15169, prepared according to provider instruction) was added to each well. The developed fluorescent product was stopped after 60 minutes by addition of Stop solution to the wells. Plates were read using a Tecan Safire plate reader using 325 nm excitation and 420 nm emission wavelengths respectively. Except where specified, reagents contained in the Path Scan Phospho AKT (Thr308) sandwich ELISA kit from Cell Signalling (#7144) were used in this ELISA assay.

(d) Protocol for Detection of Phospho AKT (Ser473) in MDA-MB-468 Cells as a Measure for PI3Kinase-Beta Inhibition.

This assay was used to measure PI3K-β inhibition in cells, and was used, in conjunction with assay (c) above, to determine alpha vs beta selectivity in cells. MDA-MB-468 cells (human breast adenocarcinoma #ATCC HTB 132) were seeded at 1500 cells/well in 40 µl of DMEM containing 10% FBS and 1% glutamine into Greiner 384 well black flat-bottomed plates. Cell plates were incubated for 18 hours in a 37° C. incubator before dosing with compounds in 100% DMSO using acoustic dispensing.

Compounds were dosed in a 12 point concentration range into a randomised plate map. Control wells were generated either by dosing of 100% DMSO (max signal) or addition of a reference compound (a PI3K-β inhibitor) that completely eliminated the pAKT signal (min control). Plates were incubated at 37° C. for 2 hours, cells were then fixed by the addition of 10 µl of a 3.7% formaldehyde solution. After 30 minutes the plates were washed with PBS using a Tecan PW384 plate washer. Wells were blocked and cells permeabilised with the addition of 40 µl of PBS containing 0.5% Tween20 and 1% Marvel™ (dried milk powder) and incubated for 60 minutes at room temperature. The plates were washed with PBS containing 0.5% (v/v) Tween20 and 20 µl rabbit anti-phospho AKT Ser473 (Cell Signalling Technologies, #3787) in same PBS-Tween+1% Marvel™ was added and incubated overnight at 4° C.

Plates were washed 3 times with PBS+0.05% Tween 20 using a Tecan PW384. 20 µl of secondary antibody Alexa Fluor 488 anti-Rabbit (Molecular Probes, #A11008) diluted in PBS+0.05% Tween20 containing 1% Marvel™ was added to each well and incubated for 1 hour at room temperature. Plates were washed three times as before then 20 µl PBS added to each well and plates sealed with a black plate sealer.

The plates were read on an Acumen plate reader as soon as possible, measuring green fluorescence after excitation with 488 nm laser. Using this system $IC_{50}$ values were generated and quality of plates was determined by control wells. Reference compounds were run each time to monitor assay performance.

(e) Protocol for Detection of Phospho AKT (Ser473) in Jeko Cells

This assay was used to measure PI3K-δ inhibition in cells. Compounds at ×10 final concentration in 10 µl of 1% (v/v) DMSO were added to the wells of a Greiner V-bottomed 96 well plate (Sigma #M9686). Compounds were dosed in a 10-point concentration range from top dose of 1 µM or 10 µM, 8 compounds were dosed on one plate. There were 8 maximum signal control wells per plate dosed with anti-IgM (AffiniPure F(ab')2 Fragment Goat Anti-Human IgM (Stratech, #109-006-129) and vehicle, and 8 minimum signal control wells dosed with anti-IgM and a reference PI3K-δ inhibitor. Final vehicle concentration was 0.1% DMSO. A full dose response curve for a PI3K-δ selective compound was included in each run. Jeko B cells (human mantle cell lymphoma, ATCC #CRL-3006) were seeded into the Greiner 96 well V-bottomed plates containing compounds. Cells were seeded at 100,000 cell/well in 70 µl of RPMI containing 1% glutamine.

Cell plates were incubated with compound for 1 hour in a 37° C. incubator. After this compound pre-incubation time, the above described anti-IgM was added to the plates at ×5 final concentration in 20 µl of assay buffer (RPMI containing 1% glutamine). Final anti-IgM concentration was 0.06 µg/ml or an equivalent EC90 dose. Plates were incubated at 37° C. for 10 min, then plates were immediately placed on ice and centrifuged at 12000 rpm for 4 min. On ice, supernatants were carefully removed with a manual pipette and 40 µl lysis buffer added. Plates were incubated on ice for 5 min and stored at −80° C. until assayed in the phosphor (Ser473)/total Akt whole cell lysate kit according to manufacturer's instructions (Mesoscale Diagnostics, #K11100D-3).

(f) Protocol for Detection of Phospho Chk1 (Ser 345) in HT29 Cells

ATR (Ataxia Telangiectasia+Rad3-related kinase) is a PI3-kinase-related kinase which phosphorylates multiple substrates on serine or threonine residues in response to DNA damage or replication blocks. Chk1, a downstream protein kinase of ATR, plays a key role in DNA damage checkpoint control. Activation of Chk1 involves phosphorylation of Ser317 and Ser345 (the latter regarded as the preferential target for phosphorylation/activation by ATR).

This was a cell based assay to measure inhibition of ATR kinase, by measuring a decrease in phosphorylation of Chk1 (Ser 345) in HT29 cells, following treatment with compound and the UV mimetic 4NQO (Sigma #N8141). HT29 cells (ECACC #85061109) were seeded into 384 well assay plates (Costar #3712) at a density of 6000 cells/well in 40 µl EMEM medium containing 1% L glutamine and 10% FBS and allowed to adhere overnight. The following morning compounds in 100% DMSO were added to assay plates by acoustic dispensing. After 1 hour incubation at 37° C. and 5% $CO_2$, 40 nl of 3 mM 4NQO in 100% DMSO was added to all wells by acoustic dispensing, except minimum control wells which were left untreated with 4NQO to generate a null response control. Plates were returned to the incubator for a further 1 hour. Then cells were fixed by adding 20 µl of 3.7% formaldehyde in PBS solution and incubating for 20 mins at room temperature. Then 20 µl of 0.1% Triton X100 in PBS was added and incubated for 10 minutes at room temperature, to permeabalise cells. Then the plates were washed once with 50 µl/well PBS, using a Biotek EL405 plate washer.

Phospho-Chk1 Ser 345 antibody (Cell Signalling Technology #2348) was diluted 150 fold in PBS containing 0.05% polysorbate/Tween and 15 µl was added to each well and incubated over night at room temperature. The next morning plates were washed three times with 50 µl/well PBS, using a Biotek EL405 plate washer, and then 20 µl of secondary Ab solution, containing 500 fold diluted Alexa Fluor 488 Goat anti-rabbit IgG (Molecular Probes #A-11008) and 0.002 mg/ml Hoeschst dye (Molecular Probes #H-3570), in PBST, was added. After 2 hours incubation at room temperature, the plates were washed three times with 50 µl/well PBS, using a Biotek EL405 plate washer, and plates were then sealed with black plate seals until read. Plates were read using an ArrayScan VTI instrument, using an XF53 filter with 10× objective. A two laser set up was used to analyse nuclear staining with Hoeschst (405 nM) and secondary antibody staining of pChk1 (488 nM).

(g) Cell Proliferation Assays in Tumour Cell Lines (Used to Demonstrate a Personalised Medicine Hypothesis)

The sensitivity of a panel of human cancer cell lines to the effects of compounds was determined in a standard proliferation assay. Cell lines were sourced through the AstraZeneca Cell Bank. The majority of cell lines are also available through Cell Bank Repositories known to those working in the art, for example ATCC, ECACC, DMSZ, RIKEN, KCLB, JCRB (HSRRB), LBNL, CLS and ICLC.

Cells were plated in 96 well plates at densities of 1000-6000 cells per well in RPMI media containing 10% FBS. After incubation at 37° C. for 16 hours, various concentrations of compound were added to the assay plates. After incubation for an additional 72 h, the viable cells were determined by the addition of MTS reagent (Promega #3582) to each well for 2 h. MTS is a tetrazolium salt that is bioreduced by metabolically active cells in the presence of an electron coupling reagent to formazan. The formazan product was then quantitated by absorbance at 490 nm, as an indicator of the relative number of live cells. In order to determine the GI50 (concentration at which growth of cells was inhibited by 50%) the relative number of cells present at the time of drug addition was determined by comparison with the MTS readout before the drug was added, and this value was subtracted from the 72 hr value of untreated cells as a measure of cell growth during the assay.

Analysis of this data, described below under 'Personalised Healthcare/Personalised Medicine Examples' illustrates how this data may be analysed to reveal that PI3Kα inhibitors display selective growth inhibition of cell lines with PIK3CA gene mutation. This illustrates a Personalised Healthcare (PHC) or Personalised Medicine opportunity where a response prediction biomarker readout could be used to identify patients with tumours containing mutation in the PIK3CA gene and who would be more likely to respond to the compounds described herein.

Other potential markers of response to the compounds described herein include, but are not limited to, increased copy number, amplification or translocation of the PIK3CA gene, and other genetic, genomic or proteomic changes which provide a measure of PI33-Kinase pathway activation or dependency; for example but not limited to, activation of one or more receptor tyrosine kinases, or mutation in the PIK3R genes which encode the regulatory subunits (p85) of PI3-Kinase, or phosphorylation of downstream signalling markers such as pAKT, pS6, or FOXO status. In addition, analysis of further genes and/or the signalling of their protein products, for example Kras, may help improve the predictivity of a Personalised Medicine approach.

(h) Protocol for Detection of Phospho AKT (Ser473) from MCF-7 Tumours Grown in Male SCID Mice This was a pharmacodynamic assay providing a measure of PI3K-α inhibition in an animal model. Male SCID mice (AZ UK, also available from Charles River, UK) were transplanted sub-cutaneously (s.c.) with human breast adenocarcinoma cell line MCF7 (ICRF London, also available from ATCC #HTB-22)) to determine the inhibition of phosphorylation of AKT with PI3-kinase inhibitors. Mice were implanted with a 0.5 mg 21-day oestrogen pellet (Innovative Research of America, #E121) 24 hours prior to cell implantation. $5\times10^6$ cells in 50% matrigel (BD Bioscience) were injected s.c. on the left flank of the animals. Animals were randomised into groups of 8 control and 4 treatment when tumours reached a volume of 400 $mm^3$ and dosing commenced the next day. Tumours were taken at selected time points, when blood samples were also taken for PK measurements.

Tumours excised from mouse were placed into a Fast Prep tube (2 ml ridged tubes containing lysing matrix A, MP Biomedicals #6910-500) and immediately snap frozen. 1 ml of lysis buffer (25 mM Tris, 3 mM EDTA, 3 mM EGTA, 50 mM sodium fluoride, 2 mM orthovanadate, 0.27M sucrose, 10 mM beta-glycerophoshate, 5 mM pyrophosphate, 0.5% Triton x-100) plus phosphatase inhibitors (Sigma #P2850 and Sigma #P5726, diluted 1:100) and protease inhibitors (Sigma #P8340, diluted 1:200) were added to each tube. The tumours were homogenised for 1 minute on a FastPrep™ machine (MP Biomedicals #116004500) and then left on ice for 5 minutes, followed by two further homogenisations steps, each followed by a 5 minutes incubation on ice. Samples were spun for 10 minutes at 13,000 rpm in a chilled centrifuge. Cleared lysates were then taken into fresh tubes and 10 µl used for a protein determination assay The detection of total and phosphorylated AKT (ser473) was carried out using a MSD multi-spot assay kit (Meso Scale Discovery #K15100D-3). Each well of the plate contained 4 spots; two of these were coated with mouse monoclonal antibodies provided with the kit; one was coated with a capture antibody for total AKT and one was coated with an antibody for phosphorylated AKT (ser473). The plates were blocked overnight in the cold room on a shaker with 150 µl of blocking solution per well, which was made using 20 ml of 1× solution of wash solution plus 600 mg Blocker A supplied with the kit. Plates were washed three time with 0.3 ml per well of wash solution. An aliquot of the lysate was taken from each tumour and diluted to a concentration of 2 mg/ml with lysis buffer, 25 µl of the diluted lysate was then added to each well giving a total amount of 50 µg per well. The plates were placed on a shaker at room temperature for one hour before plates were washed three times. A detection antibody solution was prepared using a mix of blocking and wash solution plus a 1 in 50 dilution of the 50× SULFO-TAG™ anti-total AKT antibody. The plates were placed on a shaker at room temperature for one hour before plates were washed three times. 150 µl of read buffer supplied with the kit was diluted 1:4 with deionised water and added to each well and then the plate was read on MSD plate analyser. The read buffer gives the correct chemical environment for electrochemiluminescence, so that when the plate reader applies a voltage to the plate the electrodes on the base of the plate cause the label bound to the detection antibody to emit light. The intensity of light emitted is a quantitative measure of the AKT, either total or phosphorylated, that is present. To calculate the ratio of phosphorylated to total AKT a calculation was applied as suggested by Meso Scale: two times phosphorylated signal divided by total plus phosphorylated signal then multiplied by 100 to give % phosphoprotein. The values were converted into Log 10, and then these values were used to calculate the Geomean for each group plus standard error. A student T test was then applied using 2 tailed formula and unequal variance to check for significance. Studies showed that a control group of 8 animals with 4 per treatment group were sufficient to power the study.

(i) Protocol for Detection of Tumour Growth Inhibition in Human Breast Adenocarcinoma Cell Line MCF7 Transplanted into SCID Mice.

Test (c):—$IC_{50}$ versus cellular phospho AKT (Tyr308) in BT474 cells, in the range, for example, 10 nM-1 µM;

Conveniently, particular compounds of the invention possess activity at the following concentrations or doses in one or more of the above tests (a), (c), (h) and (i):—

Test (a):—$IC_{50}$ versus PI3K-α in the range, for example, 1 nM-100 nM;

Test (c):—$IC_{50}$ versus cellular phospho AKT (Tyr308) in BT474 cells, in the range, for example, 10 nM-1 µM;

Test (h):—>50% inhibition of in vivo phospho AKT (ser473) in the range, for example, 1-200 mg/kg/day;

Test (i):—xenograft activity in the range, for example, 1-200 mg/kg/day.

The following data were generated for the Examples:

TABLE A

| Example number | PI3K-α inhibition $IC_{50}$ (µM)* | PI3K-δ inhibition$IC_{50}$ (µM)* | PI3K-β inhibition$IC_{50}$ (µM)* | PI3K-α cell $IC_{50}$ (µM) ** | ATR cell $IC_{50}$ (µM)# |
|---|---|---|---|---|---|
| 1 | 0.023 | <0.014 | 2.24 | 0.36 | >30 |
| 3 | 0.007 | <0.010 | 0.57 | 0.09 | >30 |
| 4 | 0.025 | <0.012 | 2.91 | 0.31 | >30 |
| 5 | 0.030 | 0.012 | 3.31 | 0.27 | >30 |
| 6 | 0.032 | <0.012 | 3.42 | 0.53 | >30 |
| 7 | 0.037 | 0.014 | 6.26 | 0.42 | >30 |
| 8 | 0.024 | 0.012 | 1.52 | 0.59 | >30 |
| 9 | <0.010 | <0.010 | 0.640 | 0.33 | — |
| 10 | — | — | — | 0.085 | — |
| 11 | — | — | — | 0.11 | — |

*Test protocol a: these are mean values calculated from a number of replicates of the test.
** Test protocol c: these are mean values calculated from a number of replicates of the test.
Test protocol f: one test replicate only carried out.

This method provides for assessment of anti-tumour efficacy of PI3-kinase inhibitors in vivo, in a PI3K-α dependent model. As for the PD studies, indicated above, male SCID mice were transplanted s.c. with human breast adenocarcinoma cell line, MCF7. Mice were implanted with a 0.5 mg 21-day oestrogen pellet 24 hours prior to cell implantation. $5 \times 10^6$ cells in 50% matrigel were injected s.c. on the left flank of the animals. Animals were randomised into groups of 10-15 when tumours reached a volume of ~200-300 mm³ and treatment commenced. Animals were dosed for 2-4 weeks by peroral, intravenous or intra-peritoneal routes with compound in a vehicle suitable for dosing via the required route and consistent with welfare requirements (suspension for oral dosing in pH range 4-7, solution for ip/iv dosing in pH range 5.5-7.0) and at defined doses. Tumours were usually measured twice weekly by caliper and volume of tumours calculated using elliptical formula (pi/6×width×width×length).

Although the pharmacological properties of the compounds of the Formula (I) vary with structural change as expected, in general activity possessed by compounds of the Formula (I) may be demonstrated at the following concentrations or doses in one or more of the above tests (a) and (c):—

Test (a):—$IC_{50}$ versus PI3K-α in the range, for example, 1 nM-100 nM;

Test (c):—$IC_{50}$ versus cellular phospho AKT (Tyr308) in BT474 cells, in the range, for example, 10 nM-1 µM;

Conveniently, particular compounds of the invention possess activity at the following concentrations or doses in one or more of the above tests (a) and (c):—

Test (a):—$IC_{50}$ versus PI3K-α in the range, for example, 1 nM-100 nM;

Combination Studies

Materials and Methods

MCF7 is an estrogen receptor positive breast tumour cell line carrying a mutation in the PIKC3CA gene (E545K). Male SCID mice (AZ UK) were transplanted subcutaneously (s.c.) with human breast adenocarcinoma cell line MCF7 (ICRF London) to determine anti-tumour activity of PI3 kinase inhibitors. Mice were implanted with a 0.5 mg 21 day oestrogen pellet (Innovative Research of America) 24 hours prior to cell implantation. $5 \times 10^6$ cells in 50% matrigel (BD Bioscience) were injected s.c. on the left flank of the animals.

BT474 is an estrogen receptor positive breast tumour cell lines with elevated Her2 expression and carries a mutation in the PIK3CA gene (K111N). Female Swiss athymic nude mice (swiss nu/nu—AZUK) were transplanted subcutaneously with human epithelial breast ductal carcinoma cell line BT474c (derived in AZ from BT474—ATCC HTB-20) tumours passaged in mice. Mice were implanted with 0.36 mg 60 day oestrogen pellet (Innovative Research of America) 24 hours prior to cell implantation. $5 \times 10^6$ cells in 50% matrigel (BD Bioscience) were injected s.c. on the left flank of the animals.

HCC70 is breast tumour cell line which is deficient in PTEN gene expression. Female Swiss athymic nude mice (swiss nu/nu—AZUK) were transplanted subcutaneously with the breast ductal epithelial tumour cell line HCC70 (ATCC—CRL2315) cells. $1 \times 10^6$ cells in 50% matrigel (BD Bioscience) were injected s.c. on the left flank of the animals.

Animals were randomised into groups of 10-15 when tumours reached a volume of ~200-300 mm³ and treatment commenced. Animals were dosed for 3-4 weeks by peroral route, with compound in a suitable vehicle at defined doses and schedules. Tumours were measured two-three times weekly by caliper and volume of tumours calculated using elliptical formula (pi/6×width×width×length).

When dosed alone, AZD5363 was formulated in 10% DMSO, 25% Kleptose solution. (Kleptose is sourced from Roquette—Pharma (Trademarked) Hydroxypropyl betacyclodextrin—suitable for in vivo use and formulations).

When co-dosed with Example 3, AZD5363 was formulated in HPMC/Tween (0.5% Methocel (hydroxypropyl methocellulose)/0.1% Polysorbate 80). The suspension was ball milled overnight.

Example 3 was formulated in HPMC/Tween (0.5% Methocel (hydroxypropyl methocellulose)/0.1% Polysorbate 80).

AZD8186 was formulated in HPMC/Tween (0.5% Methocel (hydroxypropyl methocellulose)/0.1% Polysorbate 80).

When co-dosed with Example 3, AZD8186 was formulated in HPMC/Tween (0.5% Methocel (hydroxypropyl methocellulose)/0.1% Polysorbate 80). The suspension was ball milled overnight.

Olaparib was formulated in 10% DMSO/30% Kleptose solution.

Tumour Growth Inhibition by Example 3 in Combination with AKT Inhibitor (AZD5363)—Sequential Administration Studies were performed in the BT474 xenograft model. Example 3 and AZD5363 were dosed twice daily (BID) 6-8 hours apart on a 2 days on/5 days off weekly cycle, in sequence such that AZD5363 was dosed on days 1 and 2 of the weekly cycle and Example 3 was dosed on days 3 and 4 of the weekly cycle. Example 3 was dosed at 50 mg/kg BID and AZD5363 was dosed at 170 mg/kg BID, in HPMC/Tween and DMSO/Kleptose respectively.

The tumour growth curve (shown in FIG. 9) indicates that intermittent dosing of either Example 3 or AZD5363 partially inhibited tumour growth relative to vehicle only control (HPMC/Tween). The combination of Example 3 plus AZD5363 induced tumour regression.

Tumour Growth Inhibition by Example 3 in Combination with AKT Inhibitor (AZD5363)—Co-Administration Studies were performed in the BT474 xenograft model. Example 3 and AZD5363 were dosed twice daily (BID) 6-8 hours apart and concomitantly on a 2 days on/5 days off weekly cycle. Example 3 was dosed at 25 mg/kg BID and AZD5363 was dosed at 100 mg/kg BID, both in HPMC/Tween.

The tumour growth curve (shown in FIG. 10) indicates that intermittent dosing of either Example 3 or AZD5363 partially inhibited tumour growth relative to vehicle only control (HPMC/Tween). The combination of Example 3 plus AZD5363 induced tumour regression during the dosing period, although followed by tumour re-growth during the dosing free period.

Tumour Growth Inhibition by Example 3 in Combination with PARP Inhibitor (Olaparib)

Studies were performed in the BT474 xenograft model. Example 3 and Olaparib were dosed on every day throughout the study, Example 3 twice daily (BID) 6-8 hours apart at 25 mg/kg each dose and Olaparib once daily (QD) at 100 mg/kg 1 hour post first daily dose of Example 3. Both agents were dosed in HPMC/Tween.

The tumour growth curve (FIG. 11) indicates that olaparib alone had no significant effect on tumour growth, example 3 alone partially inhibited growth, but the combination of Example 3 plus olaparib induced tumour regression.

Tumour Growth Inhibition by Example 3 in Combination with PARP Inhibitor (Olaparib)

Studies were performed in the MCF7 xenograft model. Example 3 and Olaparib were dosed on every day throughout the study, Example 3 twice daily 6-8 hours apart at 25 mg/kg each dose and Olaparib once daily (QD) at 100 mg/kg 1 hour post first daily dose of Example 3. Both agents were dosed in HPMC/Tween.

The tumour growth curve (FIG. 12) indicates that olaparib alone had minimal effect on tumour growth, Example 3 alone caused some tumour regression, but the combination of Example 3 plus olaparib induced stronger tumour regression.

Tumour Growth Inhibition by Example 3 in Combination with PI3Kbeta/Delta Inhibitor (AZD8186)

Studies were performed in the HCC70 xenograft model. Example 3 and AZD8186 were dosed on every day, twice daily (BID), throughout the study, Example 3 at 25 mg/kg each dose and AZD8186 at 50 mg/kg each dose. Both agents were dosed in HPMC/Tween. The tumour growth curve (FIG. 13) indicates that AZD8186 partially inhibited tumour growth, Example 3 alone inhibited growth more strongly, but the combination of Example 3 plus AZD8186 induced tumour regression.

According to a further aspect of the invention there is provided a pharmaceutical composition, which comprises a compound of the Formula (I), or a pharmaceutically-acceptable salt thereof, as defined hereinbefore in association with a pharmaceutically-acceptable diluent or carrier.

Suitable pharmaceutically acceptable excipients for a tablet formulation include, for example, inert diluents, granulating and disintegrating agents, binding agents, lubricating agents, preservative agents and anti-oxidants. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may alternatively be in the form of hard gelatin capsules in which the active ingredient is mixed with an inert solid diluent, or as soft gelatin capsules in which the active ingredient is mixed with water or an oil.

Aqueous suspensions generally contain the active ingredient in finely powdered form together with one or more suspending agents, dispersing or wetting agents. The aqueous suspensions may also contain one or more preservatives, anti-oxidants, colouring agents, flavouring agents, and/or sweetening agents.

Oily suspensions may be formulated by suspending the active ingredient in a vegetable oil or in a mineral oil. The oily suspensions may also contain a thickening agent. Sweetening agents such as those set out above, and flavouring agents may be added to provide a palatable oral preparation. These compositions may be preserved by the addition of an anti-oxidant.

Dispersible powders and granules suitable for preparation of an aqueous suspension by the addition of water generally contain the active ingredient together with a dispersing or wetting agent, suspending agent and one or more preservatives. Additional excipients such as sweetening, flavouring and colouring agents, may also be present.

The pharmaceutical compositions of the invention may also be in the form of oil-in-water emulsions. The oily phase may be a vegetable oil or a mineral oil or a mixture of any of these. The emulsions may also contain sweetening, flavouring and preservative agents.

Syrups and elixirs may be formulated with sweetening agents, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, oral administration to humans will generally require, for example, from 1 mg to 2 g of active agent (more suitably from 100 mg to 2 g, for example from 250 mg to 1.8 g, such as from 500 mg to 1.8 g, particularly from 500 mg to 1.5 g, conveniently from 500 mg to 1 g) to be administered compounded with an appropriate and convenient amount of excipients which may vary from about 3 to about 98 percent by weight of the total composition. It will be understood that, if a large dosage is required, multiple dosage forms may be required, for example two or more tablets or capsules, with the dose of active ingredient divided conveniently between them. Conveniently, a single solid dosage form may contain between 1 and 300 mg of active ingredient.

The size of the dose for therapeutic or prophylactic purposes of a compound of the Formula (I) will naturally vary according to the nature and severity of the disease state, the age and sex of the animal or patient and the route of administration, according to well known principles of medicine.

In using a compound of the Formula (I) for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. Typically, unit dosage forms will contain about 10 mg to 0.5 g of a compound of this invention.

The compounds of the invention may be administered daily or more than once daily. The compounds of the invention may also be administered in a suitable dosing schedule, for example the compounds of the invention may be administered one or more times per day (for example once, twice or three times a day) for a certain number of This days, followed by a period of days where no dose is given. This dosage cycle (consisting of dosing days and no-dosing days) may then be repeated. Conveniently a dosage cycle is a period of 5-14 days, such as 5, 7, 10 or 14 days, more conveniently 7 days. In one aspect, the compounds of formula (I) are dosed for 1 day or 2 or 3 consecutive days, followed by 3, 4, 5 or 6 days with no dose in a dosage cycle.

In one aspect the compound of formula (I) is dosed for 1 day followed by no dose for 2, 3 or 4 days.

In another aspect the compound of formula (I) is dosed for 2 days followed by no dose for 4, 5 or 6 days.

In a further aspect the compound of formula (I) is dosed for 3 days followed by no dose for 3, 4 or 5 days.

In another aspect the compound of formula (I) is dosed for 4 days followed by no dose for 2, 3 or 4 days.

In another aspect the compound of formula (I) is dosed for 5 days followed by no dose for 1, 2 or 3 days.

In another aspect, the compound of formula (I) is dosed every other day.

The above dosing schedules are conveniently applied when the compounds of the invention are used as monotherapy. Further examples of potential dosing schedules for administration of the compounds of the invention as combination therapy are described hereinafter.

As stated above, it is known that PI3K-$\alpha$ and -$\delta$ enzymes contribute to tumourigenesis by one or more of the effects of mediating proliferation of cancer and other cells, mediating angiogenic events and mediating the motility, migration and invasiveness of cancer cells. We have found that the compounds of the present invention possess potent anti-tumour activity which it is believed is obtained by way of inhibition of PI3K-$\alpha$ and -$\delta$ enzymes that are involved in the signal transduction steps which lead to the proliferation and survival of tumour cells and the invasiveness and migratory ability of metastasising tumour cells.

Accordingly, the compounds of the present invention are of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present invention are of value as anti-proliferative and anti-invasive agents in the containment and/or treatment of solid tumour disease. Particularly, the compounds of the present invention are expected to be useful in the prevention or treatment of those tumours which are sensitive to inhibition of PI3K-$\alpha$ and/or -$\delta$ enzymes and that are involved in the signal transduction steps which lead to the proliferation and survival of tumour cells and the migratory ability and invasiveness of metastasising tumour cells. Further, the compounds of the present invention are expected to be useful in the prevention or treatment of those tumours which are mediated alone or in part by inhibition of PI3K-$\alpha$ and/or -$\delta$ enzymes, i.e. the compounds may be used to produce a PI3K-$\alpha$ and/or -$\delta$ enzyme inhibitory effect in a warm blooded animal in need of such treatment.

According to a further aspect of the invention there is provided a compound of the Formula (I), or a pharmaceutically acceptable salt thereof, as defined hereinbefore for use as a medicament in a warm-blooded animal such as man.

According to a further aspect of the invention, there is provided a compound of the Formula (I), or a pharmaceutically acceptable salt thereof, as defined hereinbefore for use in the production of an anti-proliferative effect in a warm-blooded animal such as man.

According to a further feature of this aspect of the invention there is provided a compound of the Formula (I), or a pharmaceutically acceptable salt thereof, as defined hereinbefore for use in a warm-blooded animal such as man as an anti-invasive agent in the containment and/or treatment of solid tumour disease.

According to a further aspect of the invention, there is provided the use of a compound of the Formula (I), or a pharmaceutically acceptable salt thereof, as defined hereinbefore for the production of an anti-proliferative effect in a warm-blooded animal such as man.

According to a further feature of this aspect of the invention there is provided the use of a compound of the Formula (I), or a pharmaceutically acceptable salt thereof, as defined hereinbefore in the manufacture of a medicament for use in the production of an anti-proliferative effect in a warm-blooded animal such as man.

According to a further feature of this aspect of the invention there is provided the use of a compound of the Formula (I), or a pharmaceutically acceptable salt thereof, as defined hereinbefore in the manufacture of a medicament for use in a warm-blooded animal such as man as an anti-invasive agent in the containment and/or treatment of solid tumour disease.

According to a further feature of this aspect of the invention there is provided a method for producing an anti-proliferative effect in a warm blooded animal, such as man, in need of such treatment which comprises administering to said animal an effective amount of a compound of the Formula (I), or a pharmaceutically acceptable salt thereof, as defined hereinbefore.

According to a further feature of this aspect of the invention there is provided a method for producing an anti-invasive effect by the containment and/or treatment of solid tumour disease in a warm blooded animal, such as man, in need of such treatment which comprises administering to said animal an effective amount of a compound of the Formula (I), or a pharmaceutically acceptable salt thereof, as defined hereinbefore.

According to a further aspect of the invention, there is provided a compound of the Formula (I), or a pharmaceutically acceptable salt thereof, as defined hereinbefore for use in the prevention or treatment of cancer in a warm blooded animal such as man.

According to a further aspect of the invention there is provided the use of a compound of the Formula (I), or a pharmaceutically acceptable salt thereof, as defined hereinbefore in the manufacture of a medicament for use in the prevention or treatment of cancer in a warm blooded animal such as man.

According to a further feature of this aspect of the invention there is provided a method for the prevention or treatment of cancer in a warm blooded animal such as man, in need of such treatment which comprises administering to said animal an effective amount of a compound of the Formula (I), or a pharmaceutically acceptable salt thereof, as defined hereinbefore.

According to a further aspect of the invention, there is provided a compound of the Formula (I), or a pharmaceutically acceptable salt thereof, as defined hereinbefore for use in the prevention or treatment of solid tumour disease in a warm blooded animal such as man.

According to a further aspect of the invention there is provided the use of a compound of the Formula (I), or a pharmaceutically acceptable salt thereof, as defined hereinbefore in the manufacture of a medicament for use in the prevention or treatment of solid tumour disease in a warm blooded animal such as man.

According to a further feature of this aspect of the invention there is provided a method for the prevention or treatment of solid tumour disease in a warm blooded animal, such as man, in need of such treatment which comprises administering to said animal an effective amount of a compound of the Formula (I), or a pharmaceutically acceptable salt thereof, as defined hereinbefore.

According to a further aspect of the invention there is provided a compound of the Formula (I), or a pharmaceutically acceptable salt thereof, as defined hereinbefore for use in the prevention or treatment of those tumours which are sensitive to inhibition of PI3K-α and/or -δ enzymes that are involved in the signal transduction steps which lead to the proliferation, survival, invasiveness and migratory ability of tumour cells.

According to a further feature of this aspect of the invention there is provided the use of a compound of the Formula (I), or a pharmaceutically acceptable salt thereof, as defined hereinbefore in the manufacture of a medicament for use in the prevention or treatment of those tumours which are sensitive to inhibition of PI3K-α and/or -δ enzymes that are involved in the signal transduction steps which lead to the proliferation, survival, invasiveness and migratory ability of tumour cells.

According to a further feature of this aspect of the invention there is provided a method for the prevention or treatment of those tumours which are sensitive to inhibition of PI3K-α and/or -δ enzymes that are involved in the signal transduction steps which lead to the proliferation, survival, invasiveness and migratory ability of tumour cells which comprises administering to said animal an effective amount of a compound of the Formula (I), or a pharmaceutically acceptable salt thereof, as defined hereinbefore.

According to a further aspect of the invention there is provided a compound of the Formula (I), or a pharmaceutically acceptable salt thereof, as defined hereinbefore for use in providing a PI3K-α and -δ enzyme inhibitory effect.

According to a further feature of this aspect of the invention there is provided the use of a compound of the Formula (I), or a pharmaceutically acceptable salt thereof, as defined hereinbefore in the manufacture of a medicament for use in providing a PI3K-α and -δ enzyme inhibitory effect.

According to a further aspect of the invention there is also provided a method for providing a PI3K-α and -δ enzyme inhibitory effect which comprises administering an effective amount of a compound of the Formula (I), or a pharmaceutically acceptable salt thereof, as defined hereinbefore.

As stated hereinbefore, certain compounds of the present invention possess substantially better potency against PI3K-α and -δ enzymes than against other PI3-kinase enzymes or other kinases. Such compounds possess sufficient potency against PI3K-α and -δ enzymes that they may be used in an amount sufficient to inhibit PI3K-α and -δ enzymes whilst demonstrating little activity against the PI3K-β enzyme and against most other kinase enzymes. Such compounds are likely to be useful for the selective inhibition of PI3K-α and -δ enzymes and are likely to be useful for the effective treatment of, for example PI3K-α and/or -δ enzyme driven tumours.

According to this aspect of the invention there is provided a compound of the Formula (I), or a pharmaceutically acceptable salt thereof, as defined hereinbefore for use in providing a selective PI3K-α and -δ enzyme inhibitory effect.

According to a further feature of this aspect of the invention there is provided the use of a compound of the Formula (I), or a pharmaceutically acceptable salt thereof, as defined hereinbefore in the manufacture of a medicament for use in providing a selective PI3K-α and -δ enzyme inhibitory effect.

According to a further aspect of the invention there is also provided a method for providing a selective PI3K-α and -δ enzyme inhibitory effect which comprises administering an effective amount of a compound of the Formula (I), or a pharmaceutically acceptable salt thereof, as defined hereinbefore.

By "a selective PI3K-α and -δ enzyme inhibitory effect" is meant that the compound of the Formula (I) are more potent against PI3K-α and -δ enzymes than against other class 1 PI3-kinases, and generally display good selectivity relative to other members of the wider PI3-kinase family and across the broader classes of kinase enzymes comprising tyrosine and ser/thr kinases.

According to a further feature of the invention there is provided a compound of the Formula (I), or a pharmaceutically acceptable salt thereof, as defined herein before for use in the treatment of cancer of the Breast, Stomach (Gastric) and Oesophagus cancers, Non Small Cell Lung Cancer (NSCLC) including squamous cell carcinomas (SCC) and adenocarcinoma, SCC of the Head and Neck (H&N), Gynaecological cancers (including Endometrial, Ovarian and Cervical) and of Haematological cancers such as multiple myeloma, lymphomas and leukemias (including Chronic Lymphoctyic Leukaemia (CLL), Acute Lymphoblastic Leukaemia (ALL) and Mantle Cell Lymphoma (MCL).

According to a further feature of this aspect of the invention there is provided a compound of the Formula (I), or a pharmaceutically acceptable salt thereof, as defined herein before for use in the treatment of cancer of the Bladder, Brain/CNS, Colorectum, Lung (all other forms), Gallbladder and Bile duct, and Skin.

According to a further feature of this aspect of the invention there is provided a compound of the Formula (I), or a pharmaceutically acceptable salt thereof, as defined herein before for use in the treatment of cancer of the Prostate, Bone, Kidney, Liver, Melanoma, Gastrointestinal tissue, Pancreas, Testes, Thyroid, Penile, Vulva, and other tumour types with a PI3-kinase dependency through mutation, amplification or other aberrations.

According to a further feature of this aspect of the invention there is provided a method for treating cancer of Breast, Stomach (Gastric) and Oesophagus cancers, NSCLC including SCC and adenocarcinoma, SCC of H&N, Gynaecological cancers (including Endometrial, Ovarian and Cervical) and of Haematological cancers such as multiple myeloma, lymphomas and leukemias (including CLL, ALL and MCL) in a warm blooded animal such as man that is in need of such treatment which comprises administering an effective amount of a compound of the Formula (I), or a pharmaceutically acceptable salt thereof, as defined hereinbefore.

According to a further feature of this aspect of the invention there is provided a method for treating cancer of Bladder, Brain/CNS, Colorectum, Lung (all other forms), Gallbladder and Bile duct, and Skin in a warm blooded animal such as man that is in need of such treatment which comprises administering an effective amount of a compound of the Formula (I), or a pharmaceutically acceptable salt thereof, as defined hereinbefore.

According to a further feature of this aspect of the invention there is provided a method for treating cancer of Prostate, Bone, Kidney, Liver, Melanoma, Gastrointestinal tissue, Pancreas, Testes, Thyroid, Penile, Vulva, and other tumour types with a PI3-kinase dependency through mutation, amplification or other aberrations, in a warm blooded animal such as man that is in need of such treatment which comprises administering an effective amount of a compound of the Formula (I), or a pharmaceutically acceptable salt thereof, as defined hereinbefore.

According to a further feature of the invention there is provided the use of a compound of the Formula (I), or a pharmaceutically acceptable salt thereof, as defined herein before in the manufacture of a medicament for use in the treatment of cancer of the Breast, Stomach (Gastric) and Oesophagus cancers, NSCLC including SCC and adenocarcinoma, SCC of H&N, Gynaecological cancers (including Endometrial, Ovarian and Cervical) and of Haematological cancers such as multiple myeloma, lymphomas and leukemias (including CLL, ALL and MCL).

According to a further feature of this aspect of the invention there is provided the use of a compound of the Formula (I), or a pharmaceutically acceptable salt thereof, as defined herein before in the manufacture of a medicament for use in the treatment of cancer of the Bladder, Brain/CNS, Colorectum, Lung (all other forms), Gallbladder and Bile duct, and Skin.

According to a further feature of this aspect of the invention there is provided the use of a compound of the Formula (I), or a pharmaceutically acceptable salt thereof, as defined herein before in the manufacture of a medicament for use in the treatment of cancer of the of Prostate, Bone, Kidney, Liver, Melanoma, Gastrointestinal tissue, Pancreas, Testes, Thyroid, Penile, Vulva, and other tumour types with a PI3-kinase dependency through mutation, amplification or other aberrations.

In one feature of the invention, the cancer to be treated is breast cancer. In a further aspect of this feature, the breast cancer is Estrogen Receptor +ve. In one embodiment of this aspect, the compound of Formula (I), or a pharmaceutically acceptable salt thereof, is dosed in combination with an anti-hormonal agent as defined herein. In another embodiment of this aspect, Example 3 is dosed in combination with an anti-hormonal agent as defined herein. In a further embodiment of this aspect, Example 3 is dosed in combination with olaparib, or a pharmaceutically-acceptable salt thereof, and optionally further in combination with an anti-hormonal agent as defined herein. In a further embodiment of this aspect, Example 3 is dosed in combination with AZD5363, or a pharmaceutically-acceptable salt thereof, and optionally further in combination with an anti-hormonal agent as defined herein.

In one aspect where the treatment of cancer is indicated, it is to be understood that this may refer to the prevention of metastases and the treatment of metastases, i.e. cancer spread. Therefore the compounds of the present invention might be used to treat a patient who has no metastases to stop them occurring, or to lengthen the time period before they occur, and to a patient who already has metastases to treat the metastases themselves. Furthermore the treatment of cancer may refer to treatment of an established primary tumour or tumours and developing primary tumour or tumours. Therefore, in one aspect the treatment of cancer relates to the prevention of metastases. In another aspect of the invention the treatment of cancer relates to the treatment of metastases. In another aspect of the invention the treatment of cancer relates to treatment of an established primary tumour or tumours or developing primary tumour or tumours.

As stated hereinbefore, the in vivo effects of a compound of the Formula (I) may be exerted in part by one or more metabolites (such as compounds of formula A as defined hereinbefore) that are formed within the human or animal body after administration of a compound of the Formula (I).

Particular compounds of the invention possess better potency against PI3-kinase-α and -δ than against other class I PI3-kinase isoforms such as -β and -γ. In one aspect the compounds of the invention are selective for PI3K-α and -δ compared to PI3K-β or -γ.

The present invention therefore also contemplates a method for inhibiting PI3-kinase-α in a patient, comprising administering to a patient an amount of the compound of Formula (I), or a pharmaceutically acceptable salt thereof, effective in inhibiting the phosphoinositide 3-kinase-α in the patient.

The present invention therefore also contemplates a method for inhibiting PI3-kinase-α and -δ in a patient, comprising administering to a patient an amount of the compound of Formula (I), or a pharmaceutically acceptable salt thereof, effective in inhibiting the PI3-kinase-α and -δ in the patient.

The compound of Formula (I), or a pharmaceutically acceptable salt thereof, being an inhibitor of PI3-kinase, also has potential therapeutic uses in a variety of other disease states. For example, PI3-kinase plays an important role in promoting smooth muscle proliferation in the vascular tree, i.e. vascular smooth muscle cells (Thyberg, European *Journal of Cell Biology*, 1998, 76(1), 33-42), and in the lungs (airway smooth muscle cells), Krymskaya, V. P., *BioDrugs*, 2007, 21(2), 85-95. Excessive proliferation of vascular smooth muscle cells plays an important role in the formation of atherosclerotic plaques and in the development of neointimal hyperplasia following invasive vascular procedures (Scwartz et al., *Progress in Cardiovascular Disease*, 1984, 26, 355-372; Clowes et al., *Laboratory Investigations*, 1978, 39, 141-150. Moreover, excessive proliferation of airway smooth muscle cells leads to the development of COPD in the setting of asthma and chronic bronchitis. Inhibitors of PI3-kinase activity therefore may be used to prevent vascular restenosis, atherosclerosis, and COPD.

PI3-kinase also plays an important role in leukocyte function (Fuller et al., *The Journal of Immunology*, 1999, 162(11), 6337-6340; Eder et al., *The Journal of Biological Chemistry*, 1998, 273(43), 28025-31) and lymphocyte function (Vicente-Manzanares et al., *The Journal of Immunology*, 1999, 163(7), 4001-4012). For example, leukocyte adhesion to inflamed endothelium involves activation of endogenous leukocyte integrins by a PI3-kinase-dependent signalling process. Furthermore, oxidative burst (Nishioka et al., *FEBS Letters*, 1998, 441(1), 63-66 and Condliffe, A. M., et al., *Blood* 2005, 106(4), 1432-40) and cytoskeletal reorganization (Kirsch et al., *Proceedings National Academy of Sciences USA*, 1999, 96(11), 6211-6216) in neutrophils appears to involve PI3-kinase signalling. Neutrophil migration and directional movement are also dependent on PI3-kinase activity (Camps, M., et al., *Nat Med*, 2005, 11(9), 936-43 and Sadhu, C. et al., *J Immunol*, 2003, 170(5), 2647-54). Thus, inhibitors of PI3-kinase may be useful in reducing leukocyte adhesion and activation at sites of inflammation and therefore may be used to treat acute and/or chronic inflammatory disorders. PI3-kinase also plays an important role in lymphocyte proliferation and activation, Fruman et al., *Science*, 1999, 283 (5400), 393-397. In particular, PI3K-δ is essential for B cell development and function, including IgM-specific antibody-induced B-cell proliferation (Okkenhaug K et al., *Science*, 2002, 297(5583), 1031-1034), B-cell-receptor-induced DNA synthesis and proliferation, and IL-4-induced survival (Bilancio A et al., *Blood*, 2006, 107, 642-650). These observations indicate that PI3K-δ has a crucial and non-redundant role in B-cell function that is not compensated by other class I PI3Ks. Given the important role of lymphocytes in auto-immune diseases, an inhibitor of PI3-kinase activity may be used in the treatment of such disorders (Rommel C, Camps M and Ji H, *Nat Rev Immunol*, 2007, 1038, 191-201).

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) antihormonal agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) inhibitors of growth factor function and their downstream signalling pathways: included are Ab modulators of any growth factor or growth factor receptor targets, reviewed by Stem et al. *Critical Reviews in Oncology/Haematology*, 2005, 54, pp 11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R;

also included are modulators which target signalling proteins in the wider PI3-kinase signalling pathway, for example, inhibitors of other PI3-kinase isoforms such as PI3K-β, and ser/thr kinases such as AKT, mTOR, PDK, SGK, PI4K or PIP5K;

also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors;

iv) modulators of DNA damage signalling pathways, for example PARP inhibitors (e.g. Olaparib), ATR inhibitors or ATM inhibitors;

v) modulators of apoptotic and cell death pathways such as Bcl family modulators (e.g. ABT-263/Navitoclax, ABT-199);

(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];

(vii) vascular damaging agents, such as Combretastatin A4;

(viii) anti-invasion agents, for example c-Src kinase family inhibitors like (dasatinib, *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558) or CTLA4 (e.g. ipilimumab and tremelimumab);

(x) Antisense or RNAi Based Therapies, for Example Those which are Directed to the Targets Listed.

(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

According to this aspect of the invention there is provided a combination suitable for use in the treatment of cancer comprising a compound of Formula (I) as defined hereinbefore or a pharmaceutically acceptable salt thereof and another anti-tumour agent, in particular any one of the anti tumour agents listed under (i)-(xi) above. In particular, the anti-tumour agent listed under (i)-(xi) above is the standard of care for the specific cancer to be treated; the person skilled in the art will understand the meaning of "standard of care".

Therefore in a further aspect of the invention there is provided a compound of Formula (I) or a pharmaceutically acceptable salt thereof in combination with another anti-tumour agent, in particular an anti-tumour agent selected from one listed under (i)-(xi) herein above.

In a further aspect of the invention there is provided a compound of Formula (I) or a pharmaceutically acceptable salt thereof in combination with another anti-tumour agent, in particular an anti-tumour agent selected from one listed under (i) above.

In a further aspect of the invention there is provided a combination suitable for use in the treatment of cancer comprising a compound of Formula (I) as defined hereinbefore or a pharmaceutically acceptable salt thereof and any one of the anti tumour agents listed under (i) above.

In a further aspect of the invention there is provided a combination suitable for use in the treatment of cancer comprising a compound of Formula (I) as defined hereinbefore or a pharmaceutically acceptable salt thereof and a taxoid, such as for example taxol or taxotere, conveniently taxotere.

In a further aspect of the invention there is provided a compound of Formula (I) or a pharmaceutically acceptable salt thereof in combination with another anti-tumour agent, in particular an anti-tumour agent selected from one listed under (ii) herein above.

In a further aspect of the invention there is provided a combination suitable for use in the treatment of cancer comprising a compound of Formula (I) as defined hereinbefore or a pharmaceutically acceptable salt thereof and any one of antihormonal agents listed under (ii) above, for example any one of the anti-oestrogens listed in (ii) above.

In a further aspect of the invention there is provided a compound of Formula (I) or a pharmaceutically acceptable salt thereof in combination with an mTOR inhibitor, such as those disclosed in WO2008/023161, for example

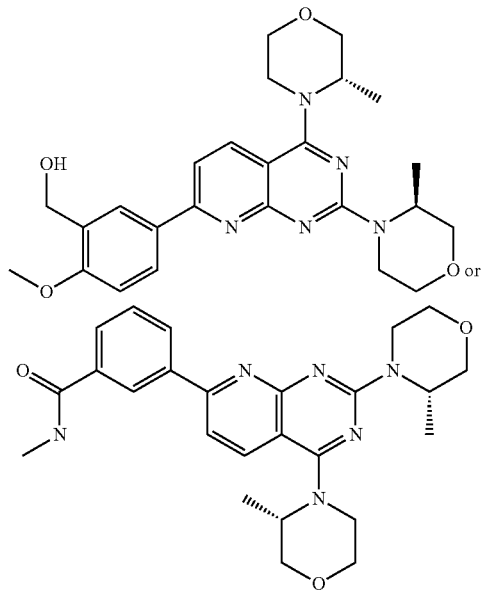

In a further aspect of the invention there is provided a combination suitable for use in the treatment of cancer comprising a compound of Formula (I) as defined hereinbefore or a pharmaceutically acceptable salt thereof and an mTOR inhibitor, such as those disclosed in WO2008/023161, for example

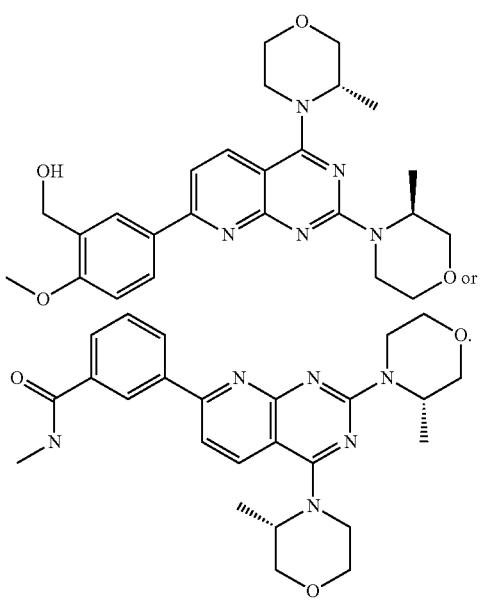

In particular, the mTOR inhibitor is AZD2014, which has the following structure:

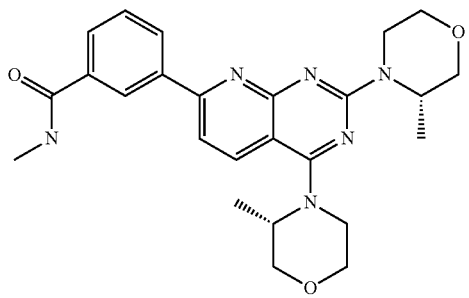 [SMILES: CNC(=O)c1cccc(-c2ccc3c(N4CCOC[C@@H]4C)nc(N4CCOC[C@@H]4C)nc3n2)c1]

In one aspect, the above combination of the compound of formula (I) and AZD2014 is suitable for use in the treatment of ER+ve breast cancer, optionally in combination with standard of care hormonal therapy.

In a further aspect of the invention there is provided a compound of Formula (I) or a pharmaceutically acceptable salt thereof in combination with an inhibitor of PI3K-β.

The combination of a compound of formula (I) with an inhibitor of PI3K-β may be particularly useful in the treatment of tumours, for example, prostate, breast (for example triple negative breast), squamous cell NSCLC and renal cancer, with a background of PTEN loss.

In a further aspect of the invention there is provided a combination suitable for use in the treatment of cancer comprising a compound of Formula (I) as defined hereinbefore or a pharmaceutically acceptable salt thereof and an inhibitor of PI3K-β.

In one aspect, the inhibitors of PI3K-β described herein also have some PI3K-δ inhibitory activity.

In a further aspect of the invention there is provided a compound of Formula (I) or a pharmaceutically acceptable salt thereof in combination with an inhibitor of PI3K-β, such as any one of the examples in International patent application WO2011/051704.

In a further aspect of the invention there is provided a combination suitable for use in the treatment of cancer comprising a compound of Formula (I) as defined hereinbefore or a pharmaceutically acceptable salt thereof and an inhibitor of PI3K-β, such as anyone of the examples in International patent application WO2011/051704.

In a further aspect of the invention there is provided a compound of Formula (I) or a pharmaceutically acceptable salt thereof in combination with an inhibitor of PI3K-β and PI3K-δ, such as 8-((1R)-1-(3,5-difluorophenylamino)ethyl)-N,N-dimethyl-2-morpholino-4-oxo-4H-chromene-6-carboxamide (example 3.06b in International patent application WO2011/051704, also known as AZD8186) or a pharmaceutically-acceptable salt thereof:

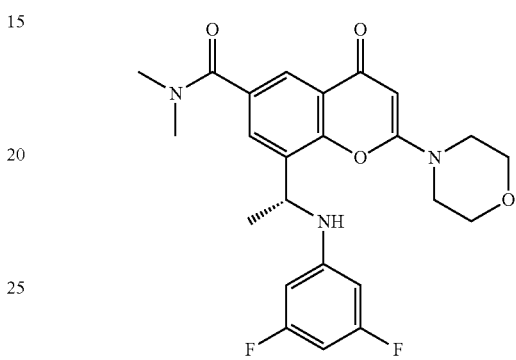

In a further aspect of the invention there is provided a combination suitable for use in the treatment of cancer comprising a compound of Formula (I) as defined hereinbefore or a pharmaceutically acceptable salt thereof and an inhibitor of PI3K-β and PI3K-δ, such as 8-((1R)-1-(3,5-difluorophenylamino)ethyl)-N,N-dimethyl-2-morpholino-4-oxo-4H-chromene-6-carboxamide (example 3.06b in International patent application WO2011/051704, also known as AZD8186) or a pharmaceutically-acceptable salt thereof:

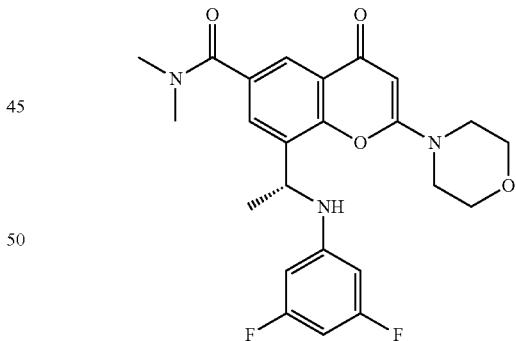

In a further aspect of the invention there is provided a compound of Formula (I) or a pharmaceutically acceptable salt thereof in combination with an inhibitor of AKT kinase, such as (S)-4-amino-N-(1-(4-chlorophenyl)-3-hydroxypropyl)-1-(7H-pyrrolo[2,3-d]pyrimidin-4-yl)piperidine-4-carboxamide (AZD5363) or a pharmaceutically-acceptable salt thereof (see for example WO2009/047563).

The combination of a compound of Formula (I) and an AKT inhibitor may be particularly useful in treating tumours with a higher prevalence of mutation in PIK3CA gene, such as ER+ve breast cancer, endometrial, ovarian, squamous cell NSCLC, gastric, bladder and biliary tract cancer.

In a further aspect of the invention there is provided a combination suitable for use in the treatment of cancer comprising a compound of Formula (I) as defined hereinbefore or a pharmaceutically acceptable salt thereof and an inhibitor of AKT kinase, such as (S)-4-amino-N-(1-(4-chlorophenyl)-3-hydroxypropyl)-1-(7H-pyrrolo[2,3-d]pyrimidin-4-yl)piperidine-4-carboxamide (AZD5363) or a pharmaceutically-acceptable salt thereof (see for example WO2009/047563).

In a further aspect of the invention there is provided a compound of Formula (I) or a pharmaceutically acceptable salt thereof in combination with olaparib (4-[3-(4-cyclopropanecarbonyl-piperazine-1-carbonyl)-4-fluoro-benzyl]-2H-phthalazin-1-one) or a pharmaceutically-acceptable salt thereof.

The combination of a compound of Formula (I) and olaparib may be particularly useful both in triple negative breast cancer, either BRCA wild type or deficient, and in estrogen receptor positive (ER+ve) breast cancer, particularly those with mutations in the PIK3CA gene.

In a further aspect of the invention there is provided a combination suitable for use in the treatment of cancer comprising a compound of Formula (I) as defined hereinbefore or a pharmaceutically acceptable salt thereof and olaparib (4-[3-(4-cyclopropanecarbonyl-piperazine-1-carbonyl)-4-fluoro-benzyl]-2H-phthalazin-1-one) or a pharmaceutically-acceptable salt thereof.

Particular combinations of the invention comprise any one of the compounds of the Examples herein (or a pharmaceutically acceptable salt thereof) and an mTOR inhibitor, PI3Kβ inhibitor, inhibitor of AKT kinase or olaparib as described hereinabove. Further particular combinations of the invention comprise Example 3 (or a pharmaceutically acceptable salt thereof) and an mTOR inhibitor, PI3Kβ inhibitor, inhibitor of AKT kinase or olaparib as described hereinabove. Further particular combinations of the invention comprise Example 3 (or a pharmaceutically acceptable salt thereof) and a PI3Kβ inhibitor, inhibitor of AKT kinase or olaparib (or a pharmaceutically-acceptable salt of any one of these three), as described hereinabove. Still further particular examples of combinations of the invention comprise Example 3 (or a pharmaceutically acceptable salt thereof) and any one of AZD8186, AZD5363 and olaparib (or a pharmaceutically-acceptable salt of any one of these three). Another example of a combination of the invention comprises Example 3 and AZD2014.

In all of the above combinations, it will be understood that the combination may also be dosed with standard of care treatment, as understood by the skilled person, such as other treatments from (i) to (xi) hereinbefore. For example, when it is intended to use any of the above combinations for the treatment of ER+ve breast cancer, standard of care hormonal therapy (such as those agents listed under (ii) above) may be used in conjunction with the combination of the invention. In other aspects, suitably the standard of care may be selected from (i) above.

Therefore in a further aspect of the invention, there is provided a triple combination suitable for use in the treatment of cancer
  a) a compound of formula (I) (such as Example 3) or a pharmaceutically-acceptable salt thereof;
  b) an mTOR inhibitor, PI3Kβ inhibitor, inhibitor of AKT kinase or olaparib or a pharmaceutically-acceptable salt thereof; and
  c) standard of care therapy for the cancer to be treated.

Suitably standard of care therapy may be dosed according to its usual dosing regimen, as understood by the skilled person.

According to a further aspect of the invention there is provided a pharmaceutical composition which comprises a compound of Formula (I) or a pharmaceutically acceptable salt thereof in combination with an anti-tumour agent selected from one listed under (i)-(xi) herein above, in association with a pharmaceutically acceptable diluent or carrier.

According to a further aspect of the invention there is provided a pharmaceutical composition which comprises Example 3 or a pharmaceutically acceptable salt thereof in combination with an anti-tumour agent selected from one listed under (i)-(xi) herein above, in association with a pharmaceutically acceptable diluent or carrier.

According to a further aspect of the invention there is provided a pharmaceutical composition which comprises Example 3 or a pharmaceutically acceptable salt thereof in combination with AZD5363, AZD8186 or olaparib, (or a pharmaceutically-acceptable salt of any one of these three) in association with a pharmaceutically acceptable diluent or carrier.

According to a further aspect of the invention there is provided a pharmaceutical composition which comprises a compound of Formula (I) or a pharmaceutically acceptable salt thereof in combination with an anti-tumour agent selected from one listed under (i)-(xi) herein above, in association with a pharmaceutically acceptable diluent or carrier for use in treating cancer.

According to a further aspect of the invention there is provided a pharmaceutical composition which comprises Example 3 or a pharmaceutically acceptable salt thereof in combination with an anti-tumour agent selected from one listed under (i)-(xi) herein above, in association with a pharmaceutically acceptable diluent or carrier for use in treating cancer.

According to a further aspect of the invention there is provided a pharmaceutical composition which comprises Example 3 or a pharmaceutically acceptable salt thereof in combination with AZD5363, AZD8186 or olaparib, (or a pharmaceutically-acceptable salt of any one of these three) in association with a pharmaceutically acceptable diluent or carrier for use in treating cancer.

According to another feature of the invention there is provided the use of a compound of the Formula (I) or a pharmaceutically acceptable salt thereof in combination with an anti-tumour agent selected from one listed under (i)-(xi) herein above, in the manufacture of a medicament for use in cancer in a warm-blooded animal, such as man.

According to another feature of the invention there is provided the use of Example 3 or a pharmaceutically acceptable salt thereof in combination with an anti-tumour agent selected from one listed under (i)-(xi) herein above, in the manufacture of a medicament for use in cancer in a warm-blooded animal, such as man.

According to another feature of the invention there is provided the use of Example 3 or a pharmaceutically acceptable salt thereof in combination with AZD5363, AZD8186 or olaparib, (or a pharmaceutically-acceptable salt of any one of these three) in the manufacture of a medicament for use in cancer in a warm-blooded animal, such as man.

Therefore in an additional feature of the invention, there is provided a method of treating cancer in a warm-blooded animal, such as man, in need of such treatment which comprises administering to said animal an effective amount of a compound of Formula (I) or a pharmaceutically acceptable salt thereof in combination with an anti-tumour agent selected from one listed under (i)-(xi) herein above.

Therefore in an additional feature of the invention, there is provided a method of treating cancer in a warm-blooded animal, such as man, in need of such treatment which comprises administering to said animal an effective amount of Example 3 or a pharmaceutically acceptable salt thereof in combination with an anti-tumour agent selected from one listed under (i)-(xi) herein above.

Therefore in an additional feature of the invention, there is provided a method of treating cancer in a warm-blooded animal, such as man, in need of such treatment which comprises administering to said animal an effective amount of Example 3 or a pharmaceutically acceptable salt thereof in combination with AZD5363, AZD8186 or olaparib (or a pharmaceutically-acceptable salt of any one of these three).

According to a further aspect of the present invention there is provided a kit comprising a compound of Formula (I) or a pharmaceutically acceptable salt thereof in combination with an anti-tumour agent selected from one listed under (i)-(xi) herein above.

According to a further aspect of the present invention there is provided a kit comprising:
a) a compound of Formula (I) or a pharmaceutically acceptable salt thereof in a first unit dosage form;
b) an anti-tumour agent selected from one listed under (i)-(xi) herein above in a second unit dosage form; and
c) container means for containing said first and second dosage forms.

According to a further aspect of the present invention there is provided a kit comprising:
a) a compound of Formula (I) or a pharmaceutically acceptable salt thereof in a first unit dosage form;
b) an anti-tumour agent selected from one listed under (i)-(xi) herein above in a second unit dosage form;
c) container means for containing said first and second dosage forms; and optionally
d) instructions for use.

According to a further aspect of the present invention there is provided a kit comprising:
a) a compound of Formula (I) or a pharmaceutically acceptable salt thereof in a first unit dosage form;
b) an mTOR inhibitor, such as those disclosed in WO2008/023161, for example

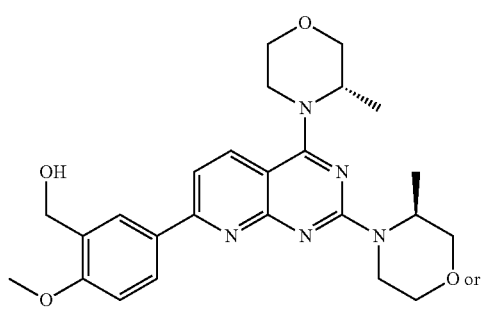

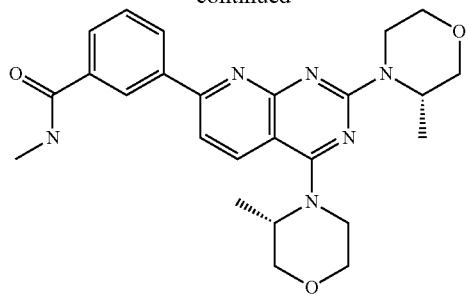

in a second unit dosage form; and
c) container means for containing said first and second dosage forms.

According to a further aspect of the present invention there is provided a kit comprising:
a) a compound of Formula (I) or a pharmaceutically acceptable salt thereof in a first unit dosage form;
b) an inhibitor of PI3K-β, such as any one of the examples in International patent application WO2011/051704, or a pharmaceutically acceptable salt thereof in a second unit dosage form; and
c) container means for containing said first and second dosage forms.

According to a further aspect of the present invention there is provided a kit comprising:
a) a compound of Formula (I) or a pharmaceutically acceptable salt thereof in a first unit dosage form;
b) an inhibitor of PI3K-β, such as any one of the examples in International patent application WO2011/051704, or a pharmaceutically acceptable salt thereof in a second unit dosage form;
c) container means for containing said first and second dosage forms; and optionally
d) instructions for use.

According to a further aspect of the present invention there is provided a kit comprising:
a) a compound of Formula (I) or a pharmaceutically acceptable salt thereof in a first unit dosage form;
b) an inhibitor of PI3K-β and PI3K-δ which is 8-((1R)-1-(3,5-difluorophenylamino)ethyl)-N,N-dimethyl-2-morpholino-4-oxo-4H-chromene-6-carboxamide (example 3.06b in International patent application WO2011/051704, also known as AZD8186), or a pharmaceutically acceptable salt thereof in a second unit dosage form; and
c) container means for containing said first and second dosage forms.

According to a further aspect of the present invention there is provided a kit comprising:
a) a compound of Formula (I) or a pharmaceutically acceptable salt thereof in a first unit dosage form;
b) an inhibitor of PI3K-β and PI3K-δ which is 8-((1R)-1-(3,5-difluorophenylamino)ethyl)-N,N-dimethyl-2-morpholino-4-oxo-4H-chromene-6-carboxamide (example 3.06b in International patent application WO2011/051704, also known as AZD8186), or a pharmaceutically acceptable salt thereof in a second unit dosage form;
c) container means for containing said first and second dosage forms; and optionally
d) instructions for use.

According to a further aspect of the present invention there is provided a kit comprising:
a) a compound of Formula (I) or a pharmaceutically acceptable salt thereof in a first unit dosage form;

b) an inhibitor of AKT kinase, such as (S)-4-amino-N-(1-(4-chlorophenyl)-3-hydroxypropyl)-1-(7H-pyrrolo[2,3-d]pyrimidin-4-yl)piperidine-4-carboxamide or a pharmaceutically-acceptable salt thereof (AZD5363, see for example WO2009/047563), in a second unit dosage form;
c) container means for containing said first and second dosage forms; and optionally
d) instructions for use.

According to a further aspect of the present invention there is provided a kit comprising:
a) a compound of Formula (I) or a pharmaceutically acceptable salt thereof in a first unit dosage form;
b) an inhibitor of AKT kinase, such as (S)-4-amino-N-(1-(4-chlorophenyl)-3-hydroxypropyl)-1-(7H-pyrrolo[2,3-d]pyrimidin-4-yl)piperidine-4-carboxamide or a pharmaceutically-acceptable salt thereof (AZD5363, see for example WO2009/047563), in a second unit dosage form; and
c) container means for containing said first and second dosage forms.

According to a further aspect of the present invention there is provided a kit comprising:
a) a compound of Formula (I) or a pharmaceutically acceptable salt thereof in a first unit dosage form;
b) an inhibitor of AKT kinase, such as (S)-4-amino-N-(1-(4-chlorophenyl)-3-hydroxypropyl)-1-(7H-pyrrolo[2,3-d]pyrimidin-4-yl)piperidine-4-carboxamide or a pharmaceutically-acceptable salt thereof (AZD5363, see for example WO2009/047563), in a second unit dosage form;
c) container means for containing said first and second dosage forms; and optionally
d) instructions for use.

According to a further aspect of the present invention there is provided a kit comprising:
a) a compound of Formula (I) or a pharmaceutically acceptable salt thereof in a first unit dosage form;
b) olaparib (4-[3-(4-cyclopropanecarbonyl-piperazine-1-carbonyl)-4-fluoro-benzyl]-2H-phthalazin-1-one) or a pharmaceutically acceptable salt thereof, in a second unit dosage form; and
c) container means for containing said first and second dosage forms.

According to a further aspect of the present invention there is provided a kit comprising:
a) a compound of Formula (I) or a pharmaceutically acceptable salt thereof in a first unit dosage form;
b) olaparib (4-[3-(4-cyclopropanecarbonyl-piperazine-1-carbonyl)-4-fluoro-benzyl]-2H-phthalazin-1-one) or a pharmaceutically acceptable salt thereof, in a second unit dosage form;
c) container means for containing said first and second dosage forms; and optionally
d) instructions for use.

In all of the above combinations, uses, methods of treatment and kits, AZD5363, AZD8186 and olaparib may be in the form of free bases or in the form of a pharmaceutically-acceptable salt. Therefore in one embodiment AZD5363 is in the form of a free base; in a further embodiment AZD5363 is in the form of a pharmaceutically-acceptable salt. In another embodiment AZD8186 is in the form of a free base; in a further embodiment AZD8186 is in the form of a pharmaceutically-acceptable salt. In another embodiment olaparib is in the form of a free base; in a further embodiment olaparib is in the form of a pharmaceutically-acceptable salt.

Although the compounds of the Formula (I) are primarily of value as therapeutic agents for use in warm-blooded animals (including man), they are also useful whenever it is required to inhibit the effects of PI3-kinase-α and -δ. Thus, they are useful as pharmacological standards for use in the development of new biological tests and in the search for new pharmacological agents.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect.

In one embodiment sequential treatment involves administration of each component of the combination within a period of 11 days. In another embodiment this period is 10 days. In another embodiment this period is 9 days. In another embodiment this period is 8 days. In another embodiment this period is 7 days. In another embodiment this period is within 6 days. In another embodiment this period is within 5 days. In another embodiment this period is within 4 days. In another embodiment this period is within 3 days. In another embodiment this period is within 2 days. In another embodiment this period is within 24 hours. In another embodiment this period is within 12 hours.

Sequential and co-administration are both exemplified herein in the combination experiments with Example 3 and AZD5363 in BT474 model. In this example, sequential administration is illustrated by dosing AZD5363 for 2 days followed by Example 3 for 2 days, then 3 days with no dose of either agent before the pattern is repeated ("dosage cycle"). Co-administration is illustrated with a dosing regimen where both AZD5363 and Example 3 are dosed for 2 days, followed by 5 days with no dose of either agent. In these two examples, sequential administration appears to be more effective in causing tumour regression, illustrating the potential importance of optimising the regimen. Further potential co-dosing regimens include:
1) a dosage cycle where both AZD5363 and Example 3 are dosed for 2 days, followed by 3 days with no dose of either agent;
2) a dosage cycle where both AZD5363 and Example 3 are dosed for 3 days, followed by 4 days with no dose of either agent;
3) a dosage cycle where both AZD5363 and Example 3 are dosed for 4 days, followed by 3 days with no dose of either agent;
4) a dosage cycle where both AZD5363 and Example 3 are dosed for 5 days, followed by 2 days with no dose of either agent
5) a dosage cycle where AZD5363 and Example 3 are dosed every other day
6) a dosage cycle where AZD5363 and Example 3 are dosed every three days
7) a dosage cycle where AZD5363 and Example 3 on dosed on a weekly schedule with 3 and 4 day gaps between dosing (e.g. Monday/Thursday)
8) a dosage cycle where AZD5363 and Example 3 are dosed on a weekly schedule with 2 and 3 days gaps between dosing (e.g. Monday/Wednesday/Friday)

Combinations of compounds of formula (I), particularly Example 3, with an mTOR inhibitor, such as AZD2014 or a PI3K-β inhibitor (such as the β/δ inhibitor AZD8186) may suitably be dosed in a similar regimen to those described above for the combination of Example 3 and AZD5363.

A combination of a compound of formula (I) and olaparib may be dosed according to a regimen where olaparib is dosed daily and the compound of formula (I) is dosed according to an intermittent dosing schedule (such as for example 2 days dosing followed by 3 to 5 days with no dose).

Each of these illustrative dosing regimes comprise a further aspect of the invention. Each of these illustrative dosing regimes may also be applied to combinations with other anti-tumour agents listed in (i) to (xi) above.

It may be advantageous, within a given dosage cycle, to administer one specific component of the combination before the other—i.e. sequential dosing.

Therefore, in one embodiment the sequential administration comprises the sequential administration of the compound of formula (I) (particularly Example 3) prior to the administration of the other anti-tumour agent listed in (i) to (xi) above, particularly an anti-tumour agent selected from AZD5363, AZD8186 and olaparib, within a dosage cycle.

In another embodiment the sequential administration comprises the sequential administration of the anti-tumour agent listed in (i) to (xi) above, particularly an anti-tumour agent selected from AZD5363, AZD8186 and olaparib, prior to the administration of compound of formula (I) (particularly Example 3) within a dosage cycle.

In one embodiment, the anti-tumour agent listed in (i) to (xi) above and the compound of formula (I) are dosed up to 2 days apart. In another embodiment, the anti-tumour agent listed in (i) to (xi) above and the compound of formula (I) are dosed up to 1 day apart. In another embodiment, the anti-tumour agent listed in (i) to (xi) above and the compound of formula (I) are dosed up to 18 hours apart. In another embodiment, the anti-tumour agent listed in (i) to (xi) above and the compound of formula (I) are dosed up to 12 hours apart. In another embodiment, the anti-tumour agent listed in (i) to (xi) above and the compound of formula (I) are dosed up to 6 hours apart. In another embodiment, the anti-tumour agent listed in (i) to (xi) above and the compound of formula (I) are dosed up to 3 hours apart.

In further embodiments the dosage cycle may be from 5 to 10 days in length.

In further embodiments the dosage cycle may be from 6 to 10 days in length.

In further embodiments the dosage cycle may be from 7 to 9 days in length.

In further embodiments the dosage cycle may be from 6 to 8 days in length.

In further embodiments the dosage cycle may be 10 days in length.

In further embodiments the dosage cycle may be 9 days in length.

In further embodiments the dosage cycle may be 8 days in length.

In further embodiments the dosage cycle may be 7 days in length.

In further embodiments the dosage cycle may be 6 days in length.

In further embodiments the dosage cycle may be 5 days in length.

In further embodiments the dosage cycle may involve the compound of formula (I) (particularly Example 3) being dosed for 2-4 consecutive days and not being dosed for the other days within a dosage cycle of 6 to 9 days in length.

In further embodiments the dosage cycle may involve the compound of formula (I) (particularly Example 3) being dosed for 3-4 consecutive days and not being dosed for the other days within a dosage cycle of 6 to 9 days in length; (for example, 7 days in length).

In further embodiments the dosage cycle may involve the compound of formula (I) (particularly Example 3) being dosed for 3-5 consecutive days and not being dosed for the other days within a dosage cycle of 7 to 10 days in length.

In further embodiments the dosage cycle may involve the compound of formula (I) (particularly Example 3) being dosed for 5 consecutive days and not being dosed for the other days within a dosage cycle of 6 to 9 days in length.

In further embodiments the dosage cycle may involve the compound of formula (I) (particularly Example 3) being dosed for 4 consecutive days and not being dosed for the other days within a dosage cycle of 6 to 9 days in length; (for example, 7 days in length).

In further embodiments the dosage cycle may involve the compound of formula (I) (particularly Example 3) being dosed for 3 consecutive days and not being dosed for the other days within a dosage cycle of 6 to 9 days in length.

Dosage cycles may be separated by a number of days where none of the active combination components are administered.

Combination therapy as described above may be added on top of standard of care therapy typically carried out according to its usual prescribing dosage schedule.

Personalised Healthcare

Another aspect of the present invention is based on identifying a link between the status of the gene encoding phosphoinositide-3-kinase, catalytic, alpha polypeptide (PIK3CA) and susceptibility to treatment with a compound of Formula (I). This therefore provides opportunities, methods and tools for selecting patients for treatment with a compound of Formula (I), particularly cancer patients, and/or avoiding treatment of patients less likely to respond therapeutically to the treatment thus avoiding unnecessary treatment and any side effects that may be associated with such ineffective treatment.

The present invention relates to patient selection tools and methods (including personalised medicine). The selection is based on whether the tumour cells to be treated possess wild-type or mutant PIK3CA gene. The PIK3CA gene status can therefore be used as a biomarker of susceptibility to treatment with a PI3K-α and -δ inhibitor.

There is a clear need for biomarkers that will enrich for or select patients whose tumours will respond to treatment with a PI3K-α and -δ inhibitor, such as a compound of Formula (I). Patient selection biomarkers that identify the patients most likely to respond to an agent are ideal in the treatment of cancer, since they reduce the unnecessary treatment of patients with non-responding tumours to the potential side effects of such agents.

A biomarker can be described as "a characteristic that is objectively measured and evaluated as an indicator of normal biologic processes, pathogenic processes, or pharmacologic responses to a therapeutic intervention". A biomarker is any identifiable and measurable indicator associated with a particular condition or disease where there is a correlation between the presence or level of the biomarker and some aspect of the condition or disease (including the presence of, the level or changing level of, the type of, the stage of, the susceptibility to the condition or disease, or the responsiveness to a drug used for treating the condition or disease). The correlation may be qualitative, quantitative, or both qualitative and quantitative. Typically a biomarker is a compound, compound fragment or group of compounds. Such compounds may be any compounds found in or produced by an organism, including proteins (and peptides), nucleic acids and other compounds.

Biomarkers may have a predictive power, and as such may be used to predict or detect the presence, level, type or stage of particular conditions or diseases (including the presence or level of particular microorganisms or toxins), the susceptibility (including genetic susceptibility) to particular conditions or diseases, or the response to particular treatments (including drug treatments). It is thought that biomarkers will play an increasingly important role in the future of drug discovery and development, by improving the efficiency of research and development programs. Biomarkers can be used as diagnostic agents, monitors of disease progression, monitors of treatment and predictors of clinical outcome. For example, various biomarker research projects are attempting to identify markers of specific cancers and of specific cardiovascular and immunological diseases. It is believed that the development of new validated biomarkers will lead both to significant reductions in healthcare and drug development costs and to significant improvements in treatment for a wide variety of diseases and conditions.

In order to optimally design clinical trials and to gain the most information from these trials, a biomarker may be required. The marker may be measurable in surrogate and tumour tissues. Ideally these markers will also correlate with efficacy and thus could ultimately be used for patient selection.

Thus, the technical problem underlying this aspect of the present invention is the identification of means for stratification of patients for treatment with a compound of Formula (I). The technical problem is solved by provision of the embodiments characterized in the claims and/or description herein.

As detailed in the examples herein, it was found that cells that possess a mutation in the PIK3CA are generally more susceptible to growth inhibition by the compound of Formula (I).

The invention provides a method of determining sensitivity of cells to a compound of Formula (I). The method comprises determining the status of PIK3CA gene in said cells. The cells are identified as likely to be sensitive to a compound of Formula I if the cells possess a mutated PIK3CA gene. Those patients with a mutated PIK3CA gene are therefore predicted to be particularly susceptible to treatment with a compound of Formula (I). A cell is defined as sensitive to a compound of Formula (I) if it inhibits the increase in cell number in a cell growth assay (either through inhibition of cell proliferation and/or through increased cell death). Methods of the invention are useful for predicting which cells are more likely to respond to a compound of Formula (I) by growth inhibition.

The present invention is further based, in part, on methods that can be used to determine a patient's responsiveness to a compound of Formula (I) including determining whether to administer a compound of Formula (I). Specifically the methods of the present invention include the determination of the gene status of PIK3CA. The presence of a mutated PIK3CA gene indicates that the tumour cells are more likely to respond by growth inhibition when contacted with a compound of Formula (I). The PIK3CA gene status can therefore be used to select patients for treatment with a compound of Formula (I).

Furthermore an in vitro method for the identification of a patient likely to be sensitive to a compound of Formula (I) is disclosed. Also disclosed are uses of an oligo- or polynucleotide primers or probes capable of detecting the mutation status of PIK3CA gene is provided. Also disclosed are use of 'kits for the detection of PIK3CA mutations, including but not limited to, the PIK3CA mutation detection kits marketed by diagnostic companies including Qiagen and Roche Molecular Systems. In another embodiment, the invention pertains to an in vitro method for determining whether a patient suffering from cancer is likely to be a responder to a pharmaceutical treatment with a compound of Formula (I), said method comprising the steps of: (i) obtaining a sample representative of the tumour that was previously collected from said patient; and, (ii) determining whether the PIK3CA genes contain a mutation in said sample. A mutation in PIK3CA gene is indicative of increased likelihood of a response to treatment with a compound of Formula (I). As a single gene biomarker test, identification of tumours that contain a PIK3CA mutation will enrich for response to a compound of Formula (I). Individual tumours that contain a PIK3CA mutation have the greatest likelihood of responding to a compound of Formula (I).

A sample "representative of the tumour" can be the actual tumour sample isolated, or may be a sample that has been further processed, e.g. a sample of PCR amplified nucleic acid from the tumour sample.

DEFINITIONS

In this Personalised Healthcare section:

"Allele" refers to a particular form of a genetic locus, distinguished from other forms by its particular nucleotide or amino acid sequence.

"Amplification reactions" are nucleic acid reactions which result in specific amplification of target nucleic acids over non-target nucleic acids. The polymerase chain reaction (PCR) is a well known amplification reaction.

"Cancer" is used herein to refer to neoplastic growth arising from cellular transformation to a neoplastic phenotype. Such cellular transformation often involves genetic mutation.

"Gene" is a segment of DNA that contains all the information for the regulated biosynthesis of an RNA product, including a promoter, exons, introns, and other sequence elements which may be located within 5' or 3' flanking regions (not within the transcribed portions of the gene) that control expression.

"Gene status" refers to whether the gene is wild type or not (i.e. mutant).

"Label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

"Non-synonymous variation" refers to a variation (variance) in or overlapping the coding sequence of a gene that result in the production of a distinct (altered) polypeptide sequence. These variations may or may not affect protein function and include missense variants (resulting in substitution of one amino acid for another), nonsense variants (resulting in a truncated polypeptide due to generation of a premature stop codon) and insertion/deletion variants.

"Synonymous variation" refers to a variation (variance) in the coding sequence of a gene that does not affect sequence of the encoded polypeptide. These variations may affect protein function indirectly (for example by altering expression of the gene), but, in the absence of evidence to the contrary, are generally assumed to be innocuous.

"Nucleic acid" refers to single stranded or double stranded DNA and RNA molecules including natural nucleic acids found in nature and/or modified, artificial nucleic acids having modified backbones or bases, as are known in the art.

"Primer" refers to a single stranded DNA oligonucleotide sequence capable of acting as a point of initiation for synthesis of a primer extension product which is complementary to the nucleic acid strand to be copied. The length and sequence of the primer must be such that they are able to prime the synthesis of extension products. A typical primer contains at least about 7 nucleotides in length of a sequence substantially complementary to the target sequence, but somewhat longer primers are preferred. Usually primers contain about 15-26 nucleotides, but longer or shorter primers may also be employed.

"Polymorphic site" is a position within a locus at which at least two alternative sequences are found in a population.

"Polymorphism" refers to the sequence variation observed in an individual at a polymorphic site. Polymorphisms include nucleotide substitutions, insertions, deletions and microsatellites and may, but need not, result in detectable differences in gene expression or protein function. In the absence of evidence of an effect on expression or protein function, common polymorphisms, including non-synonomous variants, are generally considered to be included in the definition of wild-type gene sequence. A catalog of human polymorphisms and associated annotation, including validation, observed frequencies, and disease association, is maintained by NCBI. Please note that the term "polymorphism" when used in the context of gene sequences should not be confused with the term "polymorphism" when used in the context of solid state form of a compound, that is the crystalline or amorphous nature of a compound. The skilled person will understand the intended meaning by its context.

"Probe" refers to single stranded sequence-specific oligonucleotides which have a sequence that is exactly complementary to the target sequence of the allele to be detected.

"Response" is defined by measurements taken according to Response Evaluation Criteria in Solid Tumours (RECIST) involving the classification of patients into two main groups: those that show a partial response or stable disease and those that show signs of progressive disease.

"Stringent hybridisation conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulphate, and 20 pg/ml denatured, sheared salmon sperm DNA, followed by washing the filters in 0.1×SSC at about 65° C.

"Survival" encompasses a patients' overall survival and progression-free survival.

"Overall survival" (OS) is defined as the time from the initiation of drug administration to death from any cause. "Progression-free survival" (PFS) is defined as the time from the initiation of drug administration to first appearance of progressive disease or death from any cause.

According to one aspect of the invention there is provided a method for selecting a patient for treatment with a compound of Formula (I), the method comprising providing a tumour cell containing sample from a patient; determining whether the PIK3CA gene in the patient's tumour cell containing sample is wild type or mutant; and selecting a patient for treatment with a compound of Formula (I) based thereon.

The method may include or exclude the actual patient sample isolation step. Thus, according to one aspect of the invention there is provided a method for selecting a patient for treatment with a compound of Formula (I), the method comprising determining whether the PIK3CA gene in a tumour cell containing sample previously isolated from the patient is wild type or mutant; and selecting a patient for treatment with a compound of Formula (I) based thereon.

In one embodiment, the patient is selected for treatment with a compound of Formula (I) if the tumour cell DNA has a mutant PIK3CA gene. In other embodiments, a patient whose tumour cell DNA possesses a wild type PIK3CA gene is not selected for treatment with a compound of Formula (I).

According to another aspect of the invention there is provided a method for predicting a patient's responsiveness to a compound of Formula (I), the method comprising determining whether the PIK3CA gene in the patient's tumour cells is wild type or mutant and based thereon, predicting a patient's responsiveness to treatment with a compound of Formula (I).

According to another aspect of the invention there is provided a method for determining the likelihood of effectiveness of treatment with a compound of formula I in a human patient affected with cancer comprising: determining whether the PIK3CA gene(s) in the patient's tumour cells is wild type or mutant and based thereon, predicting a patient's responsiveness to treatment with a compound of Formula (I).

For the purpose of this invention, a gene status of wild-type is meant to indicate normal or appropriate expression of the gene and normal function of the encoded protein. In contrast, mutant status is meant to indicate abnormal or inappropriate gene expression, or expression of a protein with altered function, consistent with the known roles of mutant PIK3CA in cancer (as described herein). Any number of genetic or epigenetic alterations, including but not limited to mutation, amplification, deletion, genomic rearrangement, or changes in methylation profile, may result in a mutant status. However, if such alterations nevertheless result in appropriate expression of the normal protein, or a functionally equivalent variant, then the gene status is regarded as wild-type. Examples of variants that typically would not result in a functional mutant gene status include synonymous coding variants and common polymorphisms (synonymous or non-synonymous). As discussed below, gene status can be assessed by a functional assay, or it may be inferred from the nature of detected deviations from a reference sequence.

In certain embodiments the wild-type or mutant status of the PIK3CA gene is determined by the presence or absence of non-synonymous nucleic acid variations in the genes. Observed non-synonymous variations corresponding to known common polymorphisms with no annotated functional effects do not contribute to a gene status of mutant.

Other variations in the PIK3CA gene that signify mutant status include splice site variations that decrease recognition of an intron/exon junction during processing of pre-mRNA to mRNA. This can result in exon skipping or the inclusion of normally intronic sequence in spliced mRNA (intron retention or utilization of cryptic splice junctions). This can, in turn, result in the production of aberrant protein with insertions and/or deletions relative to the normal protein. Thus, in other embodiments, the gene has a mutant status if there is a variant that alters splice site recognition sequence at an intron/exon junction.

In addition, the measurement of mutation status or activation status of additional genes, such as Kras, a potential marker of resistance in tumours with aberrant or deregulated PIK3CA or PI3K-α, could help increase the predictivity of a Personalised Medicine approach.

In a survey we conducted at AstraZeneca on breast cancers (based on COSMIC database (Welcome Trust Sanger Institute, September 2011), >55 different mutations in the PIK3CA gene were identified from across a dataset covering >5K human tumours. The majority of mutations occurred at <1% frequency, 3 occurred at 1-3% frequency, but 4 mutations accounted for ~88% of total PIK3CA mutations. These were kinase domain missense mutations in the C terminal kinase domain, H1047R (55%) and H1047L (5%), and the helical domain residues, E545K (18%) and E542K (11%). A longer list of other prevalent breast cancer mutations, although not intended to be exhaustive, encompasses R38H, R38C, R88Q, N345K, C420R, E453Q, P539R, E542K, E545K, E545A, Q546K, Q546P, M1043I, M1043V, H1047R, H1047L, H1047Y. Hence diagnostic assays can be built that focus on detection of the most common mutations, thereby allowing identification of the majority of PIK3CA mutations. For example the Cobas™ PIK3CA Mutation Test from Roche Molecular Systems is designed to detect 17 mutations in exons 1, 4, 7, 9 and 20 of the PIK3CA gene (E542K, E545A, E545G, E545K, E545D, Q546K, Q546R, Q546E, Q546L, N345K, C420R, R88Q, H1047L, H1047R, H1047Y, G1049R and M1043I) in DNA isolated from formalin-fixed paraffin-embedded tumour samples. This kit is capable of picking up to ~95% of mutations in ER+ve breast cancer. The distribution of mutations differs across other tumour types and the diagnostic strategy may be adapted accordingly. For example, in endometrial cancer, there is a more even distribution of mutations spread throughout the PIK3CA gene coding sequence and with larger number of mutations in the N terminal region of the protein (communicated by Douglas A. Levine, M. D, TCGA 2nd Annual Symposium, Nov. 28, 2012), compared with breast cancers.

For PIK3CA, reference sequences are available for the gene (GenBank accession number: NG_012113), mRNA (GenBank accession number: NM_006218), and protein (GenBank accession number: NP_006209 or Swiss-Prot accession: P42336). The reference gene (genomic region) sequences include 5000 bases of upstream sequence and 2000 bases of downstream sequence. Mutations within PIK3CA are well known (COSMIC database—Welcome Trust Sanger Institute), and the person of skill in the art will be able to determine the PIK3CA gene status, i.e. whether a particular PIK3CA gene is wild type or mutant, based on comparison of DNA or protein sequence with wild type.

It will be apparent that the gene and mRNA sequences disclosed for PIK3CA and the p110α catalytic subunit of PI3-kinase alpha protein sequence are each a representative sequence. In normal individuals there are two copies of each gene, a maternal and paternal copy, which will likely have some sequence differences, moreover within a population there will exist numerous allelic variants of the gene sequence. Other sequences regarded as wild type include those that possess one or more synonymous changes to the nucleic acid sequence (which changes do not alter the encoded protein sequence), non-synonymous common polymorphisms (e.g. germ-line polymorphisms) which alter the protein sequence but do not affect protein function, and intronic non-splice-site sequence changes.

According to another aspect of the invention there is provided a method for determining the likelihood of effectiveness of treatment with a compound of Formula (I) in a human patient affected with cancer comprising: detecting the presence or absence of at least one non-synonymous nucleic acid variance in the PIK3CA gene of said patient relative to the wild type gene, wherein the presence of at least one somatic non-synonymous nucleic acid variance in the PIK3CA gene indicates that treatment with the compound of Formula (I) is likely to be effective.

According to another aspect of the invention there is provided a method for assessing the susceptibility of an individual to treatment with a compound of Formula (I), which method comprises:
 (i) determining the non-synonymous mutation status of the PIK3CA gene in tumour cell DNA from the individual; and,
 (ii) determining the likely susceptibility of the individual to treatment with a compound of Formula (I) by reference to the non-synonymous mutation status of the PIK3CA gene in the tumour cells.

There are numerous techniques available to the person skilled in the art to determine the gene status of PIK3CA. The gene status can be determined by determination of the nucleic acid sequence. This could be via direct sequencing of the full-length gene or analysis of specific sites within the gene, e.g. commonly mutated sites.

An alternative means for determining whether or not the PIK3CA gene is wild type or mutant is to assess the function of the transcribed gene. Functional mutation of this PIK3CA gene produces a protein that has increased lipid kinase activity resulting in increased downstream signalling of the pathway in cells, including, but not limited to, activation of Akt and S6 kinase. The assays to assess the functional status of PIK3CA variants when expressed in cells include but are not limited to:
(i) increased production of the product of the kinase activity of the PIK3CA gene, phosphatidylinositol-trisphosphate (PI(3,4,5)P3);
(ii) increased levels of phosphorylated Akt or S6 kinase;
(iii) increased focus and colony formation of NIH-3T3 cells transfected with the variant of PIK3CA; (Ikenoue T et al., *Cancer Res.*, 2005 65, 4562-4567).

Samples

The patient's sample to be tested for the gene status can be any tumour tissue or tumour-cell containing sample obtained or obtainable from the individual. The test sample is conveniently a sample of blood, mouth swab, biopsy, or other body fluid or tissue obtained from an individual. Particular examples include: circulating tumour cells, circulating DNA in the plasma or serum, cells isolated from the ascites fluid of ovarian cancer patients, lung sputum for patients with tumours within the lung, a fine needle aspirate from a breast cancer patient, urine, peripheral blood, a cell scraping, a hair follicle, a skin punch or a buccal sample.

It will be appreciated that the test sample may equally be a nucleic acid sequence corresponding to the sequence in the test sample, that is to say that all or a part of the region in the sample nucleic acid may firstly be amplified using any convenient technique e.g. polymerase chain reaction (PCR), before analysis. The nucleic acid may be genomic DNA or fractionated or whole cell RNA. In particular embodiments the RNA is whole cell RNA and is used directly as the template for labelling a first strand cDNA using random primers or poly A primers. The nucleic acid or protein in the test sample may be extracted from the sample according to standard methodologies (see Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.).

The diagnostic methods of the invention can be undertaken using a sample previously taken from the individual or patient. Such samples may be preserved by freezing or fixed and embedded in formalin-paraffin or other media. Alternatively, a fresh tumour cell containing sample may be obtained and used.

The methods of the invention can be applied using cells from any tumour. Suitable tumours for treatment with a compound of Formula (I) have been described hereinbefore.

Mutations in PIK3CA are found broadly in clinical tumours, but the prevalence of mutations in each gene varies significantly by tumour tissue type. For example, PIK3CA mutations are relatively common in breast cancer but relatively rare in kidney tumours.

TABLE 1

Table 1: Prevalence of PIK3CA mutations in clinical samples. Source for PIK3CA information is the COSMIC database (release v62). The patient selection methods of the invention may be particularly useful in the disease (tissue) segments where there is a high incidence of PIK3CA mutations (e.g. breast, urinary tract, endometrium, large intestine, cervix etc.).

| Tissue | PIK3CA mutation prevalence (%) |
| --- | --- |
| Penis | 29 |
| Endometrium | 26 |
| Breast | 26 |
| Small_intestine | 20 |
| Urinary tract | 17 |
| Skin | 13 |
| Large intestine | 12 |
| Stomach | 9 |
| Biliary_tract | 9 |
| Ovary | 9 |
| Cervix | 8 |
| Oesophagus | 6 |
| Liver | 6 |
| Upper aerodigestive tract | 6 |
| CNS | 5 |
| NS | 5 |
| Lung | 4 |
| Thyroid | 4 |
| Pituitary | 3 |
| Soft_tissue | 3 |
| Pancreas | 3 |
| Kidney | 2 |
| Prostate | 2 |
| Meninges | 1 |
| Eye | 1 |
| Autonomic ganglia | 1 |
| Haematopoietic/lymphoid | 1 |
| Adrenal_gland | 0 |
| Bone | 0 |
| Fallopian_tube | 0 |
| Gastrointestinal_tract_(site_indeterminate) | 0 |
| Peritoneum | 0 |
| Salivary_gland | 0 |
| Testis | 0 |
| Thymus | 0 |
| Vagina | 0 |

As will be evident to anyone skilled in the art, this frequency data is continually being refined and updated as new and more comprehensive data emerges from Human Cancer Genome profiling consortia such as the TCGA (The Cancer Genome Atlas) and ICGC (International Cancer Genome Consortium). Hence additional tumour types with PIK3CA dependency may be identified and be eligible for treatment with the compounds described herein.

Methods for Detection of Nucleic Acids

The detection of mutant PIK3CA nucleic acids can be employed, in the context of the present invention, to predict the response to drug treatment. Since mutations in these genes occur at the DNA level, the methods of the invention can be based on detection of mutations or variances in genomic DNA, as well as transcripts and proteins themselves. It can be desirable to confirm mutations in genomic DNA by analysis of transcripts and/or polypeptides, in order to ensure that the detected mutation is indeed expressed in the subject.

It will be apparent to the person skilled in the art that there are a large number of analytical procedures which may be used to detect the presence or absence of variant nucleotides at one or more positions in a gene. In general, the detection of allelic variation requires a mutation discrimination technique, optionally an amplification reaction (such as one based on polymerase chain reaction) and optionally a signal generation system. There are a multitude of mutation detection techniques available in the art and these may be used in combination with a signal generation system, of which there are numerous available in the art. Many methods for the detection of allelic variation are reviewed by Nollau et al., *Clin. Chem.*, 1997, 43, 1114-1120; Anderson S M. *Expert Rev Mol Diagn.*, 2011, 11, 635-642; Meyerson M. et al., *Nat Rev Genet.*, 2010, 11, 685-696; and in standard textbooks, for example "*Laboratory Protocols for Mutation Detection*", Ed. by U. Landegren, Oxford University Press, 1996 and "PCR", $2^{nd}$ Edition by Newton & Graham, BIOS Scientific Publishers Limited, 1997.

As noted above, determining the presence or absence of a particular variance or plurality of variances in the PIK3CA gene in a patient with cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods including, but not limited to, PCR, hybridization with allele-specific probes, enzymatic mutation detection, chemical cleavage of mismatches, mass spectrometry or DNA sequencing, including minisequencing.

Suitable mutation detection techniques include amplification refractory mutation system (ARMS™), amplification refractory mutation system linear extension (ALEX™), competitive oligonucleotide priming system (COPS), Taqman, Molecular Beacons, restriction fragment length polymorphism (RFLP), and restriction site based PCR and fluorescence resonance energy transfer (FRET) techniques.

In particular embodiments the method employed for determining the nucleotide(s) within a biomarker gene is selected from: allele-specific amplification (allele specific PCR)—such as amplification refractory mutation system (ARMS), sequencing, allelic discrimination assay, hybridisation, restriction fragment length polymorphism (RFLP) or oligonucleotide ligation assay (OLA).

In particular embodiments, hybridization with allele specific probes can be conducted by: (1) allele specific oligonucleotides bound to a solid phase (e.g. glass, silicon, nylon membranes) with the labelled sample in solution, for example as in many DNA chip applications; or, (2) bound sample (often cloned DNA or PCR amplified DNA) and labelled oligonucleotides in solution (either allele specific or short so as to allow sequencing by hybridization). Diagnostic tests may involve a panel of variances, often on a solid support, which enables the simultaneous determination of more than one variance. Such hybridization probes are well known in the art (see, e.g., Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) and may span two or more variance sites.

Thus, in one embodiment, the detection of the presence or absence of at least one mutation provides for contacting PIK3CA nucleic acid containing a putative mutation site with at least one nucleic acid probe. The probe preferentially hybridizes with a nucleic acid sequence including a variance site and containing complementary nucleotide bases at the variance site under selective hybridization conditions. Hybridization can be detected with a detectable label using labels known to one skilled in the art. Such labels include, but are not limited to radioactive, fluorescent, dye, and enzymatic labels.

In another embodiment, the detection of the presence or absence of at least one mutation provides for contacting PIK3CA nucleic acid containing a putative mutation site with at least one nucleic acid primer. The primer preferentially hybridizes with a nucleic acid sequence including a variance site and containing complementary nucleotide bases at the variance site under selective hybridization conditions.

Oligonucleotides used as primers for specific amplification may carry the complementary nucleotide base to the mutation of interest in the centre of the molecule (so that amplification depends on differential hybridization; see, e.g., Gibbs, et al., 1989. *Nucl. Acids Res.*, 17, 2437-248) or at the extreme 3'-terminus of one primer where, under appropriate conditions, mismatch can prevent, or reduce polymerase extension (see, e.g., Prossner, 1993, *Tibtech*, 11 238).

In yet another embodiment, the detection of the presence or absence of at least one mutation comprises sequencing at least one nucleic acid sequence and comparing the obtained sequence with the known wild type nucleic acid sequence.

Alternatively, the presence or absence of at least one mutation comprises mass spectrometric determination of at least one nucleic acid sequence.

In one embodiment, the detection of the presence or absence of at least one nucleic acid variance comprises performing a polymerase chain reaction (PCR). The target nucleic acid sequence containing the hypothetical variance is amplified and the nucleotide sequence of the amplified nucleic acid is determined. Determining the nucleotide sequence of the amplified nucleic acid comprises sequencing at least one nucleic acid segment.

Alternatively, amplification products can be analyzed using any method capable of separating the amplification products according to their size, including automated and manual gel electrophoresis, and the like.

Mutations in genomic nucleic acid are advantageously detected by techniques based on mobility shift in amplified nucleic acid fragments. For instance, Chen et al., *Anal Biochem* 1996, 239, 61-9, describe the detection of single-base mutations by a competitive mobility shift assay. Moreover, assays based on the technique of Marcelino et al., *BioTechniques* 1999, 26, 1134-1148 are available commercially.

In a particular example, capillary heteroduplex analysis may be used to detect the presence of mutations based on mobility shift of duplex nucleic acids in capillary systems as a result of the presence of mismatches.

Generation of nucleic acids for analysis from samples generally requires nucleic acid amplification. Many amplification methods rely on an enzymatic chain reaction (such as a polymerase chain reaction, a ligase chain reaction, or a self-sustained sequence replication) or from the replication of all or part of the vector into which it has been cloned.

Preferably, the amplification according to the invention is an exponential amplification, as exhibited by for example the polymerase chain reaction.

Many target and signal amplification methods have been described in the literature, for example, general reviews of these methods in Landegren, U., et al., *Science*, 1988 242, 229-237 and Lewis, R., *Genetic Engineering News* 1990, 10, 54-55. These amplification methods can be used in the methods of our invention, and include polymerase chain reaction (PCR), PCR in situ, ligase amplification reaction (LAR), ligase hybridisation, Qβ bacteriophage replicase, transcription-based amplification system (TAS), genomic amplification with transcript sequencing (GAWTS), nucleic acid sequence-based amplification (NASBA) and in situ hybridisation. Primers suitable for use in various amplification techniques can be prepared according to methods known in the art.

Polymerase Chain Reaction (PCR) PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridised. These oligonucleotides become primers for use with DNA polymerase. The DNA is copied by primer extension to make a second copy of both strands. By repeating the cycle of heat denaturation, primer hybridisation and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours. PCR can be used to amplify any known nucleic acid in a diagnostic context (Mok et al., *Gynaecologic Oncology*, 1994, 52: 247-252,).

An allele specific amplification technique such as Amplification Refractory Mutation System (ARMS™) (Newton et al., *Nucleic Acids Res.*, 1989, 17, 2503-2516) can also be used to detect single base mutations. Under the appropriate PCR amplification conditions a single base mismatch located at the 3'-end of the primer is sufficient for preferential amplification of the perfectly matched allele (Newton et al., 1989, supra), allowing the discrimination of closely related species. The basis of an amplification system using the primers described above is that oligonucleotides with a mismatched 3'-residue will not function as primers in the PCR under appropriate conditions. This amplification system allows genotyping solely by inspection of reaction mixtures after agarose gel electrophoresis.

Analysis of amplification products can be performed using any method capable of separating the amplification products according to their size, including automated and manual gel electrophoresis, mass spectrometry, and the like.

The methods of nucleic acid isolation, amplification and analysis are routine for one skilled in the art and examples of protocols can be found, for example, Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) Particularly useful protocol source for methods used in PCR amplification is *PCR (Basics: From Background to Bench)* by M. J. McPherson, S. G. Mailer, R. Beynon, C. Howe, Springer Verlag; 1st edition (Oct. 15, 2000), ISBN: 0387916008.

The present invention also provides predictive and diagnostic kits comprising degenerate primers to amplify a target nucleic acid in the PIK3CA gene and instructions comprising; amplification protocol and analysis of the results. The kit may alternatively also comprise buffers, enzymes, and containers for performing the amplification and analysis of the amplification products. The kit may also be a component of a screening, or diagnostic kit comprising other tools such as DNA microarrays, or other supports. Preferably, the kit also provides one or more control templates, such as nucleic acids isolated from normal tissue sample, and/or a series of samples representing different variances in the reference genes.

In one embodiment, the kit provides two or more primer pairs, each pair capable of amplifying a different region of the reference (PIK3CA) gene (each region a site of potential variance) thereby providing a kit for analysis of expression of several gene variances in a biological sample in one reaction or several parallel reactions.

Primers in the kits may be labelled, for example fluorescently labelled, to facilitate detection of the amplification products and consequent analysis of the nucleic acid variances. The kit may also allow for more than one variance to be detected in one analysis. A combination kit will therefore comprise of primers capable of amplifying different segments of the reference gene. The primers may be differentially labelled, for example using different fluorescent labels, so as to differentiate between the variances.

Also disclosed are use of 'kits for the detection of PIK3CA mutations, including but not limited to, the PIK3CA mutation detection kits marketed by diagnostic companies including Qiagen and Roche Molecular Systems.

In another aspect, the invention provides a method of treating a patient suffering from cancer comprising: determining the mutant or wild type status of the PIK3CA gene in the patient's tumour cells and if the PIK3CA gene is mutant, administering to the patient an effective amount of a compound of Formula (I).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

According to another aspect of the invention there is provided the use of a compound of Formula (I) to treat a cancer patient whose tumour cells have been identified as possessing a mutant PIK3CA gene.

According to another aspect of the invention there is provided a compound of Formula (I) for treating cancers with tumour cells identified as harbouring mutant PIK3CA gene.

In still further embodiments, the invention relates to pharmaceutical composition comprising a compound of Formula (I) for use in the prevention and treatment of cancer with tumour cells identified as harbouring a mutant PIK3CA gene.

For all the aspects above, mutant forms of PIK3CA determined/identified are at all positions across the gene.

For all the aspects above, using tumours such as breast cancer as an example, particular mutant forms of PIK3CA determined/identified are those at positions R38, R88, N345, C420, E453, P539, E542K, E545K, Q546, M1043, M1043 and H1047R, For all the aspects above, using tumours such as breast cancer as an example, particular mutant forms of PIK3CA determined/identified are those at positions E542, E545 and H1047.

Personalised Healthcare/Personalised Medicine Examples
Cell Proliferation Assay in Tumour Cell Lines The sensitivity of a panel of human cancer cell lines to the effects of compounds was determined in a standard proliferation assay. Assay protocol details are captured under Biological assays (g), above.

Mutation Correlation Analysis
Methods

Pharmacology data measuring cell growth inhibition in response to treatment with Example 3 was obtained for a collection of 209 cancer cell lines from a variety of tissues and from multiple sources. Each cell line was classified as sensitive (GI50<=1.0 µM), or resistant (GI50>1.0 µM).

Mutation status for genes in each cell line was obtained by integrating results from internal (AstraZeneca) and public sources. Public data included all cell line data from the Genomics of Drug Sensitivity in Cancer Project release 3 (Garnett M J, et al. *Nature*, 2012, March 483, 570-5), Cancer Cell Line Encyclopedia project (Barretina J, et al. *Nature* 2012, 483, 603-7) and the Catalogue of Somatic Mutations in Cancer (COSMIC) database (release v61; Forbes S A, et al. *Nucleic Acids Res,* 2011, 39 (Database issue):D945-50; Forbes S A, et al., *Curr Protoc Hum Genet. Acids Res,* 2008; Chapter 10:Unit 10.11.), and selected journal articles. Silent coding region mutations (synonymous variants) and non-synonymous polymorphisms were excluded, and, for the purpose of this analysis, the zygosity of mutations was ignored. For each combination of cell line and gene, status was summarized as mutant (MUT), wild-type (WT) or inconsistent (INCON). Some initially inconsistent cases (independent WT and MUT observations for the same gene in the same cell line) were resolved by weighting internal observations and those for the Cancer Cell line Project (CCLP) subset of COSMIC, or by selecting a status after manual review. In cases where inconsistent observations could not be resolved, the INCON label was retained and the gene status was regarded as unknown during analysis.

Associations between mutation status and response were identified by constructing contingency tables for each gene and determining corresponding odd-ratios and two-tailed Fisher's exact test p-values. The cell lines classified as marginal for response were excluded from the initial analyses to identify candidate biomarkers. For mutation status, MUT or WT findings were counted and Genes with fewer than 4 WT or 4 MUT cell lines were also excluded.

Results and Discussion

Associations between mutation status and response were identified as described in Methods. The cell line response to Example 3 and the corresponding genetic status for the PIK3CA gene is shown in Table 3.

TABLE 3

The pharmacology data, response classification and the mutation status of the PIK3CA gene for the cell lines used in this study.

| Cell Line | Category | Tissue | GI50 µM | PIK3CA |
|---|---|---|---|---|
| RS411 | Sensitive | Blood/lymph | 9.03E−02 | WT |
| T47D | Sensitive | Breast | 0.1982 | MUT |

TABLE 3-continued

The pharmacology data, response classification and the mutation status of the PIK3CA gene for the cell lines used in this study.

| Cell Line | Category | Tissue | GI50 μM | PIK3CA |
|---|---|---|---|---|
| H596 | Sensitive | Lung | 0.3018 | MUT |
| MCF7 | Sensitive | Breast | 0.3094 | MUT |
| MV411 | Sensitive | Blood/lymph | 0.3816 | WT |
| HRA19 | Sensitive | Rectum | 0.3926 | MUT |
| IM95M | Sensitive | Stomach | 0.4359 | MUT |
| MDAMB453 | Sensitive | Breast | 0.4564 | MUT |
| JEKO1 | Sensitive | Blood/lymph | 0.4994 | WT |
| SNU601 | Sensitive | Stomach | 0.5063 | MUT |
| HCC1187 | Sensitive | Breast | 0.5088 | WT |
| SW48 | Sensitive | Colon | 0.5131 | MUT |
| H1703 | Sensitive | Lung | 0.5144 | WT |
| THP1 | Sensitive | Blood/lymph | 0.5281 | WT |
| LK2 | Sensitive | Lung | 0.5884 | WT |
| HUPT4 | Sensitive | Pancreas | 0.6408 | WT |
| L363 | Sensitive | Blood/lymph | 0.6812 | MUT |
| TCCSUP | Sensitive | Bladder | 0.7237 | MUT |
| VMCUB1 | Sensitive | Bladder | 0.7319 | MUT |
| RERFLCSQ1 | Sensitive | Lung | 0.7711 | MUT |
| HCC1419 | Sensitive | Breast | 0.7799 | WT |
| LNCAPCASRES | Sensitive | Prostate | 0.7924 | WT |
| CCK81 | Sensitive | Colon | 0.8031 | MUT |
| HCC1954 | Sensitive | Breast | 0.8794 | MUT |
| SW948 | Sensitive | Colon | 0.9111 | MUT |
| PANC0203 | Sensitive | Pancreas | 0.9628 | WT |
| BFTC905 | Sensitive | Bladder | 0.9662 | WT |
| REH | Resistant | Blood/lymph | 1.047 | WT |
| SNU216 | Resistant | Stomach | 1.072 | WT |
| SKCO1 | Resistant | Colon | 1.128 | WT |
| SUM52PE | Resistant | Breast | 1.145 | WT |
| RT11284 | Resistant | Bladder | 1.171 | WT |
| OVCAR3 | Resistant | Ovary | 1.179 | WT |
| MOLM13 | Resistant | Blood/lymph | 1.22 | WT |
| C99 | Resistant | Colon | 1.224 | WT |
| CALU3 | Resistant | Lung | 1.296 | WT |
| N87 | Resistant | Stomach | 1.301 | WT |
| 2313287 | Resistant | Stomach | 1.339 | WT |
| PAMC82 | Resistant | Stomach | 1.366 | WT |
| HCC1569 | Resistant | Breast | 1.369 | WT |
| AGS | Resistant | Stomach | 1.414 | MUT |
| JIMT1 | Resistant | Breast | 1.46 | MUT |
| HGC27 | Resistant | Stomach | 1.501 | MUT |
| MKN1 | Resistant | Stomach | 1.579 | MUT |
| SKBR3 | Resistant | Breast | 1.588 | WT |
| SNU368 | Resistant | Liver | 1.597 | WT |
| PANC89 | Resistant | Pancreas | 1.618 | WT |
| ASPC1 | Resistant | Pancreas | 1.74 | WT |
| SNU484 | Resistant | Stomach | 1.785 | WT |
| H2085 | Resistant | Lung | 1.835 | WT |
| HARA | Resistant | Lung | 1.906 | WT |
| AZ521 | Resistant | Duodenum | 2.063 | WT |
| HPAC | Resistant | Pancreas | 2.162 | WT |
| NOMO1 | Resistant | Blood/lymph | 2.167 | WT |
| PNT1A | Resistant | Prostate | 2.17 | WT |
| H1975 | Resistant | Lung | 2.262 | MUT |
| OCUM1 | Resistant | Stomach | 2.332 | WT |
| BT20 | Resistant | Breast | 2.36 | MUT |
| HCT8 | Resistant | Colon | 2.51 | MUT |
| COLO320DM | Resistant | Colon | 2.512 | WT |
| PANC1005 | Resistant | Pancreas | 2.607 | WT |
| SW403 | Resistant | Colon | 2.61 | MUT |
| MONOMAC6 | Resistant | Blood/lymph | 2.622 | WT |
| HPAFII | Resistant | Pancreas | 2.63 | WT |
| HT1197 | Resistant | Bladder | 2.8 | MUT |
| LNCAPCLONEFGC | Resistant | Prostate | 3.007 | WT |
| HCC95 | Resistant | Lung | 3.107 | WT |
| SNU620 | Resistant | Stomach | 3.144 | WT |
| MOLP8 | Resistant | Blood/lymph | 3.289 | WT |
| H2291 | Resistant | Lung | 3.291 | WT |
| DMS114 | Resistant | Lung | 3.294 | WT |
| MHCC97L | Resistant | Liver | 3.353 | WT |
| CFPAC1 | Resistant | Pancreas | 3.384 | WT |
| HS766T | Resistant | Pancreas | 3.467 | WT |
| ZR751 | Resistant | Breast | 3.558 | WT |
| PC3 | Resistant | Prostate | 3.833 | WT |
| 22RV1 | Resistant | Prostate | 4.144 | MUT |
| RKO | Resistant | Colon | 4.323 | MUT |
| 977 | Resistant | Bladder | 4.42 | WT |
| MOLM16 | Resistant | Blood/lymph | 4.601 | WT |
| H358 | Resistant | Lung | 4.642 | WT |
| LUDLU1 | Resistant | Lung | 4.646 | WT |
| QGP1 | Resistant | Pancreas | 4.865 | WT |
| OE19 | Resistant | Esophagus | 5.129 | WT |
| SW1710 | Resistant | Bladder | 5.339 | WT |
| PANC1 | Resistant | Pancreas | 5.344 | WT |
| SNU449 | Resistant | Liver | 5.41 | WT |
| 647V | Resistant | Bladder | 5.464 | WT |
| HT29 | Resistant | Colon | 5.483 | MUT |
| SNU354 | Resistant | Liver | 5.604 | WT |
| HS746T | Resistant | Stomach | 5.978 | WT |
| H1869 | Resistant | Lung | 6.044 | WT |
| UMUC3 | Resistant | Bladder | 6.217 | WT |
| PANC0403 | Resistant | Pancreas | 6.468 | WT |
| KG1 | Resistant | Blood/lymph | 6.588 | WT |
| H520 | Resistant | Lung | 6.619 | WT |
| HEP3B | Resistant | Liver | 6.687 | WT |
| HCT15 | Resistant | Colon | 7.268 | MUT |
| H1793 | Resistant | Lung | 7.329 | WT |
| U937 | Resistant | Blood/lymph | 7.345 | WT |
| H2170 | Resistant | Lung | 7.644 | WT |
| PANC0327 | Resistant | Pancreas | 8.025 | WT |
| BEL7405 | Resistant | Liver | 8.11 | WT |
| HT1376 | Resistant | Bladder | 8.199 | WT |
| SNU638 | Resistant | Stomach | 8.221 | WT |
| H322 | Resistant | Lung | 8.227 | WT |
| DU145 | Resistant | Prostate | 8.239 | WT |
| EBC1 | Resistant | Lung | 8.566 | WT |
| JURKAT | Resistant | Blood/lymph | 8.691 | WT |
| COLO205 | Resistant | Colon | 8.934 | WT |
| RT4 | Resistant | Bladder | 8.936 | WT |
| KATOIII | Resistant | Stomach | 9.155 | WT |
| MDAMB468 | Resistant | Breast | 9.325 | WT |
| 5637 | Resistant | Bladder | 9.627 | WT |
| OE33 | Resistant | Esophagus | 9.856 | WT |
| LS180 | Resistant | Colon | 9.942 | MUT |
| HCCC9810 | Resistant | Bile duct | 10.02 | WT |
| H226 | Resistant | Lung | 10.1 | WT |
| A549 | Resistant | Lung | 10.15 | WT |
| QGY7703 | Resistant | Liver | 11.07 | WT |
| H647 | Resistant | Lung | 11.34 | WT |
| MGHU3 | Resistant | Bladder | 11.5 | WT |
| H23 | Resistant | Lung | 12.3 | WT |
| SCABER | Resistant | Bladder | 12.4 | WT |
| H2126 | Resistant | Lung | 12.91 | WT |
| HUPT3 | Resistant | Pancreas | 13.39 | WT |
| SW620 | Resistant | Colon | 13.4 | WT |
| CAPAN2 | Resistant | Pancreas | 13.42 | WT |
| J82 | Resistant | Bladder | 13.42 | MUT |
| HLE | Resistant | Liver | 13.47 | WT |
| BXPC3 | Resistant | Pancreas | 14.08 | WT |
| MCF7MDR+ | Resistant | Breast | 14.45 | WT |
| BEL7404 | Resistant | Liver | 14.9 | WT |
| SNU1 | Resistant | Stomach | 14.97 | WT |
| KP4 | Resistant | Pancreas | 15.05 | WT |
| CAMA1 | Resistant | Breast | 15.47 | WT |
| HCA7 | Resistant | Colon | 15.49 | WT |
| SNU668 | Resistant | Stomach | 15.51 | WT |
| H522 | Resistant | Lung | 15.55 | WT |
| SNU886 | Resistant | Liver | 15.6 | WT |
| SW480 | Resistant | Colon | 15.9 | WT |
| HUH7 | Resistant | Liver | 15.97 | WT |
| CALU1 | Resistant | Lung | 16.03 | WT |
| SNU878 | Resistant | Liver | 16.06 | WT |
| HCC1806 | Resistant | Breast | 16.71 | WT |
| SNU16 | Resistant | Stomach | 16.76 | WT |
| GTL16 | Resistant | Stomach | 17.38 | WT |
| BT549 | Resistant | Breast | 17.44 | WT |
| NAMALWA | Resistant | Blood/lymph | 17.55 | WT |
| WSUDLCL2 | Resistant | Blood/lymph | 17.71 | WT |
| SU8686 | Resistant | Pancreas | 17.97 | WT |
| H460DNP53 | Resistant | Lung | 17.98 | WT |

TABLE 3-continued

The pharmacology data, response classification and the mutation
status of the PIK3CA gene for the cell lines used in this study.

| Cell Line | Category | Tissue | GI50 μM | PIK3CA |
|---|---|---|---|---|
| SNU761 | Resistant | Liver | 18.49 | WT |
| LOVO | Resistant | Colon | 18.64 | WT |
| SW780 | Resistant | Bladder | 19.23 | WT |
| SKMES1 | Resistant | Lung | 19.54 | WT |
| H2286 | Resistant | Lung | 20.03 | WT |
| SNU5 | Resistant | Stomach | 21.19 | WT |
| HCC1395 | Resistant | Breast | 21.81 | WT |
| HUH1 | Resistant | Liver | 22.34 | WT |
| MDAMB231 | Resistant | Breast | 23.61 | WT |
| NUGC3 | Resistant | Stomach | 24.15 | WT |
| MIAPACA2 | Resistant | Pancreas | 24.2 | WT |
| SNU739 | Resistant | Liver | 25.91 | WT |
| CALU6 | Resistant | Lung | 26.15 | WT |
| AMO1 | Resistant | Blood/lymph | 26.93 | WT |
| SW1990 | Resistant | Pancreas | 28.28 | WT |
| CMK | Resistant | Blood/lymph | 28.91 | WT |
| 1A6 | Resistant | Bladder | 30 | WT |
| A2058 | Resistant | Skin | 30 | WT |
| ARH77 | Resistant | Blood/lymph | 30 | WT |
| CAPAN1 | Resistant | Pancreas | 30 | WT |
| CC20 | Resistant | Colon | 30 | WT |
| H1299 | Resistant | Lung | 30 | WT |
| H1437 | Resistant | Lung | 30 | WT |
| H460 | Resistant | Lung | 30 | MUT |
| H526 | Resistant | Lung | 30 | WT |
| H838 | Resistant | Lung | 30 | WT |
| HCC15 | Resistant | Lung | 30 | WT |
| HCC1937 | Resistant | Breast | 30 | WT |
| HCT116 | Resistant | Colon | 30 | MUT |
| HEL9217 | Resistant | Blood/lymph | 30 | INCON |
| HEPG2 | Resistant | Liver | 30 | WT |
| HLF | Resistant | Liver | 30 | WT |
| HX147 | Resistant | Lung | 30 | WT |
| IM9 | Resistant | Blood/lymph | 30 | WT |
| JJN3 | Resistant | Blood/lymph | 30 | WT |
| JVM3 | Resistant | Blood/lymph | 30 | WT |
| K562 | Resistant | Blood/lymph | 30 | WT |
| KU1919 | Resistant | Bladder | 30 | WT |
| MDAMB157 | Resistant | Breast | 30 | WT |
| MDAMB436 | Resistant | Breast | 30 | WT |
| MEC1 | Resistant | Blood/lymph | 30 | WT |
| MKN74 | Resistant | Stomach | 30 | WT |
| NUGC4 | Resistant | Stomach | 30 | WT |
| OCIAML2 | Resistant | Blood/lymph | 30 | WT |
| OCILY19 | Resistant | Blood/lymph | 30 | WT |
| PC9 | Resistant | Lung | 30 | WT |
| RAJI | Resistant | Blood/lymph | 30 | WT |
| RAMOS | Resistant | Blood/lymph | 30 | WT |
| RERFLCAI | Resistant | Lung | 30 | WT |
| RPMI8226 | Resistant | Blood/lymph | 30 | WT |
| SC1 | Resistant | Blood/lymph | 30 | WT |
| SKHEP1 | Resistant | Liver | 30 | WT |
| SMMC7721 | Resistant | Liver | 30 | WT |
| SNU398 | Resistant | Liver | 30 | WT |
| SW900 | Resistant | Lung | 30 | WT |
| T24 | Resistant | Bladder | 30 | WT |
| YAPC | Resistant | Pancreas | 30 | WT |

The gene for which mutations were most strongly correlated with sensitivity to Example 3 was PIK3CA. Only 12 of 177 PIK3CA WT cell lines (7.7%) were sensitive to Example 3, whereas 15 of 32 cell lines (46.9%) that are mutant for PIK3CA were sensitive, corresponding to an odds-ratio of 12.1 and a p-value of $1.2 \times 10^{-7}$ (see Table 4).

TABLE 4

Contingency table for PIK3CA mutation
status and response to Example 3.

| Mutation Status | Response | |
|---|---|---|
| (PIK3CA) | Sensitive | Resistant |
| MUT | 15 | 17 |
| WT | 12 | 165 |

Odds-Ratio: 12.1
p-value: $1.2 \times 10^{-7}$

As indicated herein, it has been reported that the measurement of mutation status or activation status of additional genes, such as KRAS, a potential marker of resistance in tumours with aberrant or deregulated PIK3CA or PI3K-ϵ, could help increase the predictivity of a Personalised Medicine approach.

We exemplified this for the above dataset by comparing the enrichment of KRAS mutations in PIK3CA mutant cells with the cell line's response to inhibition. Analysis was limited to cell lines containing 'hotspot' mutations of the two genes (at codons E542, E545 and H1047 for PIK3CA and at codons K12, 13 and Q61 for KRAS). This demonstrated that in PIK3CA mutant cell lines, mutations in KRAS conferred resistance to inhibition by Example 3.

Twenty-eight cell lines contained activating mutations in PIK3CA.
- 6 of 19 cell lines (31.6%) containing an activating PIK3CA mutation and a wild-type KRAS gene were resistant to Example 3.
- 7 of 9 PIK3CA mutant cell lines (77.8%) contained coexisting KRAS mutations and were resistant to Example 3.

This translates into an odds-ratio of 7.5 and a p-value of 0.042 (see Table 5).

TABLE 5

Contingency table for PIK3CA and KRAS mutation
status and response to Example 3.

| Mutation Status | Response | |
|---|---|---|
| | Sensitive | Resistant |
| KRAS AND PIK3CA MUT | 2 | 7 |
| PIK3CA MUT and KRAS WT | 13 | 6 |

Odds Ratio: 7.5
p-value: 0.042

EXAMPLES

The invention will now be illustrated in the following Examples in which, generally:

(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment in vacuo and work-up procedures were carried out after removal of residual solids by filtration;

(iii) Flash chromatography purifications were performed on an automated Armen Glider Flash: Spot II Ultimate (Armen Instrument, Saint-Ave, France) using prepacked Merck normal phase Si60 silica cartridges (granulometry: 15-40 or 40-63 μm) obtained from Merck, Darmstad, Germany;

(iv) preparative chromatography was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm diameter, 100 mm length, flow rate of 40 mL/minute) using decreasingly polar mixtures of water (containing 0.2% ammonium carbonate) and acetonitrile as eluent;

(v) yields, where present, are not necessarily the maximum attainable;

(vi) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

(vii) in general, end-products of the Formula I were also characterised by mass spectroscopy following liquid chromatography (LCMS); LCMS was carried out using an Waters Alliance HT (2790 & 2795) fitted with a Waters ZQ ESCi or ZMD ESCi mass spectrometer and an X Bridge 5 µm C-18 column (2.1×50 mm) at a flow rate of 2.4 mL/min, using a solvent system of 95% A+5% C to 95% B+5% C over 4 minutes, where A=water, B=methanol, C=1:1 methanol:water (containing 0.2% ammonium carbonate);

(viii) intermediates were not generally fully characterised and purity was assessed by thin layer chromatographic, mass spectral, HPLC and/or NMR analysis;

(ix) X-ray powder diffraction spectra were determined (using a Bruker D4 Analytical Instrument) by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffrac+ software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values;

(x) Differential Scanning Calorimetry was performed using a TA Instruments Q1000 DSC instrument. Typically less than 5 mg of material contained in a standard aluminium pan fitted with a lid was heated over the temperature range 25° C. to 300° C. at a constant heating rate of 10° C. per minute. A purge gas using nitrogen was used at a flow rate of 50 mL per minute; and (xi) the following abbreviations have been used:—
aq. aqueous
$CDCl_3$ deutero-chloroform
$CHCl_3$ chloroform
DBU 1,8-diazabicyclo[5.4.0]undec-7-ene
DCM dichloromethane
DEA diethyl amine
DIPEA N-ethyl-N-isopropylpropan-2-amine
DMA N,N-dimethylacetamide
DMF N,N-dimethylformamide
DMSO dimethyl sulphoxide
DSC Differential Scanning Calorimetry
DTAD (E)-di-tert-butyl diazene-1,2-dicarboxylate
EDCI 1-(3-dimethylaminopropyl)-3-ethylcarbodiimide hydrochloride
Ether diethyl ether
EtOH ethanol
EtOAc ethyl acetate
% ee % enantiomeric excess
HOPO 2-hydroxy-pyridine N-oxide
HPLC high performance liquid chromatography
IPA isopropyl alcohol
MeCN acetonitrile
MeOH methanol
MIBK methyl isobutyl ketone
MTBE methyl tert-butyl ether
NMP 1-methyl-2-pyrrolidone
rt room temperature
sat. saturated
sol. solution
THF tetrahydrofuran
TEA triethyl amine
TBTU 2-(1H-benzo[d][1,2,3]triazol-1-yl)-1,1,3,3-tetramethylisouronium tetrafluoroborate
v/v volume/volume
TFA trifluoroacetic acid Example 1

1-(4-(5-(5-Amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one

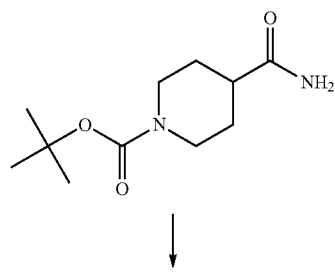

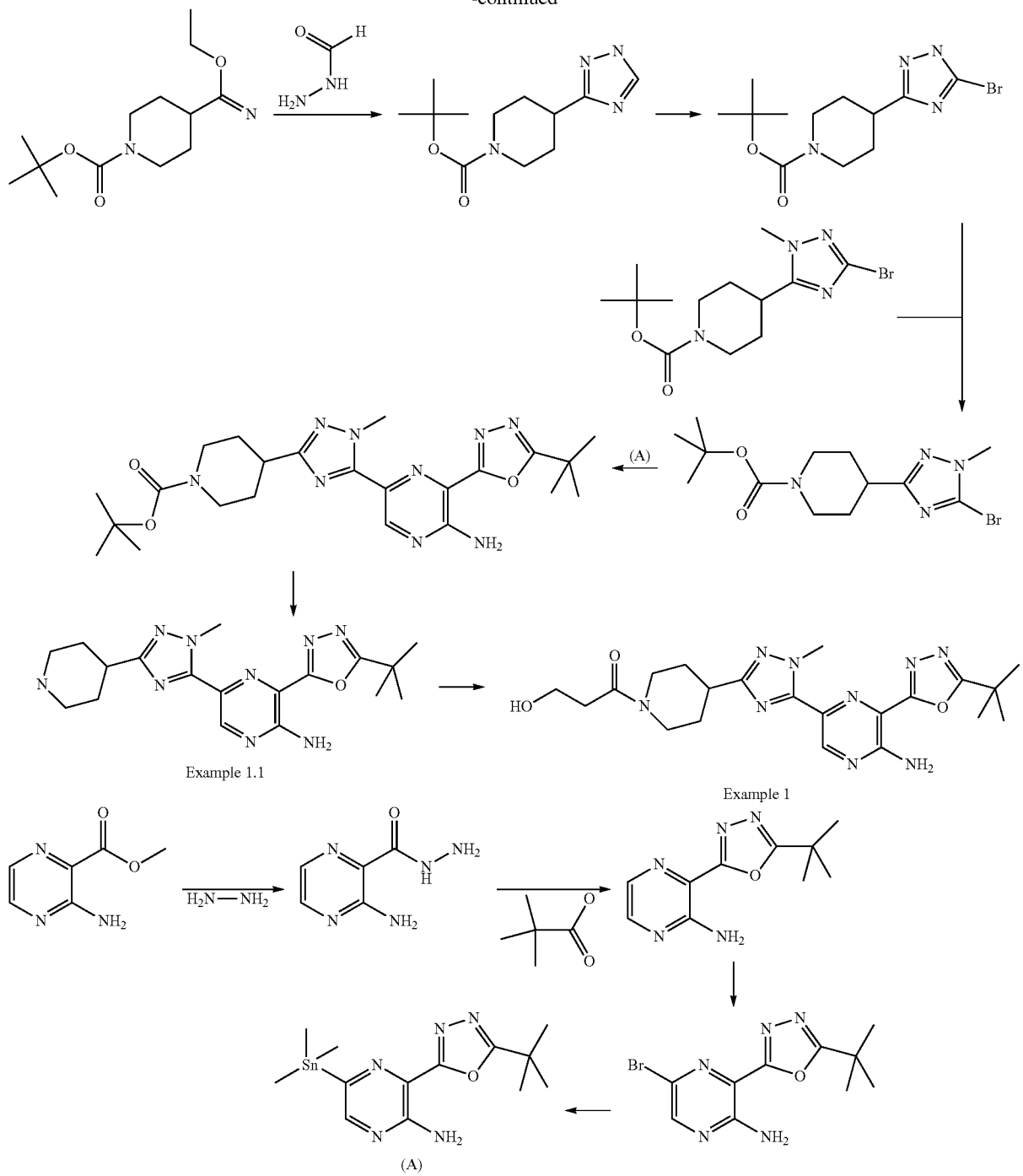

3-Hydroxypropanoic acid (30% v/v soln in water) (200 μL, 47.0 mg, 0.52 mmol) was evaporated to dryness then azeotroped with the toluene. The acid was dissolved in NMP (1 mL) and molecular sieves (100 mg, 0.26 mmol), N-ethyl-N-isopropylpropan-2-amine (0.136 mL, 0.78 mmol) were added followed by the addition of 2-(1H-benzo[d][1,2,3]-triazol-1-yl)-1,1,3,3-tetramethylisouronium tetrafluoroborate (209 mg, 0.65 mmol). After 30 minutes stirring, 3-(5-tert-butyl-1,3,4-oxadiazol-2-yl)-5-(1-methyl-3-(piperidin-4-yl)-1H-1,2,4-triazol-5-yl)pyrazin-2-amine (100 mg, 0.26 mmol) was added and the mixture was stirred for 2 hours.

The reaction mixture was purified by preparative HPLC using a Waters X-Bridge reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent.

The fractions containing the desired compound were evaporated to dryness to afford 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one (45.0 mg, 37.9%) as a clear yellow solid: $^1$H NMR Spectrum (CDCl3) 1.52 (9H, s), 1.79-1.94 (2H, m), 2.07-2.15 (2H, m), 2.58 (2H, t), 2.84-2.94 (1H, m), 3.00-3.10 (1H, m), 3.17-3.26 (1H, m), 3.53 (1H, t), 3.86-3.94 (3H, m), 4.30 (3H, s), 4.56-4.62 (1H, m), 9.02 (1H, s); Mass Spectrum [M+H]$^+$=456.

3-(5-tert-Butyl-1,3,4-oxadiazol-2-yl)-5-(1-methyl-3-(piperidin-4-yl)-1H-1,2,4-triazol-5-yl)pyrazin-2-amine (Example 1.1) was prepared as follows:

At 20° C., tert-butyl 4-carbamoylpiperidine-1-carboxylate (47 g, 205.88 mmol) in dichloromethane (500 mL) was added dropwise to a stirred solution of triethyloxonium hexafluorophosphate(V) (56.2 g, 226.47 mmol) in dichloromethane (500 mL) over a period of 45 minutes under nitrogen. The resulting solution was stirred at 20° C. overnight. A saturated aqueous solution of Na$_2$CO$_3$ was then added until pH of 8 was obtained. The phases were decanted and the aqueous phase was extracted again with 200 mL of CH$_2$Cl$_2$ then the organic phases were dried over MgSO$_4$, filtered and concentrated to afford tert-butyl 4-(ethoxy (imino)methyl)piperidine-1-carboxylate (51.0 g, 97%) as a colourless liquid: $^1$H NMR Spectrum; (CDCl$_3$) 1.28 (3H, t), 1.46 (9H, s), 1.47 (2H, m), 1.79-1.93 (2H, m), 2.28 (1H, m), 2.73 (2H, m), 4.10 (2H, q), 4.13-4.18 (2H, m); Mass Spectrum [M+H]$^+$=no mass ion.

To a stirred solution of tert-butyl 4-(ethoxy(imino) methyl)piperidine-1-carboxylate (51 g, 198.95 mmol) in dioxane (500 mL), was added formohydrazide (17.92 g, 298.43 mmol). This solution was left to stir at 40° C. overnight under N$_2$ resulting in precipitation of a white solid (hydrazide intermediate). The reaction mixture was then heated to 80° C. for 6 h, cooled to room temperature and concentrated. The residue was dissolved in 500 mL of CH$_2$Cl$_2$ and 300 mL of water was added. The phases were decanted and the organic phase was washed with brine, dried over MgSO$_4$, filtered and concentrated to afford tert-butyl 4-(1H-1,2,4-triazol-3-yl)piperidine-1-carboxylate (46.0 g, 92%) as a white solid: $^1$H NMR Spectrum; (CDCl$_3$) 1.47 (9H, s), 1.76 (2H, m), 1.98-2.11 (2H, m), 2.91 (2H, s), 2.97-3.08 (m, 1H), 4.06-4.23 (2H, m), 8.05 (1H, s); Mass Spectrum [M+H]$^+$=no mass ion.

To a stirred solution of tert-butyl 4-(1H-1,2,4-triazol-3-yl)piperidine-1-carboxylate (22 g, 87.19 mmol) in dichloromethane (250 mL) was added sodium hydroxide 2N (131 mL, 261.58 mmol). The reaction mixture was vigorously stirred with mechanical stirring and a solution of benzyltrimethylammonium tribromide (37.4 g, 95.91 mmol) in dichloromethane (250 mL) was then added dropwise, keeping temperature around 15° C. The reaction mixture was left to stir at room temperature for 1 h and 2N HCl was added to give a pH of 5 (keeping temperature around 15° C.). The phases were decanted and the organic phase was washed with H$_2$O (2×1 L), dried over MgSO$_4$, filtered and concentrated to afford tert-butyl 4-(5-bromo-1H-1,2,4-triazol-3-yl) piperidine-1-carboxylate (25.00 g, 87%) as an off-white solid: $^1$H NMR Spectrum; (CDCl$_3$) 1.46 (9H, s), 1.67-1.84 (2H, m), 1.90-2.13 (2H, m), 2.77-2.96 (2H, m), 2.98-3.10 (1H, m), 3.94-4.35 (2H, m); Mass Spectrum [M+H]$^+$=no mass ion.

To a stirred suspension of tert-butyl 4-(5-bromo-1H-1,2, 4-triazol-3-yl)piperidine-1-carboxylate (26 g, 78.50 mmol) in toluene (200 mL) and methanol (50 mL) was added dropwise (diazomethyl)trimethylsilane 2M solution in hexane (43.2 mL, 86.35 mmol) under N$_2$, keeping temperature around 20° C.: gas evolution and a small exotherm were observed. The yellow solution obtained was stirred at room temperature for 1 h. The solvent were evaporated and the resulting oil was purified on silica, eluting with 40% EtOAc in petroleum ether to afford tert-butyl 4-(5-bromo-1-methyl-1H-1,2,4-triazol-3-yl)piperidine-1-carboxylate (15.00 g, 55.3%) as an oil: $^1$H NMR Spectrum; (CDCl$_3$) 1.46 (9H, s), 1.65-1.78 (2H, m), 1.90-2.01 (2H, m), 2.68-3.02 (3H, m), 3.83 (3H, s), 3.94-4.31 (2H, m); Mass Spectrum [M+H]$^+$=no mass ion.

Hydrazine monohydrate (34 mL, 1094.95 mmol) was added portionwise to a stirred suspension of methyl 3-aminopyrazine-2-carboxylate (21.3 g, 139.09 mmol) in ethanol (65 mL) at r.t. The resulting slurry was stirred at 60° C. for 2 hours, cooled to room temperature and filtered. The solid was washed with cold ethanol (2×25 ml) and dried to a constant weight to afford 3-aminopyrazine-2-carbohydrazide (20.75 g, 97%) as a beige solid: $^1$H NMR Spectrum; (DMSO-d$_6$) 4.49 (2H, d), 7.46 (2H, br s), 7.78 (1H, d), 8.17 (1H, d), 9.79 (1H, t); Mass Spectrum [M+H]$^+$=154.

2-(1H-benzo[d][1,2,3]triazol-1-yl)-1,1,3,3-tetramethylisouronium tetrafluoroborate (47.7 g, 148.69 mmol) was added portionwise over 15 minutes to a stirred suspension of N-ethyl-N-isopropylpropan-2-amine (70.6 mL, 405.51 mmol), pivalic acid (17.08 mL, 148.69 mmol) and 3-aminopyrazine-2-carbohydrazide (20.7 g, 135.17 mmol) in acetonitrile (350 mL) and the reaction mixture was stirred at 80° C. for 20 minutes (a solution was obtained). The reaction mixture was cooled to 0° C. and N-ethyl-N-isopropylpropan-2-amine (70.6 mL, 405.51 mmol), followed by 4-methylbenzene-1-sulfonyl chloride (77 g, 405.51 mmol) were added over a period of 15 minutes. The reaction mixture (yellow suspension) was brought to reflux (solubilisation) and then allowed to stir at room temperature for 14 hours affording a dark orange solution. The solution was concentrated. The residue was diluted with dichloromethane, washed with water, brine, dried over magnesium sulfate and concentrated. The crude product was purified by flash chromatography on silica gel eluting with 0 to 40% ethyl acetate in dichloromethane. The solvent was evaporated to dryness. The resulting mixture was triturated with ether (100 mL), filtered, washed with the minimum of ether and dried to afford 3-(5-tert-butyl-1,3,4-oxadiazol-2-yl)pyrazin-2-amine (20.8 g, 70.2%) as a pale yellow solid: $^1$H NMR Spectrum; (CDCl$_3$) 1.53 (9H, s), 1.58-1.68 (2H, m), 6.67 (2H, s), 8.13 (2H, dt); Mass Spectrum [M+H]$^+$=220.

1-Bromopyrrolidine-2,5-dione (18.57 g, 104.36 mmol) was added portionwise to a solution of 3-(5-tert-butyl-1,3, 4-oxadiazol-2-yl)pyrazin-2-amine (20.8 g, 94.87 mmol) in THF (320 mL) and the solution was stirred at room temperature for 16 hours. The reaction mixture was concentrated and the residue was dissolved in dichloromethane (300 mL), washed with water (2×150 mL), brine, dried over magnesium sulfate and concentrated. The solvent was evaporated and the crude product was purified by flash chromatography on silica gel, eluting with 0 to 10% ethyl acetate in dichloromethane. The solvent was evaporated to dryness to afford 5-bromo-3-(5-tert-butyl-1,3,4-oxadiazol-2-yl)pyrazin-2-amine (25.5 g, 90%) as a beige solid: $^1$H NMR Spectrum; (CDCl$_3$) 1.52 (9H, s), 8.23 (1H, s); Mass Spectrum [M+H]$^+$=300.

To a suspension of 5-bromo-3-(5-tert-butyl-1,3,4-oxadiazol-2-yl)pyrazin-2-amine (45 g, 150.94 mmol) in toluene (450 mL) were added 1,1,1,2,2,2-hexamethyldistannane (37.6 mL, 181.12 mmol) and bis(triphenylphosphine)palladium (II) chloride (5.30 g, 7.55 mmol). The reaction mixture was degassed with argon and heated at 80° C. for 2 hours. (solubilisation upon heating, orange solution then reprecipitation and turned black indicating reaction is complete.) The reaction mixture was cooled down, concentrated and the residue was dissolved in CH$_2$Cl$_2$ and filtered on Decalite to remove the insoluble impurities. The filtrate was concentrated and purified on silica eluting with 0 to 10% EtOAc in CH$_2$Cl$_2$. The solvent was concentrated to afford 3-(5-tert-butyl-1,3,4-oxadiazol-2-yl)-5-(trimethylstannyl)pyrazin-2-amine (22.63 g, 39.2%) as an orange solid: $^1$H NMR Spectrum; (CDCl$_3$) 0.38 (9H, s), 1.53 (9H, s), 6.49 (2H, br s), 8.13 (1H, s); Mass Spectrum [M+H]$^+$=384.

To a stirred suspension of tert-butyl 4-(5-bromo-1-methyl-1H-1,2,4-triazol-3-yl)piperidine-1-carboxylate (2700 mg, 7.82 mmol) and 3-(5-tert-butyl-1,3,4-oxadiazol-2-yl)-5-(trimethylstannyl)pyrazin-2-amine (2988 mg, 7.82 mmol) in 4-methyl-2-pentanol (28 mL) were added lithium chloride (995 mg, 23.46 mmol) and bis(triphenylphosphine) palladium (II) chloride (220 mg, 0.31 mmol). The mixture was degassed with argon and heated at 140° C. for 2 h. The reaction was cooled down and the resulting precipitate was collected by filtration, washed with isopropanol (25 mL), water (25 mL) and dried under suction. The isopropanol organic fraction was concentrated and the precipitate formed was collected and combined with the main precipitate affording tert-butyl 4-(5-(5-amino-6-(5-tert-butyl-1,3,4-oxadiazol-2-yl)pyrazin-2-yl)-1-methyl-1H-1,2,4-triazol-3-yl)piperidine-1-carboxylate (3.0 g, 79%): $^1$H NMR Spectrum: (DMSO-$d_6$) 1.41 (9H, s), 1.45 (9H, s), 1.50-1.68 (2H, m), 1.95 (3H, dd), 2.78-3.05 (1H, m), 3.96 (3H, d), 4.21 (3H, s), 8.86 (1H, s); Mass Spectrum [M+H]$^+$=484.

A solution of tert-butyl 4-(5-(5-amino-6-(5-tert-butyl-1,3,4-oxadiazol-2-yl)pyrazin-2-yl)-1-methyl-1H-1,2,4-triazol-3-yl)piperidine-1-carboxylate (3 g, 6.20 mmol) in TFA (15 mL) and $CH_2Cl_2$ (15 mL) was stirred at 25° C. for 1 hour. The mixture was azeotroped with toluene, a 7N solution of ammonia in methanol and dichloromethane were added and the mixture was adsorbed on silica gel. The crude product was purified by flash chromatography on silica gel eluting with 0 to 8% methanol in dichloromethane followed by 0 to 10% methanolic ammonia in dichloromethane The solvent was evaporated to dryness to afford 3-(5-tert-butyl-1,3,4-oxadiazol-2-yl)-5-(1-methyl-3-(piperidin-4-yl)-1H-1,2,4-triazol-5-yl)pyrazin-2-amine (2.040 g, 86%) as a yellow crystalline solid: $^1$H NMR Spectrum: (DMSO-$d_6$) 1.45 (9H, s), 1.55-1.66 (2H, m), 1.86 (2H, dd), 2.52-2.61 (2H, m), 2.69-2.78 (1H, m), 2.95-3.02 (2H, m), 4.20 (3H, s), 8.86 (1H, s); Mass Spectrum [M+H]$^+$=384.

Isolation of Single Crystalline Form of Example 1

The X-ray powder diffraction spectra of the material isolated above showed the material to be crystalline but a mixture of polymorphic forms. This material had a melting point of 226.4° C. (onset).

Form A material was produced by slurrying the original material in acetonitrile at 25° C. Approximately 20 mg of the original material was placed in a vial with a magnetic stirrer bar, and approximately 2 mL of acetonitrile added, the vial was then sealed tightly with a cap and left to stir on a magnetic stirrer plate. After approximately 5 days, the sample was removed from the plate, the cap taken off and the slurry left to dry under ambient conditions before it was analysed by XRPD and DSC. This form (Form A) was determined to be crystalline by XRPD. This material had a melting point of 227.2° C. (onset).

The same crystalline form may be made by stirring the crude material in acetonitrile overnight at room temperature, then filtering the resulting solid, washing with cold acetonitrile and drying.

In one aspect of the invention there is provided a process for forming a crystalline form of Example 1 (Form A) by slurrying a sample of the compound in acetonitrile. Ten X-Ray powder diffraction peaks are shown in the Table below:

| Ten X-Ray Powder Diffraction peaks for Example 1 Form A | |
|---|---|
| Angle 2-Theta (2θ) | Intensity % |
| 5.1 | 100.0 |
| 18.0 | 22.5 |
| 10.2 | 22.0 |
| 11.7 | 17.8 |
| 19.4 | 14.5 |
| 18.5 | 14.2 |
| 14.8 | 12.6 |
| 26.7 | 11.0 |
| 26.6 | 10.6 |
| 17.8 | 9.9 |

An X-Ray powder diffraction spectrum of Example 1 Form A is shown in FIG. 1.

DSC analysis of Example 1 Form A shows a melting endotherm with an onset of 227.2° C. and a peak at 228.6° C. (FIG. 2).

Thus DSC analysis shows Example 1 Form A is a high melting solid with an onset of melting at about 227.2° C. and a peak at 228.6° C.

A DSC of Example 1 Form A is shown in FIG. 2.

X-Ray Powder Diffraction

Analytical Instrument: Bruker D4.

The X-ray powder diffractogram was determined by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffrac+ software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry

Analytical Instrument: TA Instruments Q1000 DSC.

Typically less than 5 mg of material contained in a standard aluminium pan fitted with a lid was heated over the temperature range 25° C. to 300° C. at a constant heating rate of 10° C. per minute. A purge gas using nitrogen was used—flow rate 50 ml per minute.

An alternative synthesis of the compound of Example 1 is provided below as Example 2.

Example 2

1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one

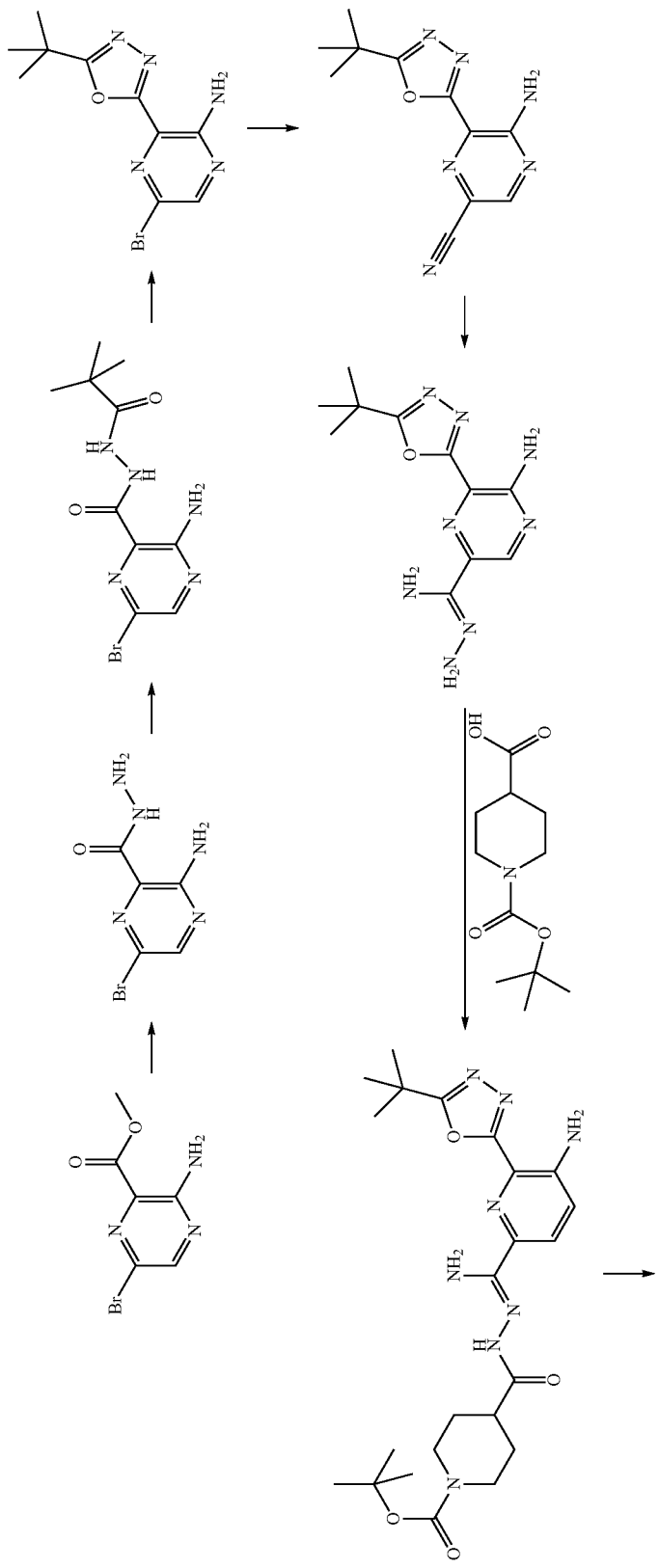

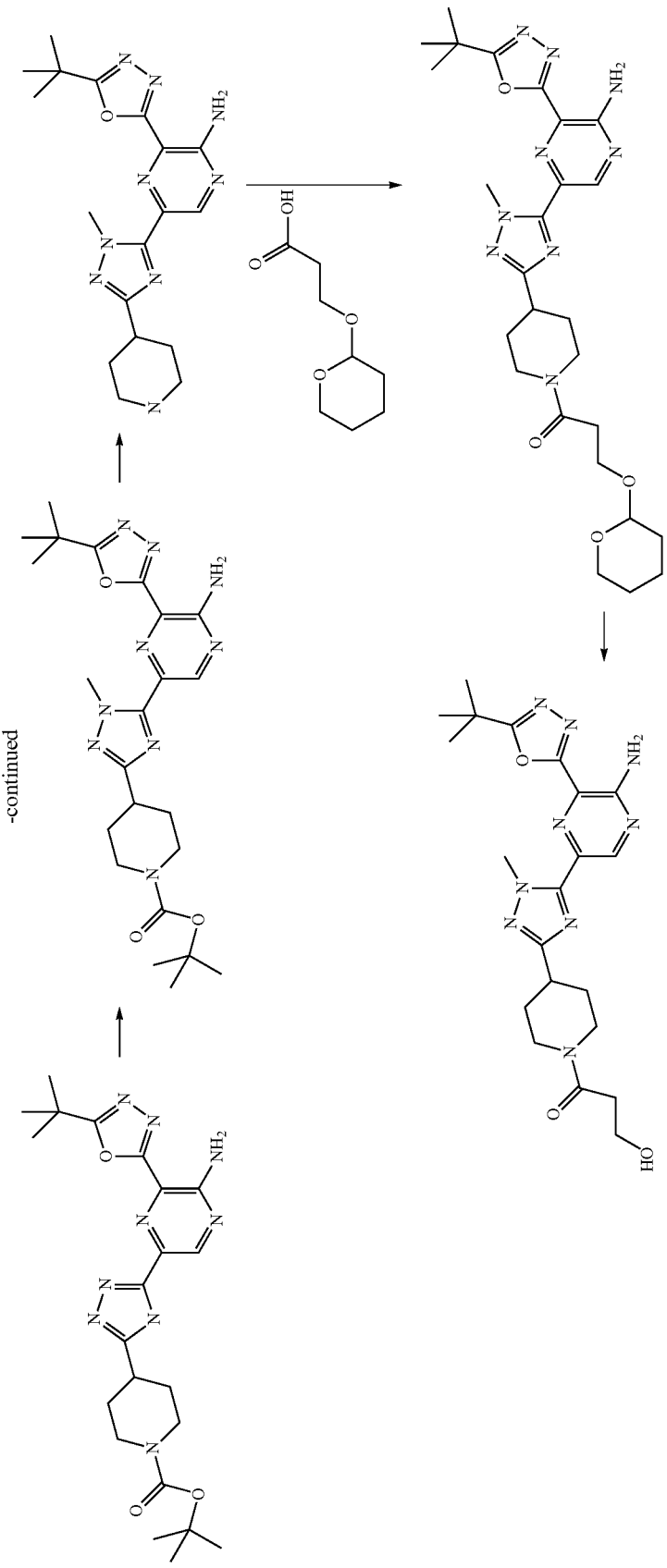

Pyridine 4-methylbenzenesulfonate (3.58 g, 14.25 mmol) was added to a suspension of 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-(tetrahydro-2H-pyran-2-yloxy)propan-1-one (37 g, 68.57 mmol) in methanol (275 mL) under nitrogen. The mixture was stirred at 60° C. for 1.5 hours. The mixture was soluble after 5 minutes. The mixture was held at 50° C. overnight during which time a precipitate formed. The reaction mixture was dissolved in dichloromethane (400 mL), washed with water (300 mL), and brine (100 mL). The aqueous extracts were backwashed with DCM (100 mL) and the combined organic layers were dried over MgSO$_4$ and concentrated. The crude product was purified by flash chromatography on silica gel eluting with 100% ethyl acetate to 10:50:40 methanol/ethyl acetate/DCM. The product containing fractions were evaporated to dryness to afford a beige solid (24.5 g). The solid was slurried overnight in acetonitrile (500 mL), filtered and dried under high vacuum to afford 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-hydroxypropan-1-one (Example 2) (24 g, 78%) as a cream solid: $^1$H NMR Spectrum: (DMSO-d$_6$) 1.51 (9H, s), 1.55-1.68 (1H, m), 1.68-1.84 (1H, m), 1.96-2.13 (2H, m), 2.78-2.93 (1H, m), 2.98-3.1 (1H, m), 3.19-3.3 (1H, m), 3.71 (2H, q), 3.93-4.04 (1H, m), 4.27 (3H, s), 4.35-4.48 (1H, m), 4.54 (1H, t), 7.96 (2H, s), 8.92 (1H, s); Mass Spectrum [M+H]$^+$=456

(4-(5-(5-Amino-6-(5-tert-butyl-1,3,4-oxadiazol-2-yl)pyrazin-2-yl)-1-methyl-1H-1,2,4-triazol-3-yl)piperidin-1-yl)-3-(tetrahydro-2H-pyran-2-yloxy)propan-1-one (Example 2.1) was prepared as follows:

Hydrazine hydrate (23.59 mL, 480.75 mmol) was added dropwise to a stirred mixture of methyl 3-amino-6-bromopyrazine-2-carboxylate (100 g, 418.04 mmol) in EtOH (2 L). The mixture was heated at 50° C. under nitrogen. The resulting thick suspension was stirred at 50° C. for 16 hours. Further hydrazine (2.5 mL) was added in one portion and the suspension was stirred at 50° C. for a further 24 hours. Ethanol (500 mL) was charged to the thick reaction mixture and the mixture was allowed to cool to room temperature. The resulting suspension was filtered and the solid washed with ethanol (1 L) and dried in vacuo to give 3-amino-6-bromopyrazine-2-carbohydrazide (98 g, quantitative) as a cream solid: $^1$H NMR Spectrum; (DMSO-d$_6$) 4.52 (2H, s), 7.59 (2H, s), 8.30 (1H, s), 9.74 (1H, s); Mass Spectrum [M+H]$^+$=232.

Pivalic anhydride (165 mL, 815.38 mmol) was added to a stirred mixture of 3-amino-6-bromopyrazine-2-carbohydrazide (172 g, 741.26 mmol) in acetonitrile (1.8 L) and the mixture was heated at 80° C. for 1 hour. The reaction was left to stir for 16 hours. The required yellow solid material was isolated by filtration. The filtrate was partitioned between EtOAc (2 L) and aqueous sodium bicarbonate (2 L). The organic layer was washed with saturated brine and dried over MgSO$_4$. The solution was filtered and concentrated to give an orange sticky solid which was triturated with MTBE (250 mL). The insoluble yellow solid was isolated by filtration and this material was shown to be identical to the first solid. The combined solids were dried in the vacuum oven at 50° C. for 3 days to afford 3-amino-6-bromo-N'-pivaloylpyrazine-2-carbohydrazide (224 g, 96%) as a yellow solid: $^1$H NMR Spectrum: (DMSO-d$_6$) 1.17 (9H, s), 7.62 (2H, s), 8.37 (1H, s), 9.42-9.56 (1H, m), 10.09-10.23 (1H, m); Mass Spectrum [M+H]$^+$=318.

p-Toluenesulfonyl chloride (164 g, 861.60 mmol) was added portion wise to a suspension of 3-amino-6-bromo-N'-pivaloylpyrazine-2-carbohydrazide (227 g, 718.00 mmol) and N,N-diisopropylethylamine (297 mL, 1795.01 mmol) in acetonitrile (2200 mL). The mixture was stirred for 2 hours at 70° C. The reaction was left to cool to room temperature overnight. The reaction mixture was partitioned between ethyl acetate (2 L) and sodium bicarbonate solution (2 L). The organic layer was washed with saturated brine, dried with magnesium sulfate, filtered, and concentrated under reduced pressure. The resulting brown/beige solid was triturated with hot MTBE (1000 mL) and isolated by filtration and dried to afford 5-bromo-3-(5-tert-butyl-1,3,4-oxadiazol-2-yl)pyrazin-2-amine as a yellow solid (187 g, 87%). The mother liquors were evaporated to dryness. The crude solid was triturated with MTBE (500 mL) filtered and washed with 100 mL of MTBE. The resulting solid was air dried overnight to afford a second crop of 5-bromo-3-(5-tert-butyl-1,3,4-oxadiazol-2-yl)pyrazin-2-amine (36 g, 17%): $^1$H NMR Spectrum: (DMSO-d$_6$) 1.43 (9H, s), 7.70 (2H, s), 8.39 (1H, s); Mass Spectrum [M+H]$^+$=298.

In an alternative preparation, to 3-amino-6-bromo-N'-pivaloylpyrazine-2-carbohydrazide (2301 g, 7.28 mol) in MeCN (10.8 L) was added DIPEA (3.044 L, 17.48 mol) and p-toluenesulfonyl chloride (1665 g, 8.73 mol) portion-wise (~280 g×6) at 50° C. over a period of 30 mins. The reaction temperature was maintained between 65-70° C. by controlling the rate of addition. After the addition was complete, the reaction mixture was stirred at 70° C. for 1 h. The mixture was cooled to room temperature and quenched with 5% NaHCO$_3$ (aqueous, 24.2 L). The resulting suspension was stirred for 30 min then filtered. The product was washed with water (14.8 L), pulled dry and dried at 50° C. for 16 h. The product was dissolved in DCM (12 L) and the phases separated. The organic phase was loaded onto a silica pad (6 kg) and the product was eluted with 20% EtOAc/DCM (8×10 L). Concentration of the product containing fractions gave 1987 g (92% yield) with a purity of 99.8% by HPLC.

A stream of nitrogen gas was passed through a solution of 5-bromo-3-(5-tert-butyl-1,3,4-oxadiazol-2-yl)pyrazin-2-amine (89.35 g, 239.75 mmol) in DMA (1.2 L) for 20 minutes. Dicyclohexyl(2',4',6'-triisopropylbiphenyl-2-yl)phosphine (11.43 g, 23.98 mmol), tris(dibenzylideneacetone)dipalladium(0) (5.49 g, 5.99 mmol), zinc (1.568 g, 23.98 mmol) and dicyanozinc (16.89 g, 143.85 mmol) were added sequentially to the stirred mixture. The mixture was heated to 100° C. and stirred for 1 hour. The mixture was cooled and partitioned between DCM (3 L) and water (1 L). The black mixture was filtered through celite and the organic layer was separated. The solution was washed with water then brine. The solution was dried with magnesium sulfate and concentrated under reduced pressure. The residue was triturated with MTBE and isolated by filtration, washing with MTBE. The filter cake was dried in vacuo to afford 5-amino-6-(5-tert-butyl-1,3,4-oxadiazol-2-yl)pyrazine-2-carbonitrile (55.7 g, 95%) as a pale orange solid: $^1$H NMR Spectrum: (DMSO-d$_6$) 1.46 (9H, s), 6.02 (1H, s), 8.38 (2H, s); Mass Spectrum [M−H]$^−$=242.

The product may be slurried in heptanes then filtered and dried as an alternative to trituration with MTBE.

Hydrazine hydrate (82 mL, 1.69 mol) was added to 5-amino-6-(5-tert-butyl-1,3,4-oxadiazol-2-yl)pyrazine-2-carbonitrile (55 g, 225.18 mmol) in IPA (200 mL) and the mixture was heated at 50° C. under nitrogen for 16 hours. The mixture was cooled in an ice bath. The resulting precipitate was collected by filtration, washed with IPA and diethyl ether and dried to a constant weight to afford (Z)-5-amino-6-(5-tert-butyl-1,3,4-oxadiazol-2-yl)pyrazine-2-carbohydrazonamide (49.2 g, 79%) as a yellow solid: $^1$H NMR Spectrum: (DMSO-d$_6$) 1.45 (9H, s), 5.26 (2H, s), 5.58 (2H, s), 7.56 (2H, s), 8.75 (1H, s); Mass Spectrum [M+H]$^+$=277.

O-(7-Azabenzotriazol-1-yl)-N,N,N',N'-tetramethyluronium hexafluorophosphate (74.3 g, 195.44 mmol) was added to a solution of N-Boc-isonipecotic acid (41.1 g, 179.15 mmol) and 4-methylmorpholine (35.9 mL, 325.74 mmol) in DMA (800 mL). The mixture was stirred for 10 minutes then (Z)-5-amino-6-(5-tert-butyl-1,3,4-oxadiazol-2-yl)pyrazine-2-carbohydrazonamide (45 g, 162.87 mmol) was added to the solution in one portion (exotherm observed from 22° C. to 27° C.). After a few minutes the product crystallised from the reaction mixture. The reaction mixture was removed from the vessel and filtered through a sinter. Additional DMA was added to wash product from the sides of the vessel (150 mL) and this was poured onto the filter cake. Isopropanol (600 mL) was added to the vessel and the remainder of the product in the vessel was suspended in this solvent using vigorous agitation. The isopropanol suspension was used to wash the filter cake once the DMA had been removed by suction. The filter cake was sucked dry then washed with MTBE and sucked dry once again. The filter cake was dried in vacuo to afford (Z)-tert-butyl 4-(2-(amino (5-amino-6-(5-tert-butyl-1,3,4-oxadiazol-2-yl)pyrazin-2-yl) methylene)hydrazinecarbonyl)piperidine-1-carboxylate (76 g, 95%) as a yellow solid: $^1$H NMR Spectrum: (DMSO-d$_6$) 1.40 (9H, s), 1.46 (9H, s), 1.63-1.9 (2H, m), 2.33-2.6 (2H, m, obscured by DMSO signal), 2.63-3.03 (2H, m), 3.18-3.48 (4H, m, obscured by water signal), 3.88-4.11 (2H, m), 6.43 (2H, s), 7.76 (2H, br), 8.84 (0.5H, s), 8.87 (0.5H, s), 9.85 (1H, s); Mass Spectrum [M+H]$^+$=488

In an alternative preparation, the N-Boc-isonipecotic acid may be made in situ as follows: Isonipecotic acid (858 g, 3.74 mol) was dissolved in DMA (25.3 L) and 4-methylmorpholine (393 mL, 3.74 mol) added. Stirred for 5 mins and isobutyl chloroformate (489 mL, 3.74 mol) added. The reaction mixture was stirred at 25° C. for 2 h and cooled to 15° C. before (Z)-5-amino-6-(5-tert-butyl-1,3,4-oxadiazol-2-yl)pyrazine-2-carbohydrazonamide (940 g, 3.4 mol) was added portionwise over 10 mins. The reaction mixture was stirred for 1-2 h at 15° C. Water (20.5 L) was added portionwise over 1 h and stirred for a further 1 h before being filtered. The filtercake was then washed with water (4×4 L) and pulled dry on the filter before being dried in a vacuum oven at 50° C. until dry to give the desired product.

Acetic acid (200 mL) was added to dioxane (500 mL) in a 3 L fixed double jacketed vessel and the solution was heated to 70° C. under nitrogen. (Z)-tert-butyl 4-(2-(amino (5-amino-6-(5-tert-butyl-1,3,4-oxadiazol-2-yl)pyrazin-2-yl) methylene)hydrazinecarbonyl)-piperidine-1-carboxylate (74.5 g, 152.80 mmol) was added portionwise to the warm mixture. After 10 minutes the temperature was increased to 100° C. (slight reflux). The reaction mixture was stirred at 100° C. for 1.5 hours (suspension) then held at 80° C. overnight (solution formed after overnight hold). The resulting solution was concentrated under reduced pressure, then diluted with toluene, evaporated to dryness, taken up with toluene and concentrated again. The residual oil was mixed with some ethyl acetate and concentrated to dryness. A solid crystallised from solution which was triturated with MTBE (200 mL) and isolated by filtration. The filter cake was washed with water and MTBE to afford tert-butyl 4-(5-(5-amino-6-(5-tert-butyl-1,3,4-oxadiazol-2-yl)pyrazin-2-yl)-1H-1,2,4-triazol-3-yl)piperidine-1-carboxylate (50 g, 70%) as a grey solid.

The filtrate was concentrated under reduced pressure to give a yellow solid. This material was triturated with MTBE and filtered. The filter cake was washed with ethyl acetate and then MTBE to give a second crop as a pale yellow solid (4.93 g, 7%). This material was identical to the first crop: $^1$H NMR Spectrum: (DMSO-d$_6$) 1.17 (9H, s), 1.22 (9H, s), 1.29-1.47 (2H, m), 1.67-1.78 (2H, m), 2.57-2.87 (3H, m), 3.57-3.92 (2H, m), 7.56 (2H, br), 8.56 (1H, s), 13.47 (2H, br s); Mass Spectrum [M+H]+=470.

1,8-Diazabicyclo[5.4.0]undec-7-ene (19.87 mL, 132.90 mmol) was added to a suspension of tert-butyl 4-(5-(5-amino-6-(5-tert-butyl-1,3,4-oxadiazol-2-yl)pyrazin-2-yl)-1H-1,2,4-triazol-3-yl)piperidine-1-carboxylate (48 g, 102.23 mmol) in 2-methylTHF (300 mL). A dark solution was obtained after 5 minutes which was treated with charcoal and filtered through a celite pad, washing the charcoal and charcoal with additional 2-methylTHF (100 mL). The filtrate was stirred with an air stirrer at −5° C. in a 3 L jacketed fixed vessel under an atmosphere of nitrogen. 2-methylTHF (100 mL) was added to help stir the yellow suspension. Iodomethane (7.96 mL, 127.78 mmol) was added dropwise over 15 minutes. The mixture was stirred for 2 hours and the reaction mixture was warmed to room temperature. After 16 hours, additional iodomethane (6 mL) and DBU (20 mL) was added and stirring was continued for 16 hours. The mixture was poured into water and stirred for 5 minutes. The insoluble material was isolated as a beige solid and dried in vacuo to afford tert-butyl 4-(5-(5-amino-6-(5-tert-butyl-1,3,4-oxadiazol-2-yl)pyrazin-2-yl)-1-methyl-1H-1,2,4-triazol-3-yl)piperidine-1-carboxylate (24.77 g, 50.1%). The mother liquors were concentrated under reduced pressure and the residue was purified by flash column chromatography on silica using MTBE as the eluant. A second crop of the desired product (13.04 g, 26%), was thus obtained as a yellow solid: $^1$H NMR Spectrum: (DMSO-d$_6$) 1.47 (9H, s), 1.51 (9H, s), 1.57-1.76 (2H, m), 1.94-2.1 (2H, m), 2.87-3.09 (3H, m), 3.9-4.08 (2H, m), 4.26 (3H, s), 7.97 (2H, br, s), 8.92 (1H, s); Mass Spectrum [M+H]$^+$=484 tert-Butyl 4-(5-(5-amino-6-(5-tert-butyl-1,3,4-oxadiazol-2-yl)pyrazin-2-yl)-1-methyl-1H-1,2,4-triazol-3-yl)piperidine-1-carboxylate (36.81 g, 76.12 mmol) was added to a solution of 2,2,2-trifluoroacetic acid (100 mL, 1305.87 mmol) in DCM (100 mL). The mixture was stirred for 3 hours at room temperature. The mixture was concentrated under reduced pressure. The residue was dissolved in DCM (1.5 L) and added to vigorously stirred concentrated ammonia (150 mL) in water (400 mL). The aqueous was washed with DCM (400 mL) and the combined organic solutions were dried with magnesium sulfate, filtered and concentrated to dryness to afford 3-(5-tert-butyl-1,3,4-oxadiazol-2-yl)-5-(1-methyl-3-(piperidin-4-yl)-1H-1,2,4-triazol-5-yl) pyrazin-2-amine (30.0 g, 103%) as a yellow solid:

$^1$H NMR Spectrum: (DMSO-d$_6$) 1.44 (9H, s), 1.54-1.69 (2H, m), 1.8-1.92 (2H, m), 2.53-2.63 (2H, m), 2.68-2.83 (1H, m), 2.93-3.05 (2H, m), 4.19 (3H, s), 7.89 (2H, br), 8.85 (1H, s); Mass Spectrum [M+H]$^+$=384.

O-(7-Azabenzotriazol-1-yl)-N,N,N',N'-tetramethyluronium hexafluorophosphate (30.4 g, 80.04 mmol), was added portionwise to a stirred solution of 3-(tetrahydro-2H-pyran-2-yloxy)propanoic acid (12.67 g, 72.76 mmol) and N-ethyl-N-isopropylpropan-2-amine (25.3 mL, 145.52 mmol) dissolved in acetonitrile (200 mL) at 25° C. The resulting solution was stirred at 25° C. for 20 minutes then 3-(5-tert-butyl-1,3,4-oxadiazol-2-yl)-5-(1-methyl-3-(piperidin-4-yl)-1H-1,2,4-triazol-5-yl)pyrazin-2-amine (30 g, 72.76 mmol) was added portionwise, washing the last portion into the mixture as a slurry in acetonitrile (100 mL). After stirring for 1 hour the precipitate was collected by filtration, washed with acetonitrile and drying in vacuo to afford 1-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-(tetrahydro-2H-pyran-2-yloxy)propan-1-one (35.0 g, 89%) as a beige solid. The filtrate was diluted with DCM (600 mL), washed with water, dried over magnesium sulfate and concentrated. The residue was purified by flash chromatography on silica gel eluting with a gradient of 2 to 2.5% 7N ammonia in methanol with dichloromethane. A second crop of product (3.31 g, 6.13 mmol, 8.43%) was also obtained as a cream solid. Both samples were combined to give a beige solid: $^1$H NMR Spectrum: (DMSO-d$_6$) 1.44 (9H, s), 1.52-1.79 (4H, m), 1.88-2.04 (2H, m), 2.53-2.73 (2H, m), 2.73-2.87 (1H, m), 2.91-3.05 (1H, m), 3.13-3.24 (1H, m), 3.37-3.47 (1H, m), 3.53-3.65 (1H, m), 3.7-3.8 (1H, m), 3.81-3.89 (1H, m), 3.89-3.99 (1H, m), 4.20 (3H, s), 4.29-4.4 (1H, m), 4.54-4.61 (1H, m), 7.60-8.20 (2H, br), 8.85 (1H, s); Mass Spectrum [M+H]$^+$=540.

Example 3

1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one

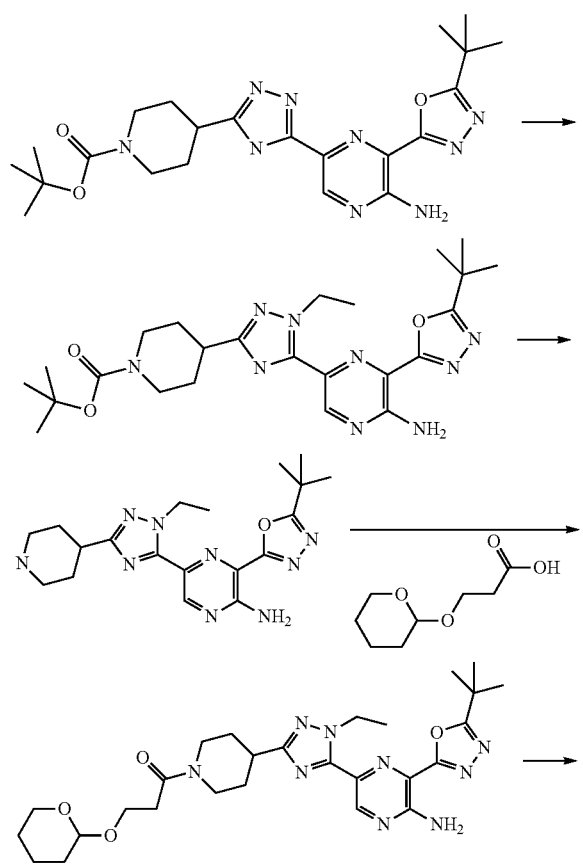

Example 3.1

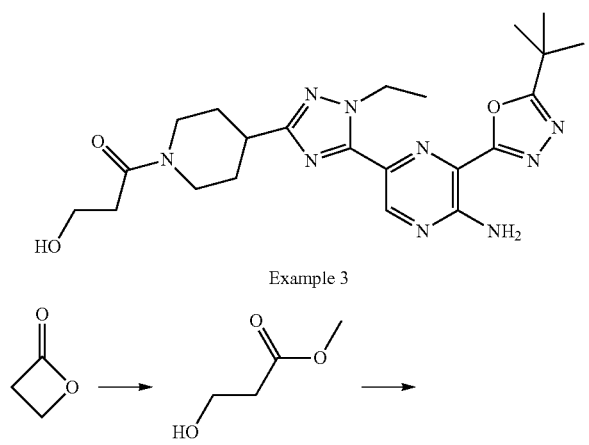

Example 3

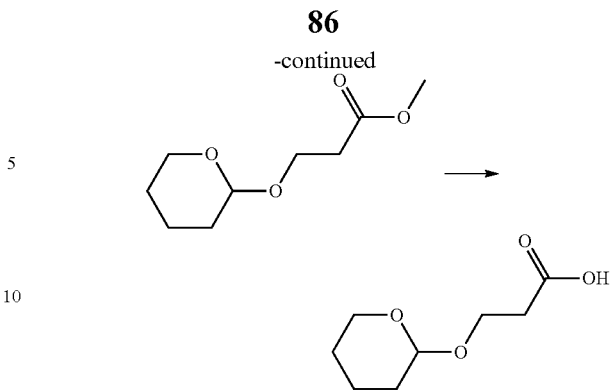

Pyridine 4-methylbenzenesulfonate (11.62 g, 46.24 mmol) was added to a suspension of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one (128 g, 231.19 mmol) in methanol (1 L) under nitrogen. The mixture was stirred at 60° C. for 1.5 hours. The mixture was soluble after 5 minutes. The mixture was held at 50° C. overnight during which time a precipitate formed. The solid material was isolated by filtration and washed with water and acetonitrile. This material still contained minor impurities from the previous stage and required further purification. The material was dissolved in dichloromethane and purified by flash chromatography on silica gel (0% methanol/DCM to 10% methanol/DCM). The desired product, 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (Example 3) (92 g, 85%), was thus isolated as a cream solid (Form A): $^1$H NMR Spectrum: (DMSO-d$_6$) 1.4-1.51 (12H, m), 1.51-1.78 (2H, m), 1.89-2.05 (2H, m), 2.72-2.86 (1H, m), 2.91-3.05 (1H, m), 3.12-3.24 (1H, m), 3.64 (2H, q), 3.83-4.01 (1H, m), 4.29-4.41 (1H, m), 4.47 (1H, t), 4.58 (2H, q), 8.26 (2H, s), 8.85 (1H, s); Mass Spectrum [M+H]$^+$=470.

1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one (Example 3.1) was prepared as follows:

1,8-Diazabicyclo[5.4.0]undec-7-ene (76 mL, 511.14 mmol) was added to a suspension of tert-butyl 4-(5-(5-amino-6-(5-tert-butyl-1,3,4-oxadiazol-2-yl)pyrazin-2-yl)-1H-1,2,4-triazol-3-yl)piperidine-1-carboxylate (150 g, 319.46 mmol) in 2-methylTHF (1.2 L). Iodoethane (46 mL, 575.03 mmol) was added and the mixture was stirred for 16 hours at 35° C. Further iodoethane (46 mL, 575.03 mmol) and 1,8-diazabicyclo[5.4.0]undec-7-ene (76 mL, 511.14 mmol) were added and stirring was continued for 24 hours at 35° C. The mixture was poured into water and the insoluble material was isolated by filtration, washed with water and MTBE and dried in vacuo to afford tert-butyl 4-(5-(5-amino-6-(5-tert-butyl-1,3,4-oxadiazol-2-yl)pyrazin-2-yl)-1-ethyl-1H-1,2,4-triazol-3-yl)piperidine-1-carboxylate (116 g, 73.0%) as a yellow solid. The filtrate was extracted with DCM and the organic solution was dried with magnesium sulfate, filtered, and concentrated under reduced pressure. The residue was purified by flash column chromatography on silica using gradient elution (30% MTBE/heptane to 100% MTBE). A second crop of the desired product (12 g, 24.12 mmol, 7.55%), was thus isolated as a yellow solid which was later combined with the first crop: $^1$H NMR Spectrum: (DMSO-d$_6$) 1.41 (9H, s), 1.44 (9H, s), 1.48 (3H, t), 1.52-1.69 (2H, m), 1.87-2.04 (2H, m), 2.79-3.03 (3H, m), 3.86-4.03 (2H, m), 4.59 (2H, q), 7.89 (2H, s), 8.85 (1H, s); Mass Spectrum [M+H]$^+$=498. THF may also be a suitable solvent for the above reaction.

TFA (400 mL) was added portionwise to a solution of tert-butyl 4-(5-(5-amino-6-(5-tert-butyl-1,3,4-oxadiazol-2-yl)pyrazin-2-yl)-1-ethyl-1H-1,2,4-triazol-3-yl)piperidine-1-carboxylate (126 g, 253.22 mmol) in DCM (400 mL). The mixture was stirred for 16 hours at room temperature. The mixture was concentrated under reduced pressure, dissolved in DCM (1 L) and added slowly to a vigorously stirred solution of concentrated aqueous ammonia (500 mL) in water at 0° C. The organic solution was separated from the aqueous and concentrated under reduced pressure* to afford 3-(5-tert-butyl-1,3,4-oxadiazol-2-yl)-5-(1-ethyl-3-(piperidin-4-yl)-1H-1,2,4-triazol-5-yl)pyrazin-2-amine (101 g, 100%) as a yellow solid: $^1$H NMR Spectrum: (DMSO-$d_6$) 1.4-1.52 (12H, m), 1.57-1.73 (2H, m), 1.83-1.93 (2H, m), 2.57-2.7 (2H, m), 2.71-2.84 (1H, m), 2.96-3.09 (2H, m), 4.58 (2H, q), 8.06 (2H, s), 8.84 (1H, s); Mass Spectrum [M+H]$^+$=398.

*In another experiment on a similar scale (approximately 170 g of starting material) the following isolation procedure was utilised. The layers were separated and the top layer (emulsion with a solid) was filtered. The solid was washed with DCM (0.5 L) and the filtrate was transferred to a separating funnel. The layers were separated and the aqueous layer was extracted with DCM (0.5 L). The organic layers were dried over MgSO$_4$, filtered and concentrated. The product was dried at 50° C. overnight (81.75 g). The solid from the extraction was slurried in water (200 mL) for 30 min at room temperature and filtered off. The product was dried at 50° C. in vacuo (61.8 g).

A further variation is as follows;

A suspension of tert-butyl 4-(5-(5-amino-6-(5-tert-butyl-1,3,4-oxadiazol-2-yl)pyrazin-2-yl)-1-ethyl-1H-1,2,4-triazol-3-yl)piperidine-1-carboxylate (3009.5 g, 6.05 mol) in DCM (9 L) was cooled to 5-10° C. under N$_2$. TFA (9 L) was added portionwise to the suspension whilst maintaining the temperature <30° C. The reaction mixture was stirred at room temperature for 1 h. The mixture was concentrated, the resulting residue was dissolved in water (30 L) and added slowly to a 35% aqueous ammonia solution (12 L) at 0-5° C. The suspension was stirred for 30 min then the product was filtered off and washed with water (2×6 L). The product was dried at 50° C. in vacuo for 2 days (2496 g).

O-(7-Azabenzotriazol-1-yl)-N,N,N',N'-tetramethyluronium hexafluorophosphate (HATU, 106 g, 279.51 mmol), was added portionwise to a stirred solution of 3-(tetrahydro-2H-pyran-2-yloxy)propanoic acid (44.3 g, 254.10 mmol) and N-ethyl-N-isopropylpropan-2-amine (89 mL, 508.21 mmol) dissolved in acetonitrile (600 mL) at 25° C. The resulting solution was stirred at 25° C. for 20 mn then 3-(5-tert-butyl-1,3,4-oxadiazol-2-yl)-5-(1-ethyl-3-(piperidin-4-yl)-1H-1,2,4-triazol-5-yl)pyrazin-2-amine (101 g, 254.10 mmol) was added portionwise washing the last portion into the mixture as a slurry in acetonitrile (300 mL). After stirring for 1 hour the precipitate was collected by filtration, washing with acetonitrile and drying in vacuo to afford 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one (128 g, 91%) as a beige solid. The filtrate was diluted with DCM (600 ml), washed with water, dried over magnesium sulfate and concentrated. The residue was purified by flash chromatography on silica gel eluting with a gradient of 2 to 2.5% 7N ammonia in methanol with dichloromethane. A second crop of the desired product (40 g, 72.2 mmol, 28.4%) was obtained as a cream solid which was combined with the first crop: $^1$H NMR Spectrum: (DMSO-$d_6$) 1.29-1.48 (16H, m), 1.48-1.75 (4H, m), 1.83-1.99 (2H, m), 2.48-2.68 (2H, m), 2.68-2.79 (1H, m), 2.87-2.99 (1H, m), 3.07-3.19 (1H, m), 3.32-3.42 (1H, m), 3.47-3.6 (1H, m), 3.64-3.75 (1H, m), 3.75-3.84 (1H, m), 3.84-3.95 (1H, m), 4.24-4.39 (1H, m), 4.47-4.6 (3H, m), 7.84 (2H, s), 8.79 (1H, s): Mass Spectrum [M+Na]$^+$=577.

Alternative Preparation:

To a solution of 3-(tetrahydro-2H-pyran-2-yloxy)propanoic acid (48.80 g 0.2774 mol) and N-ethyl-N-isopropylpropan-2-amine (86.96 mL, 0.4993 mol) in THF (552 mL) was added O-(7-Azabenzotriazol-1-yl)-N,N,N',N'-tetramethyluronium hexafluorophosphate (115.73 g, 0.3051 mol) portionwise at RT under nitrogen. The resulting mixture was stirred for 20 min then 3-(5-tert-butyl-1,3,4-oxadiazol-2-yl)-5-(1-ethyl-3-(piperidin-4-yl)-1H-1,2,4-triazol-5-yl)pyrazin-2-amine (122.5 g (110.25 g active), 0.2774 mol) was added portionwise over 1 h. After 3.5 h, the mixture was concentrated and the residue was slurried in MeCN (275 mL) for 15 min at room temperature. The product was filtered off, washed with MeCN (3×110 mL) and dried overnight at 50° C. in vacuo. This gave 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one (131.9 g, 96%). In a further alternative preparation, HBTU (O-(benzotriazol-1-yl)-N,N,N',N'-tetramethyluronium hexafluorophosphate) in THF may be used as coupling agent instead of HATU.

Alternative Preparation of Example 3

To a suspension of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one (131.9 g, 0.2382 mol) in methanol (1045 mL) was added pyridinium p-toluenesulfonate (11.97 g, 47.7 mmol) under N2. The reaction mixture was stirred at 60° C. for 5.5 h then at 50° C. overnight. The reaction mixture was cooled to 0° C. and the solid was filtered off. The product was slurried in water (250 mL) for 20 min at room temperature, filtered off, washed with water (3×40 mL) and dried at 50° C. in vacuo. This gave 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (21.4 g) as Form A (see below).

The methanol liquors were concentrated and the resulting solid was slurried in water (0.6 L) for 20 min at room temperature. The solid was isolated by filtration and washed with water (3×100 mL). The filter cake was slurried for a second time in water (0.5 L) for a further 20 minutes. The product was isolated by filtration, washed with water (100 mL) and dried at 50° C. in vacuo. This gave 81.9 g 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (81.9 g) as Form A.

Both crops were combined (103.3 g), seeded with Form B (16.68 g) and slurried in MeCN (826 mL) at room temperature overnight. This gave 117.4 g of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one as a pale yellow solid (117.4 g), Form B (see below). This material was further purified by slurrying in heptane (7.5 rel vols) for 1 hour. The mixture was filtered, pulled dry on the filter, and dried at 50° C. in a vacuum oven overnight to afford 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (102.5 g) as Form B.

Form B may also be made by slurrying Form A in MeCN without seeding.

Form A or B may also be converted to Form C as follows:

A suspension of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (eg Form B made by the processes outlined above) in IPA (12 vol) was heated at reflux until the solid dissolved. The solution was hot filtered then cooled to room temperature. This gave 1-(4-(5-(5-amino-6-(5-tert-butyl-1,3,4-oxadiazol-2-yl)pyrazin-2- yl)-1-ethyl-1H-1,2,4-triazol-3-yl)piperidin-1-yl)-3-hydroxypropan-1-one as a pale yellow solid (99.3 g, 97%) as Form C.

Form C may also be converted to Form B as follows:

In a 10 L flange flask, Form C (377.8 g portion 1) in MIBK (7900 mL) was heated to 110-115° C. to give a solution. The solution was allowed to cool to 97-103° C. and immediately polish filtered into a 50 L vessel containing a seed of Form B (0.8 g) in acetonitrile (8220 mL) stirring at −15° C. During the addition the temperature in the 50 L vessel was maintained between −15 and 25° C. by means of jacket cooling. Three further portions of the compound dissolved in MIBK were added by a similar method. To the resulting slurry was added a seed of form B (0.8 g) and the mixture was then stirred at 10-20° C. overnight. In-process analysis confirmed the desired form (Form B) with no Form C or amorphous visible. The mixture was filtered and washed with acetonitrile (3340 mL). The solid was oven dried for 2 days (solid was broken up during the drying to a powder and a mixture of small lumps ~1 mm to ~3-4 mm size) until constant weight was obtained. Yield=1532.8 g (93.5%)

3-(Tetrahydro-2H-pyran-2-yloxy)propanoic acid was prepared as follows:

To a stirred solution of methanol (2.4 L) and concentrated sulfuric acid (44.4 mL, 832.61 mmol) at 0° C. under nitrogen was added, dropwise, beta-propiolactone (175 mL, 2.78 mol). This solution was allowed to stir at room temperature for 2 days. The reaction mixture was cooled to 10° C. before adding, portionwise, sodium bicarbonate (145 g, 1.72 mol), the resulting suspension was left to stir at room temperature for 75 minutes. This solution was filtered, the filter-cake was washed with methanol (800 mL). The filtrate was evaporated to an oil which was redissolved in dichloromethane (1.2 L) and stirred for 60 minutes before refiltering. This solution was filtered before evaporating to give methyl 3-hydroxypropanoate (219 g, 76%) as an oil. $^1$H NMR Spectrum: (CDCl$_3$) 2.50 (2H, t), 3.63 (3H, s), 3.78 (2H, t).

Pyridinium p-toluenesulfonate (7.65 g, 30.45 mmol) was added to a clear solution of methyl 3-hydroxypropanoate (63.4 g, 609.00 mmol) and 3,4-dihydro-2H-pyran (78 mL, 852.60 mmol) in dichloromethane (650 mL) at room temperature under nitrogen to give a cloudy solution. This was allowed to stir at room temperature overnight. The reaction mixture was washed with water (250 mL) and brine (250 mL) before drying (MgSO$_4$) and evaporating to an oil. This crude product was purified by flash silica chromatography, elution gradient 15 to 30% EtOAc in heptane. Pure fractions were evaporated to dryness to afford methyl 3-(tetrahydro-2H-pyran-2-yloxy)propanoate (67.7 g, 59.0%) as a colourless oil: $^1$H NMR Spectrum: (CDCl$_3$) 1.47 (4H, dddd), 1.55-1.84 (2H, m), 2.55 (2H, t), 3.33-3.53 (1H, m), 3.53-3.7 (4H, m), 3.78 (1H, ddd), 3.93 (1H, dt), 4.42-4.72 (1H, m); Mass Spectrum [MH]$^+$=189.

Sodium hydroxide (2M, 349 mL, 697.58 mmol) was added to a solution of methyl 3-(tetrahydro-2H-pyran-2-yloxy)propanoate (67.68 g, 359.58 mmol) in THF (680 mL) at room temperature. The reaction mixture was stirred at room temperature for 3 hours. The THF was removed in vacuo, the aqueous layer was then washed with ethyl acetate (260 mL), before cooling to 0° C. and careful acidification to pH 5 by the addition of hydrochloric acid (2M). The product was extracted with ethyl acetate (3×250 mL) before drying (MgSO$_4$) and evaporation to give 3-(tetrahydro-2H-pyran-2-yloxy)propanoic acid (57.0 g, 91%) as a clear oil. This material was dissolved in ethyl acetate (750 mL) then washed with water (3×250 mL) and brine (250 mL) to remove remaining acetic acid. The organic solution was dried (MgSO$_4$) and evaporated to give 3-(tetrahydro-2H-pyran-2-yloxy)propanoic acid (45.67 g, 72.9%) as a colourless oil: $^1$H NMR Spectrum: $^1$H NMR (CDCl$_3$) 1.43-1.67 (4H, m), 1.65-1.95 (2H, m), 2.68 (2H, t), 3.48-3.58 (1H, m), 3.73 (1H, dt), 3.88 (1H, ddd), 4.02 (1H, dt), 4.59-4.7 (1H, m); Mass Spectrum [M−H]$^−$=173. Example 3 as isolated above was a crystalline solid in three different crystalline forms, described herein as Forms A, B and C.

The crystal structure of Form A of Example 3 may be characterised by XRPD and DSC.

The methods for carrying out these techniques are as described for Example 1.

| Ten X-Ray Powder Diffraction peaks for Example 3 Form A | |
|---|---|
| Angle 2-Theta (2θ) | Intensity % |
| 4.8 | 100 |
| 10.0 | 89.2 |
| 14.6 | 81.9 |
| 5.2 | 59.4 |
| 19.9 | 53.6 |
| 10.4 | 49.3 |
| 25.4 | 48.7 |
| 23.6 | 48.6 |
| 24.4 | 43.9 |
| 16.2 | 36.3 |

The XRPD for Example 3 Form A is shown in FIG. 3.

DSC analysis of Example 3 Form A shows an initial endotherm with an onset of 27.0° C. and a peak at 63.0° C., further endothermic shifts are seen with onsets and peaks at the following temperatures; 166.5° C. and 168.7° C., 172.2° C. and 173.2° C. and a final melt at 174.8° C. and a peak at 175.7° C. (FIG. 4).

Thus DSC analysis shows Example 3 Form A is a solvated material with an onset of desolvation at about 27.0° C. and a peak at about 63.0° C.

The X-ray powder diffraction spectra for Example 3 (Form A) showed the material to be crystalline. This material had a desolvation point of 28.0° C. (onset).

Example 3 can also exist in an alternative polymorphic form, referred to herein as Form B. Preparation of Form B was described above.

This material had a melting point of 172.5° C. (onset).

In a further aspect of the invention, there is provided a process for making Form B of Example 3 by slurrying a sample of Example 3 in acetonitrile. In a further aspect of the invention there is provided a process for making Form B of Example 3 from a solution of Form C of Example 3 in MIBK.

| Ten X-Ray Powder Diffraction peaks for Example 3 Form B | |
|---|---|
| Angle 2-Theta (2θ) | Intensity % |
| 5.8 | 100.0 |
| 10.9 | 59.8 |
| 11.5 | 33.8 |
| 25.9 | 18.2 |
| 17.3 | 15.8 |
| 24.0 | 14.1 |
| 19.1 | 13.4 |
| 12.9 | 11.7 |
| 24.7 | 11.1 |
| 27.2 | 9.7 |

The XRPD for Example 3 Form B is shown in FIG. 5.

DSC analysis of Example 3 Form B shows a melting endotherm with an onset of 172.5° C. and a peak at 174.2° C. (FIG. 6).

Thus DSC analysis shows Example 3 B is a high melting solid with an onset of melting at about 172.5° C. and a peak at about 174.2° C.

Example 3 may also exist in a third crystalline form, referred to herein as Form C. A process for making Form C material from eg Form B material was described above, by crystallisation from isopropyl alcohol (IPA).

Therefore in a further aspect of the invention there is provided a process for making Form C of Example 3 by crystallising Example 3 from IPA.

Example 3 Form C is characterised in providing at least one of the following 2θ values measured using CuKa radiation: 6.9 and 12.3. Example 3 Form C is characterised in providing an X-ray powder diffraction pattern, substantially as shown in Figure A. Ten X-Ray powder diffraction peaks are shown below:

| Ten X-Ray Powder Diffraction peaks for Example 3 Form C | |
|---|---|
| Angle 2-Theta (2θ) | Intensity % |
| 6.9 | 40.1 |
| 12.3 | 100.0 |
| 10.5 | 23.8 |
| 21.0 | 67.9 |
| 24.6 | 36.1 |
| 13.6 | 21.4 |
| 16.4 | 19.9 |
| 19.6 | 18.1 |
| 20.2 | 17.5 |
| 22.5 | 18.4 |

DSC analysis of Example 3 Form C shows a melting endotherm with an onset of 183.0° C. and a peak at 185.6° C. (Figure B).

Thus DSC analysis shows Example 3 Form C is a high melting solid with an onset of melting at about 183.0° C. and a peak at about 185.6° C.

Details of Techniques Used for Form C Analysis

X-Ray Powder Diffraction

Analytical Instrument: Panalytical Cubix.

The X-ray powder diffractogram was determined by mounting a sample of the crystalline material on a Panalytical single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 45 kV and 40 mA with a wavelength of 1.5418 angstroms. The X-ray beam was passed through a 0.04 rad soller slit, then an automatic variable divergence slit set at 20 mm and finally a 20 mm beam mask. The reflected radiation was directed through a 20 mm antiscatter slit and a 0.04 rad soller slit. The sample was exposed for 1.905 seconds per 0.0025067° 2-theta increment (continuous scan mode) over the range 2 degrees to 40 degrees 2-theta in theta-theta mode. The instrument was equipped with an X-Celerator detector. Control and data capture was by means of a Dell Pentium 4HT Workstation operating with X'Pert Industry software. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry

Analytical Instrument: TA Instruments Q1000 DSC.

Typically less than 5 mg of material contained in a standard aluminium pan fitted with a lid was heated over the temperature range 25° C. to 300° C. at a constant heating rate of 10° C. per minute. A purge gas using nitrogen was used—flow rate 50 ml per minute.

Example 4

(3R)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-butan-1-one

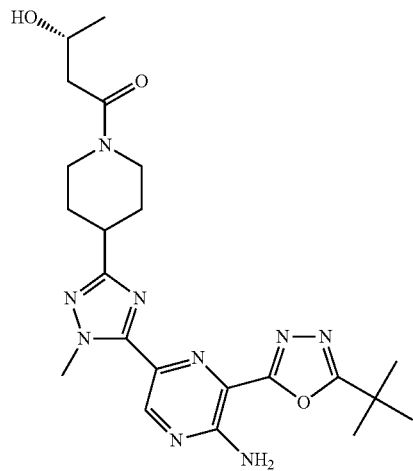 [SMILES: C[C@@H](O)CC(=O)N1CCC(c2nc(-c3cnc(N)c(-c4nnc(C(C)(C)C)o4)n3)n(C)n2)CC1]

2-(1H-Benzo[d][1,2,3]triazol-1-yl)-1,1,3,3-tetramethylisouronium tetrafluoroborate (201 mg, 0.63 mmol) was added to a stirred suspension of 3-(5-tert-butyl-1,3,4-oxadiazol-2-yl)-5-(1-methyl-3-(piperidin-4-yl)-1H-1,2,4-triazol-5-yl)pyrazin-2-amine (200 mg, 0.52 mmol, described in Example 1), N-ethyl-N-isopropylpropan-2-amine (0.273 mL, 1.56 mmol) and (R)-3-hydroxybutanoic acid (65.2 mg, 0.63 mmol) in N,N-dimethylformamide (3 mL). The resulting suspension was stirred at room temperature for 2 hours. The resulting mixture was purified by preparative HPLC using a Waters X-Bridge reverse-phase column (C-18, 5 microns silica, 30 mm diameter, 150 mm length, flow rate of 60 ml/minute) using an isocratic mixture of 31% acetonitrile in water (containing ammonium carbonate (2 g/L). The fractions containing the desired compound were evaporated to dryness to afford a pale yellow solid. This solid was stirred in acetonitrile (3 mL) at room temperature. The resulting solid was filtered, washed with cold acetonitrile and dried to afford the title compound (125 mg, 51.0%) as a pale yellow solid.

$^1$H NMR Spectrum: (CDCl$_3$) 1.24 (3H, d), 1.52 (9H, s), 1.85 (2H, m), 2.10 (2H, m), 2.35 (1H, dd), 2.55 (1H, d), 2.90 (1H, m), 3.05 (1H, m), 3.20 (1H, m), 3.90 (1H, m), 4.25 (1H, m), 4.31 (3H, s), 4.6 (1H, m), 9.03 (1H, s); Mass Spectrum [M+H]$^+$=470.

Example 5

(3S)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-butan-1-one

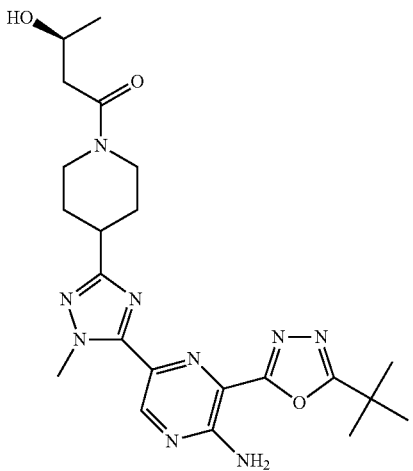 [SMILES: C[C@H](O)CC(=O)N1CCC(c2nc(-c3cnc(N)c(-c4nnc(C(C)(C)C)o4)n3)n(C)n2)CC1]

Using a similar procedure as Example 4, 3-(5-tert-butyl-1,3,4-oxadiazol-2-yl)-5-(1-methyl-3-(piperidin-4-yl)-1H-1,2,4-triazol-5-yl)pyrazin-2-amine was reacted with (S)-3-hydroxybutanoic acid to afford the title compound (167 mg, 68.2%) as a pale yellow solid. $^1$H NMR Spectrum: (CDCl$_3$) 1.24 (3H, d), 1.52 (9H, s), 1.85 (2H, m), 2.10 (2H, m), 2.35 (1H, dd), 2.55 (1H, d), 2.90 (1H, m), 3.05 (1H, m), 3.20 (1H, m), 3.90 (1H, m), 4.25 (1H, m), 4.31 (3H, s), 4.6 (1H, m), 9.03 (1H, s); Mass Spectrum [M+H]$^+$=470.

Example 6

(2R)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-2-methyl-propan-1-one

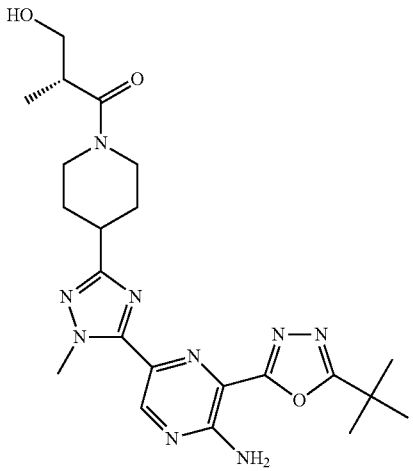 [SMILES: C[C@H](CO)C(=O)N1CCC(c2nc(-c3cnc(N)c(-c4nnc(C(C)(C)C)o4)n3)n(C)n2)CC1]

Using a similar procedure as Example 4, 3-(5-tert-butyl-1,3,4-oxadiazol-2-yl)-5-(1-methyl-3-(piperidin-4-yl)-1H-1,2,4-triazol-5-yl)pyrazin-2-amine was reacted with (R)-3-hydroxy-2-methylpropanoic acid to afford the title compound (87 mg, 47.4%) as a pale yellow solid.

$^1$H NMR Spectrum: (CDCl$_3$) 1.55 (9H, s), 1.61 (3H, s br), 1.8-2.0 (2H, m), 2.10-2.25 (2H, m), 2.90 (2H, m), 3.10 (1H, m), 3.3 (2H, m), 3.77 (2H, m), 4.33 (3H, s), 4.6 (1H, m), 9.05 (1H, s); Mass Spectrum [M+H]+=470.

Example 7

1-[4-[5-[5-amino-6-(5-tert-butyl-1,3,4-oxadiazol-2-yl)pyrazin-2-yl]-1-methyl-1,2,4-triazol-3-yl]-1-piperidyl]-2-hydroxy-2-methyl-propan-1-one

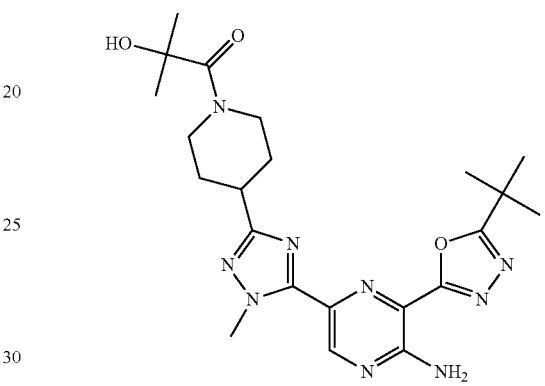

1-(3-Dimethylaminopropyl)-3-ethylcarbodiimide hydrochloride (100 mg, 0.52 mmol) was added in one portion to 2-hydroxy-2-methylpropanoic acid (38.0 mg, 0.37 mmol), 3-(5-tert-butyl-1,3,4-oxadiazol-2-yl)-5-(1-methyl-3-(piperidin-4-yl)-1H-1,2,4-triazol-5-yl)pyrazin-2-amine (100 mg, 0.26 mmol) and 2-hydroxy-pyridine N-oxide (57.9 mg, 0.52 mmol) dissolved in NMP (1.2 mL) under argon. The resulting solution was stirred at 25° C. for 3 hours. Pyridine (100 µL, 1.24 mmol) was added and the mixture was stirred for 18 hours. Additional 2-hydroxypyridine 1-oxide (57.9 mg, 0.52 mmol) and 1-(3-dimethylaminopropyl)-3-ethylcarbodiimide hydrochloride (100 mg, 0.52 mmol) was added. The mixture was then heated up to 70° C. for 48 hours, more 2-hydroxy-2-methylpropanoic acid (15 mg, 0.14 mmol), 1-(3-dimethylaminopropyl)-3-ethylcarbodiimide hydrochloride (50.0 mg, 0.26 mmol) and 2-hydroxypyridine 1-oxide (25.0 mg, 0.23 mmol) were added and the mixture was then kept to 70° C. for 8 hours. The solution was purified by preparative HPLC using a Waters X-Bridge reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent to afford the title compound (71 mg, 58%) as a pale yellow solid. $^1$H NMR Spectrum: (CDCl$_3$) 1.55 (15H, s br), 1.90 (2H, m), 2.15 (2H, m), 3.05-3.3 (4H, m), 4.32 (3H, s), 4.6 (1H, m), 9.03 (1H, s); Mass Spectrum [M+H]$^+$=470.

Example 8

3-[4-[5-[5-amino-6-(5-tert-butyl-1,3,4-oxadiazol-2-yl)pyrazin-2-yl]-1-methyl-1,2,4-triazol-3-yl]-1-piperidyl]-3-oxo-propanoic acid

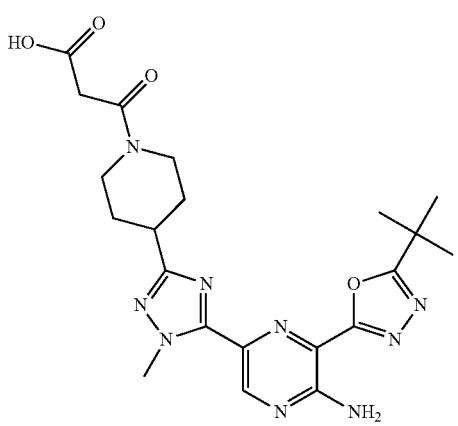 [SMILES: Cn1nc(C2CCN(C(=O)CC(=O)O)CC2)nc1-c1cnc(N)c(-c2nnc(C(C)(C)C)o2)n1]

Ethyl 3-chloro-3-oxopropanoate (0.037 mL, 0.29 mmol) was added dropwise to a stirred solution of 3-(5-tert-butyl-1,3,4-oxadiazol-2-yl)-5-(1-methyl-3-(piperidin-4-yl)-1H-1,2,4-triazol-5-yl)pyrazin-2-amine (100 mg, 0.26 mmol) and triethylamine (0.047 mL, 0.34 mmol) dissolved in $CH_2Cl_2$ (1.5 mL) over a period of 2 minutes at 0° C. under nitrogen. The mixture was stirred at 0° C. for 10 minutes then allowed to warm to room temperature and stirred for 1 hour. The mixture was evaporated, dissolved in DMF; a white solid was filtered off and the filtrate was purified by preparative HPLC using a Waters X-Terra reverse-phase column eluting with a mixture of water (containing 0.2% ammonium carbonate) and acetonitrile to afford ethyl 3-(4-(5-(5-amino-6-(5-tert-butyl-1,3,4-oxadiazol-2-yl)pyrazin-2-yl)-1-methyl-1H-1,2,4-triazol-3-yl)piperidin-1-yl)-3-oxopropanoate (80 mg, 61.7%) as a yellow solid. This material was suspended in THF (2 mL). 2N Sodium hydroxide (0.235 mL, 0.47 mmol) and water (0.5 ml) were added. The mixture was stirred at room temperature overnight. 2N Hydrochloric acid (230 μL) was added to the mixture. The solvents were evaporated. The residue was diluted with $CH_2Cl_2$ (30 mL) and water (5 mL). The organic phase was washed with brine and dried over $MgSO_4$. The solvents were evaporated. The resulting foam was triturated in ether. The resulting yellow solid was filtered, dried, triturated in acetonitrile (3 mL). The yellow solid was collected by filtration, dried at 40° C. to afford the title compound (50 mg, 68%) as a yellow solid.

$^1$H NMR Spectrum: (DMSO-$d_6$) 1.46 (9H, s), 1.58 (1H, m), 1.74 (1H, m), 1.98 (2H, m), 2.84 (1H, m), 3.0 (1H, m), 3.21 (1H, m), 3.46 (2H, m), 3.83 (1H, m), 4.22 (3H, s), 4.34 (1H, m), 7.8-8.2 (1H, m), 8.87 (1H, s); Mass Spectrum [M+H]$^+$=470.

Example 9

3-[4-[5-[5-amino-6-(5-tert-butyl-1,3,4-oxadiazol-2-yl)pyrazin-2-yl]-1-ethyl-1,2,4-triazol-3-yl]-1-piperidyl]-3-oxo-propanoic acid

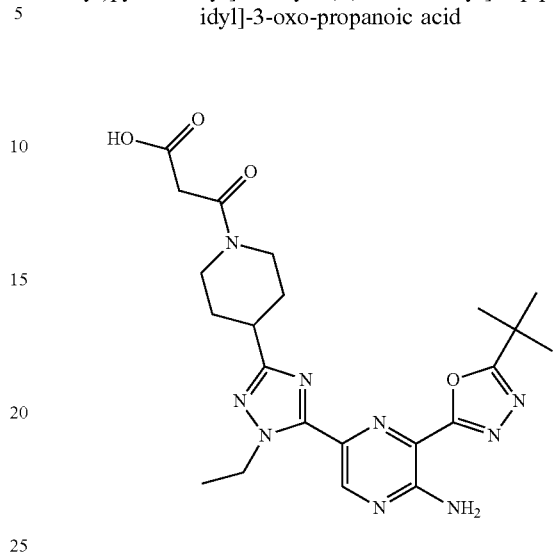

O-(7-Azabenzotriazol-1-yl)-N,N,N',N'-tetramethyluronium hexafluorophosphate (474 mg, 1.25 mmol) was added over 30 seconds in portions to a stirred solution of 3-ethoxy-3-oxopropanoic acid (150 mg, 1.13 mmol), N-ethyl-N-isopropylpropan-2-amine (0.394 mL, 2.26 mmol) and 3-(5-(tert-butyl)-1,3,4-oxadiazol-2-yl)-5-(1-ethyl-3-(piperidin-4-yl)-1H-1,2,4-triazol-5-yl)pyrazin-2-amine (450 mg, 1.13 mmol) dissolved in DMF (20 mL) at 50° C. The resulting solution was sampled after 1 min (complete reaction) and immediately allowed to cool to ambient temperature. The reaction mixture was concentrated and diluted with EtOAc (100 mL), and washed sequentially with water (20 mL) and saturated brine (20 mL). The organic layer was dried over $MgSO_4$, filtered and evaporated to afford crude ethyl 3-(4-(5-(5-amino-6-(5-(tert-butyl)-1,3,4-oxadiazol-2-yl)pyrazin-2-yl)-1-ethyl-1H-1,2,4-triazol-3-yl)piperidin-1-yl)-3-oxopropanoate (850 mg).

Some of that material (780 mg) was dissolved in THF (20 ml). To this solution was added 2N aqueous sodium hydroxide (2.3 ml, 4.57 mmol) and water (5 ml) followed by methanol (5 ml) to give a clear solution. The mixture was stirred at room temperature for 3 hours. The THF was evaporated. The aqueous layer was acidified to pH3 with 2N aqueous hydrochloric acid (2.5 ml). Dichloromethane (50 ml) was added and the organic phase extracted. The organic phase was washed with brine (10 ml) and dried over $MgSO_4$. The solvents were evaporated. The resulting gum was purified by preparative HPLC (Waters X-Bridge Prep C18 OBD column, 5μ silica, 50 mm diameter, 100 mm length), using decreasingly polar mixtures of water (containing 1% ammonia) and acetonitrile as eluents. Fractions containing the desired compound were evaporated to dryness to afford pure ammonium salt. This was solubilised in water and acidified to pH3 with 2N hydrochloric acid (~0.3 ml). Dichloromethane (50 mL) was added and the organic phase separated, washed with brine (5 ml) and dried over $MgSO_4$. After filtration the resulting solution was evaporated to dryness and the residue was triturated with diethyl ether (5 mL) and filtered to afford 3-(4-(5-(5-amino-6-(5-(tert-butyl)-1,3,4-oxadiazol-2-yl)pyrazin-2-yl)-1-ethyl-1H-1,2,4-triazol-3-yl)piperidin-1-yl)-3-oxopropanoic acid (195 mg, 26.5%) as a cream solid. $^1$H NMR Spectrum: (DMSO-$d_6$) 1.45 (9H, s), 1.48 (3H, m), 1.55-1.62 (1H, m), 1.70-1.80 (1H, m), 1.95-2.05 (2H, m), 2.80-2.90 (1H, m), 2.95-3.05 (1H, m), 3.15-

3.25 (1H, m), 3.45 (2H, s), 3.78-3.85 (1H, m), 4.30-4.40 (1H, m), 4.55-4.65 (2H, m), 7.80-8.00 (2H, br s), 8.88 (1H, s), 12.60 (1H, s); Mass Spectrum [M+H]⁺=484

Example 10

(2S)-1-[4-[5-[5-amino-6-(5-tert-butyl-1,3,4-oxadiazol-2-yl)pyrazin-2-yl]-1-ethyl-1,2,4-triazol-3-yl]-1-piperidyl]-2,3-dihydroxy-propan-1-one To a mixture of 3-(5-(tert-butyl)-1,3,4-oxadiazol-2-yl)-5-(1-ethyl-3-(piperidin-4-yl)-1H-1,2,4-triazol-5-yl)pyrazin-2-amine (257 mg, 0.50 mmol, TFA salt), potassium (S)-2,2-dimethyl-1,3-dioxolane-4-carboxylate (101 mg, 0.55 mmol) and EDCI (105 mg, 0.55 mmol) in DCM (5 mL) were added 1-hydroxy-1H-benzotriazol hydrate (85 mg, 0.56 mmol) and DIPEA (194 mg, 1.50 mmol). The mixture was stirred for 16 hours at room temperature. Water was added to the mixture and the mixture was extracted with DCM. The organic layers were washed with brine and dried over Na₂SO₄, filtered and concentrated to give (S)-(4-(5-(5-amino-6-(5-(tert-butyl)-1,3,4-oxadiazol-2-yl)pyrazin-2-yl)-1-ethyl-1H-1,2,4-triazol-3-yl)piperidin-1-yl)(2,2-dimethyl-1,3-dioxolan-4-yl)methanone (320 mg). Mass Spectrum [M+H]⁺=526. To a mixture of (S)-(4-(5-(5-amino-6-(5-(tert-butyl)-1,3,4-oxadiazol-2-yl)pyrazin-2-yl)-1-ethyl-1H-1,2,4-triazol-3-yl)piperidin-1-yl)(2,2-dimethyl-1,3-dioxolan-4-yl)methanone (320 mg) in DCM (10 mL) was added dropwise TFA (1.6 ml, 20.77 mmol). The mixture was stirred for 16 h at r.t, concentrated and purified by preparative HPLC (Waters XBridge Prep C18 OBD column, 5μ silica, 19 mm diameter, 100 mm length) using decreasingly polar mixtures of water (containing 0.1% NH₃) and MeCN as the eluant. The fractions containing the desired compound were evaporated to dryness to afford the title compound (142 mg, 48%) as a white solid. ¹H NMR Spectrum (400 Hz, DMSO-d₆, 30° C.): 1.45 (12H, m), 1.56 (1H, m), 1.70 (1H, m), 1.98 (2H, m), 2.85 (1H, m), 3.00 (1H, m), 3.20 (1H, m), 3.45 (1H, s), 3.55 (1H, s), 4.05 (1H, m), 4.35 (2H, m), 4.60 (2H, m), 4.70 (1H, m), 4.85 (1H, m), 7.90 (2H, m), 8.85 (1H, s); Mass Spectrum [M+H]⁺=486.

Example 11

(2R)-1-[4-[5-[5-amino-6-(5-tert-butyl-1,3,4-oxadiazol-2-yl)pyrazin-2-yl]-1-ethyl-1,2,4-triazol-3-yl]-1-piperidyl]-2,3-dihydroxy-propan-1-one 3-(5-(Tert-butyl)-1,3,4-oxadiazol-2-yl)-5-(1-ethyl-3-(piperidin-4-yl)-1H-1,2,4-triazol-5-yl)pyrazin-2-amine was reacted with potassium (R)-2,2-dimethyl-1,3-dioxolane-4-carboxylate, using a similar procedure than described in Example 10 to provide the title compound (0.145 g, 40%) as a solid. ¹H NMR Spectrum (400 Hz, DMSO-d₆, 30° C.): 1.45 (12H, m), 1.60 (2H, m), 1.98 (2H, m), 2.85 (1H, m), 3.00 (1H, m), 3.17 (1H, m), 3.45 (1H, s), 3.55 (1H, s), 4.05 (1H, m), 4.35 (2H, m), 4.60 (2H, m), 4.70 (1H, m), 4.85 (1H, m), 7.90 (2H, m), 8.85 (1H, s); Mass Spectrum [M+H]⁺=486.

BRIEF DESCRIPTION OF THE FIGURES

FIG. 1 shows an X-Ray powder Diffraction Pattern for Example 1 Form A.
FIG. 2 shows a DSC Thermogram for Example 1 Form A.
FIG. 3 shows an X-Ray powder Diffraction Pattern for Example 3 Form A.
FIG. 4 shows a DSC Thermogram for Example 3 Form A.
FIG. 5 shows an X-Ray powder Diffraction Pattern for Example 3 Form B.
FIG. 6 shows a DSC Thermogram for Example 3 Form B.
FIG. 7 shows an X-Ray powder Diffraction Pattern for Example 3 Form C.
FIG. 8 shows a DSC Thermogram for Example 3 Form C.
FIG. 9 shows Tumour Growth Inhibition by Example 3 in Combination with AKT inhibitor (AZD5363)—sequential administration
FIG. 10 shows Tumour Growth Inhibition by Example 3 in Combination with AKT inhibitor (AZD5363), co-administration
FIG. 11 shows Tumour Growth Inhibition by Example 3 in Combination with PARP inhibitor (Olaparib) in BT474 xenograft model
FIG. 12 shows Tumour Growth Inhibition by Example 3 in Combination with PARP inhibitor (Olaparib) MCF7 xenograft model
FIG. 13 shows Tumour Growth Inhibition by Example 3 in Combination with (AZD8186)

The invention claimed is:
1. A compound of the Formula (I)

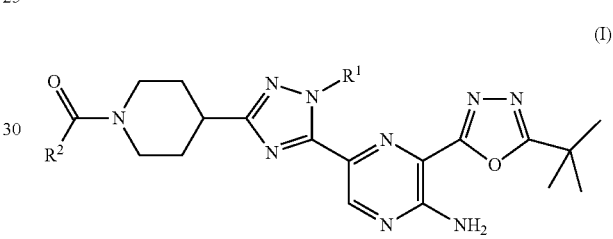

(I)

wherein
R¹ is methyl or ethyl; and
R² is (C2-3)alkyl substituted by hydroxy;
or a pharmaceutically-acceptable salt thereof.
2. The compound as claimed in claim 1, or a pharmaceutically-acceptable salt thereof, wherein R² is selected from groups (i) to (xi):

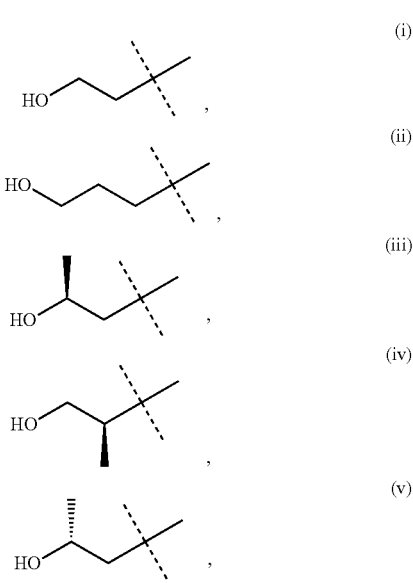

-continued

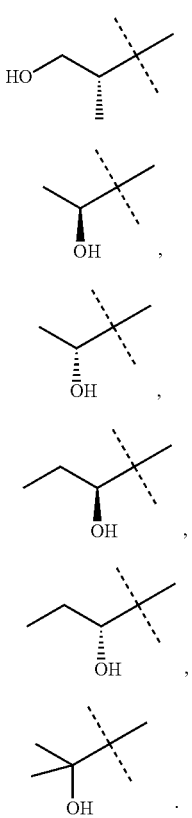

3. The compound as claimed in claim 2, or a pharmaceutically-acceptable salt thereof wherein $R^2$ is selected from groups (i) to (vi).

4. The compound as claimed in claim 2, or a pharmaceutically-acceptable salt thereof wherein R2 is group (i).

5. The compound as claimed in claim 1, or a pharmaceutically-acceptable salt thereof wherein R1 is methyl.

6. The compound as claimed in claim 1, or a pharmaceutically-acceptable salt thereof wherein R1 is ethyl.

7. The compound as claimed in claim 1 or a pharmaceutically-acceptable salt thereof, which compound is selected from:
  1-[4-[5-[5-amino-6-(5-tert-butyl-1,3,4-oxadiazol-2-yl) pyrazin-2-yl]-1-methyl-1,2,4-triazol-3-yl]-1-piperidyl]-3-hydroxy-propan-1-one;
  1-[4-[5-[5-amino-6-(5-tert-butyl-1,3,4-oxadiazol-2-yl) pyrazin-2-yl]-1-ethyl-1,2,4-triazol-3-yl]-1-piperidyl]-3-hydroxy-propan-1-one;
  (3R)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-butan-1-one;
  (3 S)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-butan-1-one;
  (2R)-1-[4-[5-[5-amino-6-(5-tert-butyl-1,3,4-oxadiazol-2-yl)pyrazin-2-yl]-1-methyl-1,2,4-triazol-3-yl]-1-piperidyl]-3-hydroxy-2-methyl-propan-1-one;
  1-[4-[5-[5-amino-6-(5-tert-butyl-1,3,4-oxadiazol-2-yl) pyrazin-2-yl]-1-methyl-1,2,4-triazol-3-yl]-1-piperidyl]-2-hydroxy-2-methyl-propan-1-one.

8. A pharmaceutical composition comprising a compound of Formula (I) or a pharmaceutically-acceptable salt thereof, as claimed in claim 1, and a pharmaceutically-acceptable diluent or carrier.

9. A crystalline form of 1-[4-[5-[5-amino-6-(5-tert-butyl-1,3,4-oxadiazol-2-yl)pyrazin-2-yl]-1-ethyl-1,2,4-triazol-3-yl]-1-piperidyl]-3-hydroxy-propan-1-one, or a pharmaceutically acceptable salt thereof.

10. The crystalline form as claimed in claim 9, which is 1-[4-[5-[5-amino-6-(5-tert-butyl-1,3,4-oxadiazol-2-yl) pyrazin-2-yl]-1-ethyl-1,2,4-triazol-3-yl]-1-piperidyl]-3-hydroxy-propan-1-one Form A.

11. The crystalline form as claimed in claim 9, which is 1-[4-[5-[5-amino-6-(5-tert-butyl-1,3,4-oxadiazol-2-yl) pyrazin-2-yl]-1-ethyl-1,2,4-triazol-3-yl]-1-piperidyl]-3-hydroxy-propan-1-one Form B.

12. The crystalline form as claimed in claim 9, which is 1-[4-[5-[5-amino-6-(5-tert-butyl-1,3,4-oxadiazol-2-yl) pyrazin-2-yl]-1-ethyl-1,2,4-triazol-3-yl]-1-piperidyl]-3-hydroxy-propan-1-one Form C.

* * * * *